US010390522B2

(12) United States Patent
Burova et al.

(10) Patent No.: US 10,390,522 B2
(45) Date of Patent: Aug. 27, 2019

(54) NON-HUMAN ANIMALS HAVING A HUMANIZED PROGRAMMED CELL DEATH 1 GENE

(71) Applicant: Regeneron Pharmaceuticals, Inc., Tarrytown, NY (US)

(72) Inventors: Elena Burova, Mount Kisco, NY (US); Alexander O. Mujica, Elmsford, NY (US); Ka-Man Venus Lai, Tarrytown, NY (US); Andrew J. Murphy, Croton-on-Hudson, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 14/744,592

(22) Filed: Jun. 19, 2015

(65) Prior Publication Data

US 2015/0366174 A1    Dec. 24, 2015

Related U.S. Application Data

(60) Provisional application No. 62/014,181, filed on Jun. 19, 2014, provisional application No. 62/086,518, filed on Dec. 2, 2014, provisional application No. 62/138,221, filed on Mar. 25, 2015.

(51) Int. Cl.
| | | |
|---|---|---|
| *A01K 67/027* | (2006.01) |
| *C07H 21/04* | (2006.01) |
| *C07K 1/00* | (2006.01) |
| *A61K 39/00* | (2006.01) |
| *C07K 14/47* | (2006.01) |
| *C07K 16/28* | (2006.01) |
| *C12Q 1/6886* | (2018.01) |
| *G01N 33/50* | (2006.01) |
| *A61K 49/00* | (2006.01) |
| *C07K 14/435* | (2006.01) |

(52) U.S. Cl.
CPC ...... *A01K 67/0278* (2013.01); *A61K 49/0008* (2013.01); *C07K 14/4747* (2013.01); *C07K 16/2803* (2013.01); *C12Q 1/6886* (2013.01); *G01N 33/5038* (2013.01); *A01K 2207/15* (2013.01); *A01K 2217/05* (2013.01); *A01K 2217/072* (2013.01); *A01K 2227/105* (2013.01); *A01K 2267/0331* (2013.01); *C07K 14/435* (2013.01); *C07K 2319/00* (2013.01); *C07K 2319/02* (2013.01); *C07K 2319/03* (2013.01); *C12Q 2600/106* (2013.01); *C12Q 2600/158* (2013.01); *G01N 2333/57* (2013.01); *G01N 2333/70503* (2013.01); *G01N 2500/10* (2013.01)

(58) Field of Classification Search
CPC ............ A01K 67/0275; A01K 67/0278; A01K 2207/15; A01K 2217/072; A01K 2227/105; C07K 14/435; C07K 14/4747; C07K 2319/02; C07K 2319/03; C07H 21/04
USPC ...... 800/18; 530/350; 536/23.4, 23.53, 24.1; 424/192.1
See application file for complete search history.

(56) References Cited

U.S. PATENT DOCUMENTS

| | | |
|---|---|---|
| 5,629,204 A | 5/1997 | Honjo et al. |
| 5,698,520 A | 12/1997 | Honjo et al. |
| 6,586,251 B2 | 7/2003 | Economides et al. |
| 7,294,754 B2 | 11/2007 | Poueymirou et al. |
| 7,414,171 B2 | 8/2008 | Honjo et al. |
| 7,432,059 B2 | 10/2008 | Freeman et al. |
| 7,709,214 B2 | 5/2010 | Freeman et al. |
| 8,217,149 B2 | 7/2012 | Irving et al. |
| 8,354,389 B2 | 1/2013 | Frendewey et al. |
| 8,518,392 B2 | 8/2013 | Frendewey et al. |
| 8,697,851 B2 | 4/2014 | Frendewey et al. |
| 2004/0213795 A1 | 10/2004 | Collins et al. |

FOREIGN PATENT DOCUMENTS

| | | |
|---|---|---|
| CN | 101213297 A | 7/2008 |
| CN | 102892785 A | 1/2013 |
| CN | 103830725 A | 6/2014 |
| EP | 1 334 659 B1 | 1/2012 |
| JP | 2012-50451 A | 3/2012 |
| RU | 2 425 880 C2 | 2/2011 |
| WO | WO 02/36789 A2 | 5/2002 |
| WO | WO 2013/063361 A1 | 5/2013 |

OTHER PUBLICATIONS

Goldman et al., 2004, Med Sci Monit, vol. 10, No. 11, RA274-285.*
Shinohara et al., 2007, Transgenic research, vol. 16, p. 333-339.*
Houdebine, Louis-Marie, 2007, Methods in Molecular Biology, vol. 360, p. 163-202.*
Carstea et al., 2009, World Journals of Stem Cells, vol. 1, No. 1, p. 22-29.*
Maksimenko et al., 2013, Acta Naturae, vol. 5, No. 1, p. 33-46.*
Alarcon-Riquelme et al., 2004, US 20040033497 A1.*
Carter, L.L. et al., "PD-1/PD-L1, but not PD-1/PD-L2, interactions regulate the severity of experimental autoimmune encephalomyelitis" J. Neuroimmunol. (2007) pp. 124-134, vol. 182(1-2).
Chen, L. et al., "Overexpression of program death-1 in T cells has mild impact on allograft survival" Europ. Soc. Organ Transplant. (2007) pp. 21-29, vol. 21.

(Continued)

*Primary Examiner* — Shin Lin Chen
(74) *Attorney, Agent, or Firm* — Scully, Scott, Murphy & Presser, P.C.; Margarita Zippin

(57) ABSTRACT

Non-human animals, and methods and compositions for making and using the same, are provided, wherein the non-human animals comprise a humanization of a Programmed cell death 1 (Pdcd1) gene. The non-human animals may be described, in some embodiments, as having a genetic modification to an endogenous Pdcd1 gene so that the non-human animals express a PD-1 polypeptide that includes a human portion and an endogenous portion (e.g., a non-human portion).

15 Claims, 11 Drawing Sheets

Specification includes a Sequence Listing.

(56) References Cited

OTHER PUBLICATIONS

Ishida, Y. et al., "Induced expression of PD-1, a novel member of the immunoglobulin gene superfamily, upon programmed cell death" EMBO J. (1992) pp. 3887-3895, vol. 11, No. 11.
Iwai, Y. et al., "PD-1 blockade inhibits hematogenous spread of poorly immunogenic tumor cells by enhanced recruitment of effector T cells" Intern. Immunol. (2004) pp. 133-144, vol. 17, No. 2.
Keir, M. E. et al., "PD-1 Regulates Self-Reactive CD8+ T Cell Responses to Antigen in Lymph Nodes and Tissues" J. Immunol. (2007) pp. 5064-5070, vol. 179.
Keir, M. E. et al., "Programmed Death-1 (PD-1):PD-Ligand 1 Interactions Inhibit TCR-Mediated Positive Selection of Thymocytes" J. Immunol. (2005) pp. 7372-7379, vol. 175.
Keir, M.E., et al., "PD-1 and its Ligands in Tolerance and Immunity" Annu. Rev. Immunol. (2008) pp. 677-704, vol. 26.
Lee, Y.H. et al., "Meta-analysis of genetic polymorphisms in programmed cell death 1" Z. Rheumatol. (2014) pp. 230-239, vol. 72.
Mansur, A. et al., "Ninety-Day Survival Rate of Patients With Sepsis Relates to Programmed Cell Death 1 Genetic Polymorphism rs11568821" J. Investig. Med. (2014) pp. 638-643, vol. 62, No. 3.
Nasi, M. et al., "Novel genetic association of TNF-a-238 and PDCD1-7209 polymorphisms with long-term non-progressive HIV-1 infection" Intern. J. Infect. Dis. (2013) pp. e845-e850, vol. 17.
Nielsen, C. et al., "Alternative splice variants of the human PD-1 gene" Cell. Immunol. (2005) pp. 109-116, vol. 235, No. 2.
Nishimura, H. et al., "Development of Lupus-like Autoimmune Diseases by Disruption of the PD-1 Gene Encoding an ITIM Motif-Carrying Immunoreceptor" Immunity (1999) pp. 141-151, vol. 11.
Nishimura, H. et al., "Autoimmune Dilated Cardiomyopathy in PD-1 Receptor-Deficient Mice" Science (2001) pp. 319-322, vol. 291.
Nishimura, H. et al., "Novel genetic association of TNF-a-238 and PDCD1-7209 polymorphisms with long-term non-progressive HIV-1 infection" Intern. Immunol. (1998) pp. 1563-1573, vol. 10, No. 10.
Okazaki, T. et al., "PD-1 and LAG-3 inhibitory co-receptors act synergistically to prevent autoimmunity in mice" J. Exp. Med. (2011) pp. 395-407, vol. 208, No. 2.
Pedoeem, A. et al., "Programmed death-1 pathway in cancer and autoimmunity" Clin. Immunol. (2014) pp. 145-152, vol. 153.
Philips, G.K. et al., "Therapeutic uses of anti-PD-1 and anti-PD-L1 antibodies" Intern. Immunol. (2014) 8 pages.
Piskin, I.E. et al., "PD-1 Gene Polymorphism in Children with Subacute Sclerosing Panencephalitis" Neuropediatrics (2013) pp. 187-190, vol. 44, No. 4.
Poueymirou, W.T. et al., "F0 generation mice fully derived from gene-targeted embryonic stem cells allowing immediate phenotypic analyses" Nature Biotech. (2007) pp. 91-99, vol. 25, No. 1.
Valenzuela, D.M. et al., "High-throughput engineering of the mouse genome coupled with high-resolution expression analysis" Nature Biotech. (2003) pp. 652-659, vol. 21, No. 6.
Wan, B. et al., "Aberrant Regulation of Synovial T Cell Activation by Soluble Costimulatory Molecules in Rheumatoid Arthritis" J. Immunol. (2006) pp. 8844-8850, vol. 177, No. 12.
Chen, Y. et al., "Programmed Death (PD)-1-Deficient Mice are Extremely Sensitive to Murine Hepatitis Virus Strain-3 (MHV-3) Infection" PLOS Pathogens (Jul. 2011) pp. 1-12, vol. 7, No. 7, e1001347.
Chen, L. et al., "Role of the Immune Modulator Programmed Cell Death-1 during Development and Apoptosis of Mouse Retinal Ganglion Cells" Investigative Ophthalmology & Visual Science (Oct. 2009) pp. 4941-4948, vol. 50, No. 10.
Collins, M. et al., "The B7 family of immune-regulator ligands" Genome Biology (2005) pp. 223.1-223.7, vol. 6, No. 223.
Francisco, L.M. et al., "PD-L1 regulates the development, maintenance, and function of induced regulatory T cells" J. Exp. Med. (2009) pp. 3015-3029, vol. 206, No. 13.

Guo, G. et al., "The development of endometrial hyperplasia in aged PD-1-deficient female mice" Diagnostic Pathology (2014) pp. 1-7, vol. 9, No. 97.
Kasagi, S. et al., "Anti-Programmed Cell Death 1 Antibody Reduces CD4 +PD-1+ T Cells and Relieves the Lupus-Like Nephritis of NZB/W F1 Mice" J Immunol (2010) pp. 2337-2347, vol. 184.
Kasagi, S. et al., "PD-1 and Autoimmunity" Critical Reviews in Immunology (2011) pp. 265-295, vol. 31, No. 4.
Lázár-Molnára, E. et al., "Programmed death-1 (PD-1)-deficient mice are extraordinarily sensitive to tuberculosis" PNAS (Jul. 2010) pp. 13402-13407, vol. 107, No. 30.
Latchman, Y. E. et al., "PD-L1-deficient mice show that PD-L1 on T cells, antigen-presenting cells, and host tissues negatively regulates T cells" PNAS (Jul. 2004) pp. 10691-10696, vol. 101, No. 29.
Özkaynak, E. et al., "Programmed Death-1 Targeting Can Promote Allograft Survival" J Immunol (2002) pp. 6546-6553, vol. 169.
Paterson, A.M. et al., "The Programmed Death-1 Ligand 1:B7-1 Pathway Restrains Diabetogenic Effector T Cells In Vivo" J Immunol (2011) pp. 1-9.
Shinohara, T. et al., "Structure and Chromosomal Localization of the Human PD-1 Gene (PDCD1)" Genomics (1994) pp. 704-706, vol. 23.
Terawaki, S. et al., "IFN-α Directly Promotes Programmed Cell Death-1 Transcription and Limits the Duration of T Cell-Mediated Immunity" J Immunol (2011) pp. 2772-2779, vol. 186.
Wang, S. et al., "Molecular Modeling and Functional Mapping of B7-H1 and B7-DC Uncouple Costimulatory Function from PD-1 Interaction" J. Exp. Med (May 2003) pp. 1083-1091, vol. 197, No. 9.
Xiao, G. et al., "Activator protein 1 suppresses antitumor T-cell function via the induction of programmed death 1" PNAS (Sep. 2012) pp. 15419-15424, vol. 109, No. 38.
Yao, S. et al., "PD-1 on dendritic cells impedes innate immunity against bacterial infection" Blood (2009) pp. 5811-5818, vol. 113.
Burova E. et al., "Abstract 266: Antitumor Activity of REGN2810, a Fully Human Anti-PD-1 Monoclonal Antibody, Against MC38.Ova Tumors Grown in Immune-Competent Humanized PD-1 Mice", Cancer Research 75(15):2 pages (Aug. 1, 2015).
Devoy A. et al., "Genonnically Humanized Mice: Technologies and Promises", Nature Reviews Genetics 13:14-20 (Jan. 1, 2012).
Selby M. et al., "Antitumor Activity of Concurrent Blockade of Immune Checkpoint Molecules CTLA-4 and PD-1 in Preclinical Models", J Clin Oncol 31:2 pages, Abstract 3061 (May 31, 2013).
International Search Report and Written Opinion dated Oct. 2, 2015 received from International Application No. PCT/US2015/036649.
Akkaya B. et al., "In Vivo Characterization of Inhibitory Anti-PD-1 Antibody Superagonists", Abstract 80 in Abstracts of the Annual Congress of the British Society for Immunology 5-8 (Dec. 2011).
Wang Z. et al., "HuGEMM-h/mPD1 Mouse Models for Assessing Anti-Human PD1 Therapeutics", A11 in Poster Session A, AACR-NCI-EORTC International Conference on Molecular Targets and Cancer Therapeutics (Nov. 6, 2015).
"Humanized PD-1 Knock-In Mouse Model", Oxford University Innovation (2017), retrieved in Jul. 2017 from https://innovation.ox.ac.uk/materials/humanized-pd-1-knock-murine-model.
"HuGEMM™ and HuCELL™ Models", huGEMM & HuCELL FactSheet, CrownBio, (v2.1) (Oct. 11, 2016).
"HuGEMM™ PD-1 Mouse Model", Crown Bioscience Inc. (2017).
Communicaton dated Jul. 24, 2017 issued from the European Patent Office in corresponding European Application No. 15738177.3 (EP 3157956 A), which transmits the following: Third Party Observations (5 pages), which in turn has the following three attachments: Document 1: Extract from PhD thesis "Modulation of the PD-1 pathway by inhibitory antibody superagonists" by Billur Akkaya (thesis title page, pp. i-vii, 65-67 and 89-98 only).
Record page from https://ora.ox.ac.uk/objects/uuid:1c97e755-e61d-4d55-8b20-b25462826eee, containing bibliographic details and abstract for the PhD thesis by Akkaya B., entitled "Modulation of the PD-1 Pathway by Inhibitory Antibody Superagonists" (2013).
Bergin M. et al., "Signalling Through PD-1 Inhibits Mouse T Cell Proliferation", Abstract 100 in Abstracts of the Annual Congress of the British Society for Immunology 5-8 (Dec. 2011).

(56) References Cited

OTHER PUBLICATIONS

Moisini I. et al., "Redirecting Therapeutic T Cells Against Myelin-Specific T Lymphocytes Using a Humanized Myelin Basic Protein-HLA-DR2-Zeta Chimeric Receptor", The Journal of Immunology 180:3601-3611 (2008).

Petkova S.B. et al., "Enhanced Half-Life of Genetically Engineered Human IgG1 Antibodies in a Humanized FcRn Mouse Model: Potential Application in Humorally Mediated Autoimmune Disease", International Immunology 18 (12):1759-1769 (2006).

Sonderstrup G., "Development of Humanized Mice as a Model of Inflammatory Arthritis", Springer Semin Immunopathol 25:35-45 (2003).

Chen D. et al., "Characterization of HLA DR3/DQ2 Transgenic Mice: A Potential Humanized Animal Model for Autoimmune Disease Studies", Eur. J. Immunol. 33:172-182 (2003).

McKenzie S.E., "Humanized Mouse Models of FcR Clearance in Immune Platelet Disorders", Blood Reviews 16-3-5 (2002).

Madsen L.S. et al., "A Humanized Model for Multiple Sclerosis Using HLA-DR2 and a Human T-Cell Receptor", Nature Genetics 23:343-347 (Nov. 1999).

Fung-Leung W-P et al., "Transgenic Mice Expressing the Human High-Affinity Immunoglobulin (Ig) E Receptor Alpha Chain Respond to Human IgE in Mast Cell Degranulation and in Allergic Reactions", J. Exp. Med. 183:49-56 (Jan. 1996).

Letter from Frank C. Eisenschenk of Saliwanchik, Lloyd & Eisenchenk dated Apr. 24, 2018.

Declaration of Dr. Adam Stoten with accompanying exhibits (Apr. 24, 2018).

Declaration of Dr. Simon Davis with accompanying exhibits (Apr. 24, 2018).

Brevini T.A.L. et al., "No Shortcuts to Pig Embryonic Stem Cells," Theriogenology 74:544-550 (2010).

Cao S. et al., "Isolation and Culture of Primary Bovine Embryonic Stem Cell Colonies by a Novel Method", Journal of Experimental Zoology 311A:368-376 (2009).

Dennis, Jr. M.B., "Welfare Issues of Genetically Modified Animals", ILAR Journal 43(2):100-109 (2002).

Hofker M.H. et al., "Transgenic Mouse Methods and Protocols", Methods in Molecular Biology 209:51-67 (2002-2003).

Houdebine L-M, "Methods to Generate Transgenic Animals", Genetic Engineering in Livestock, New Applications and Interdisciplinary Perspectives, Engelhard M. et al., XVI, 1 46, p. 8, illu. pp. 31-47 (2009).

Paris D.B.B.P. et al., "Equine Embryos and Embryonic Stem Cells: Defining Reliable Markers of Pluripotency", Theriogenology 74:516-524 (2010).

Rybchin V.N., "Fundamentals of Genetic Engineering", Textbook for High Schools, Saint-Petersburg, Publishing House SPbSTU 522:411-413 (2002).

Zhou H. et al., "Developing tTA Transgenic Rats for Inducible and Reversible Gene Expression", International Journal of Biological Sciences 5(2):171-181 (2009).

Russian Office Action dated Dec. 25, 2018 received in Russian Patent Application No. 2016149434, together with an English-language translation.

Chinese Office Action and Search Report dated Mar. 8, 2019 received in Chinese Application No. 201580033075.2, together with an English-language translation.

Akkaya B., "Modulation of the PD-1 Pathway by Inhibitory Antibody Superagonists", The British Library-etheses online service (ETHOS), ETHOS ID: uk.bl.ethos.60015 (2012) (title page, pp. i, iii-vi, 64-69 and 131-140).

Web Page of ETHOS with the bibliographic information (URL:https://ethos.bl.uk/OrderDetails.do?uin=uk.bl.ethos.600015) (2012).

Web Page of Oxford University Research Archive with the bibliographic information (URL:https://ora.ox.ac.uk/objects/uuid:1c97e755-e61d-4d55-8b20-b2546c826eee) (2012).

Immunology, vol. 135, Supp. Suppl. 1, pp. 181, Content on the Embase database of Abstract No. 100 (Dec. 2011).

Immunology, vol. 135, Suppl. Suppl. 1, pp. 44, Content on the Embase database of Abstract No. 80 (Dec. 2011).

Harari D. et al., "Bridging the Species Divide: Transgenic Mice Humanized for Type-I Interferon Response", PLoS One 9(1):e84259, XP055553720, DOI:10.1371/journal.pone.0084259 (Jan. 9, 2014).

European Patent Office Telephone Minute dated May 21, 2019 received in European Patent Application No. 15738177.3.

Japanese Notice of Reasons for Rejection dated May 16, 2019 received in Japanese Application No. 2016-573923, together with an English-language translation.

* cited by examiner

Figure 8

Mouse Pdcd1 mRNA (NM_008798.2)
TGAGCAGCGGGGAGGAGGAAGAGGAGACTGCTACTGAAGGCGACACTGCCAGGGGCT
CTGGGCATGTGGGTCCGGCAGGTACCCTGGTCATTCACTTGGGCTGTGCTGCAGT
TGAGCTGGCAATCAGGGTGGCTTCTAGAGGTCCCCAATGGGCCCTGGAGGTCCCT
CACCTTCTACCCAGCCTGGCTCACAGTGTCAGAGGGAGCAAATGCCACCTTCACC
TGCAGCTTGTCCAACTGGTCGGAGGATCTTATGCTGAACTGGAACCGCCTGAGTC
CCAGCAACCAGACTGAAAAACAGGCCGCCTTCTGTAATGGTTTGAGCCAACCCGT
CCAGGATGCCCGCTTCCAGATCATACAGCTGCCCAACAGGCATGACTTCCACATG
AACATCCTTGACACACGGCGCAATGACAGTGGCATCTACCTCTGTGGGGCCATCT
CCCTGCACCCCAAGGCAAAAATCGAGGAGAGCCCTGGAGCAGAGCTCGTGGTAA
CAGAGAGAATCCTGGAGACCTCAACAAGATATCCCAGCCCCTCGCCCAAACCAGA
AGGCCGGTTTCAAGGCATGGTCATTGGTATCATGAGTGCCCTAGTGGGTATCCCT
GTATTGCTGCTGCTGGCCTGGGCCCTAGCTGTCTTCTGCTCAACAAGTATGTCAG
AGGCCAGAGGAGCTGGAAGCAAGGACGACACTCTGAAGGAGGAGCCTTCAGCAG
CACCTGTCCCTAGTGTGGCCTATGAGGAGCTGGACTTCCAGGGACGAGAGAAGAC
ACCAGAGCTCCCTACCGCCTGTGTGCACACAGAATATGCCACCATTGTCTTCACT
GAAGGGCTGGGTGCCTCGGCCATGGGACGTAGGGGCTCAGCTGATGGCCTGCAG
GGTCCTCGGCCTCCAAGACATGAGGATGGACATTGTTCTTGGCCTCTTTGACCAG
ATTCTTCAGCCATTAGCATGCTGCAGACCCTCCACAGAGAGCACCGGTCCGTCCCTCAG
TCAAGAGGAGCATGCAGGCTACAGTTCAGCCAAGGCTCCCAGGGTCTGAGCTAGCTGG
AGTGACAGCCCAGCGCCTGCACCAATTCCAGCACATGCACTGTTGAGTGAGAGCTCAC
TTCAGGTTTACCACAAGCTGGGAGCAGCAGGCTTCCCGGTTTCCTATTGTCACAAGGTG
CAGAGCTGGGGCCTAAGCCTATGTCTCCTGAATCCTACTGTTGGGCACTTCTAGGGACT
TGAGACACTATAGCCAATGGCCTCTGTGGGTTCTGTGCCTGGAAATGGAGAGATCTGA
GTACAGCCTGCTTTGAATGGCCCTGTGAGGCAACCCCAAAGCAAGGGGGTCCAGGTAT
ACTATGGGCCCAGCACCTAAAGCCACCCTTGGGAGATGATACTCAGGTGGGAAATTCG
TAGACTGGGGGACTGAACCAATCCCAAGATCTGGAAAAGTTTTGATGAAGACTTGAAA
AGCTCCTAGCTTCGGGGGTCTGGGAAGCATGAGCACTTACCAGGCAAAAGCTCCGTGA
GCGTATCTGCTGTCCTTCTGCATGCCCAGGTACCTCAGTTTTTTTCAACAGCAAGGAAA
CTAGGGCAATAAAGGGAACCAGCAGAGCTAGAGCCACCCACACATCCAGGGGGCACT
TGACTCTCCCTACTCCTCCTAGGAACCAAAAGGACAAAGTCCATGTTGACAGCAGGGA
AGGAAAGGGGGATATAACCTTGACGCAAACCAACACTGGGGTGTTAGAATCTCCTCAT
TCACTCTGTCCTGGAGTTGGGTTCTGGCTCTCCTTCACACCTAGGACTCTGAAATGAGC
AAGCACTTCAGACAGTCAGGGTAGCAAGAGTCTAGCTGTCTGGTGGGCACCCAAAATG
ACCAGGGCTTAAGTCCCTTTCCTTTGGTTTAAGCCCGTTATAATTAAATGGTACCAAAA
GCTTTAAAAAAAAAAAAAAAAAAAAAAAAAAAAAAAAAAAAAAAAAAA (SEQ ID NO:1)

Mouse PD-1 amino acid (Q02242)
MWVRQVPWSFTWAVLQLSWQSGWLLEVPNG(PWRSLTFYPAWLTVSEGANATFTCSL
SNWSEDLMLNWNRLSPSNQTEKQAAFCNGLSQPVQDARFQIIQLPNRHDFHMNILDT
RRNDSGIYLCGAISLHPKAKIEESPG)AELVVTERILETSTRYPSPSPKPEGRFQGMVIGI
MSALVGIPVLLLLAWALA*VFCSTSMSEARGAGSKDDTLKEEPSAAPVPSVAYEELDFQGREKT
PELPTACVHTEYATIVFTEGLGASAMGRRGSADGLQGPRPPRHEDGHCSWPL* (SEQ ID NO:2)

Figure 8, continued...

Human Pdcd1 mRNA (NM_005018.2)
AGTTTCCCTTCCGCTCACCTCCGCCTGAGCAGTGGAGAAGGCGGCACTCTGGTGGGGCT
GCTCCAGGCATGCAGATCCCACAGGCGCCCTGGCCAGTCGTCTGGGCGGTGCTAC
AACTGGGCTGGCGGCCAGGATGGTTCTTAGACTCCCCAGACAGGCCCTGGAACCC
CCCCACCTTCTCCCCAGCCCTGCTCGTGGTGACCGAAGGGGACAACGCCACCTTC
ACCTGCAGCTTCTCCAACACATCGGAGAGCTTCGTGCTAAACTGGTACCGCATGA
GCCCCAGCAACCAGACGGACAAGCTGGCCGCCTTCCCCGAGGACCGCAGCCAGC
CCGGCCAGGACTGCCGCTTCCGTGTCACACAACTGCCCAACGGGCGTGACTTCCA
CATGAGCGTGGTCAGGGCCCGGCGCAATGACAGCGGCACCTACCTCTGTGGGGC
CATCTCCCTGGCCCCCAAGGCGCAGATCAAAGAGAGCCTGCGGGCAGAGCTCAG
GGTGACAGAGAGAAGGGCAGAAGTGCCCACAGCCCACCCCAGCCCCTCACCCAG
GCCAGCCGGCCAGTTCCAAACCCTGGTGGTTGGTGTCGTGGGCGGCCTGCTGGG
CAGCCTGGTGCTGCTAGTCTGGGTCCTGGCCGTCATCTGCTCCCGGGCCGCACGA
GGGACAATAGGAGCCAGGCGCACCGGCCAGCCCCTGAAGGAGGACCCCTCAGCC
GTGCCTGTGTTCTCTGTGGACTATGGGGAGCTGGATTTCCAGTGGCGAGAGAAGA
CCCCGGAGCCCCCCGTGCCCTGTGTCCCTGAGCAGACGGAGTATGCCACCATTGT
CTTTCCTAGCGGAATGGGCACCTCATCCCCCGCCCGCAGGGGCTCAGCTGACGGC
CCTCGGAGTGCCCAGCCACTGAGGCCTGAGGATGGACACTGCTCTTGGCCCCTCT
GACCGGCTTCCTTGGCCACCAGTGTTCTGCAGACCCTCCACCATGAGCCCGGGTCAGCG
CATTTCCTCAGGAGAAGCAGGCAGGGTGCAGGCCATTGCAGGCCGTCCAGGGGCTGAG
CTGCCTGGGGGCGACCGGGGCTCCAGCCTGCACCTGCACCAGGCACAGCCCCACCACA
GGACTCATGTCTCAATGCCCACAGTGAGCCCAGGCAGCAGGTGTCACCGTCCCCTACA
GGGAGGGCCAGATGCAGTCACTGCTTCAGGTCCTGCCAGCACAGAGCTGCCTGCGTCC
AGCTCCCTGAATCTCTGCTGCTGCTGCTGCTGCTGCTGCTGCTGCCTGCGGCCCGGGGC
TGAAGGCGCCGTGGCCCTGCCTGACGCCCCGGAGCCTCCTGCCTGAACTTGGGGGCTG
GTTGGAGATGGCCTTGGAGCAGCCAAGGTGCCCCTGGCAGTGGCATCCCGAAACGCCC
TGGACGCAGGGCCCAAGACTGGGCACAGGAGTGGGAGGTACATGGGGCTGGGGACTC
CCCAGGAGTTATCTGCTCCCTGCAGGCCTAGAGAAGTTTCAGGGAAGGTCAGAAGAGC
TCCTGGCTGTGGTGGGCAGGGCAGGAAACCCCTCCACCTTTACACATGCCCAGGCAGC
ACCTCAGGCCCTTTGTGGGGCAGGGAAGCTGAGGCAGTAAGCGGGCAGGCAGAGCTG
GAGGCCTTTCAGGCCCAGCCAGCACTCTGGCCTCCTGCCGCCGCATTCCACCCCAGCCC
CTCACACCACTCGGGAGAGGGACATCCTACGGTCCCAAGGTCAGGAGGGCAGGGCTGG
GGTTGACTCAGGCCCCTCCCAGCTGTGGCCACCTGGGTGTTGGGAGGGCAGAAGTGCA
GGCACCTAGGGCCCCCCATGTGCCCACCCTGGGAGCTCTCCTTGGAACCCATTCCTGAA
ATTATTTAAAGGGGTTGGCCGGGCTCCCACCAGGGCCTGGGTGGGAAGGTACAGGCGT
TCCCCCGGGGCCTAGTACCCCCGCCGTGGCCTATCCACTCCTCACATCCACACACTGCA
CCCCCACTCCTGGGGCAGGGCCACCAGCATCCAGGCGGCCAGCAGGCACCTGAGTGGC
TGGGACAAGGGATCCCCCTTCCCTGTGGTTCTATTATATTATAATTATAATTAAATATG
AGAGCATGCTAAGGAAAA (SEQ ID NO:3)

Figure 8, continued...

Human PD-1 amino acid (Q15116)
MQIPQAPWPVVWAVLQLGWRPGWFLDSPDRPWNP(PTFSPALLVVTEGDNATFTCSFS
NTSESFVLNWYRMSPSNQTDKLAAFPEDRSQPGQDCRFRVTQLPNGRDFHMSVVRAR
RNDSGTYLCGAISLAPKAQIKESLRAELRVT)ERRAEVPTAHPSPSPRPAGQFQTLVVG
VVGGLLGSLVLLVWVLAV*ICSRAARGTIGARRTGQPLKEDPSAVPVFSVDYGELDFQWREKTP
EPPVPCVPEQTEYATIVFPSGMGTSSPARRGSADGPRSAQPLRPEDGHCSWPL* (SEQ ID NO:4)

Humanized Pdcd1 mRNA
TGAGCAGCGGGGAGGAGGAAGAGGAGACTGCTACTGAAGGCGACACTGCCAGGGGCT
CTGGGCATGTGGGTCCGGCAGGTACCCTGGTCATTCACTTGGGCTGTGCTGCAGT
TGAGCTGGCAATCAGGGTGGCTTCTAG(ACTCCCCAGACAGGCCCTGGAACCCCC
CCACCTTCTCCCCAGCCCTGCTCGTGGTGACCGAAGGGGACAACGCCACCTTCAC
CTGCAGCTTCTCCAACACATCGGAGAGCTTCGTGCTAAACTGGTACCGCATGAGC
CCCAGCAACCAGACGGACAAGCTGGCCGCCTTCCCCGAGGACCGCAGCCAGCCC
GGCCAGGACTGCCGCTTCCGTGTCACACAACTGCCCAACGGGCGTGACTTCCACA
TGAGCGTGGTCAGGGCCCGGCGCAATGACAGCGGCACCTACCTCTGTGGGGCCA
TCTCCCTGGCCCCCAAGGCGCAGATCAAAGAGAGCCTGCGGGCAGAGCTCAGGG
TGACAGAGAGAAGGGCAGAAGTGCCCACAGCCCACCCCAGCCCCTCACCCAGGC
CAGCCGGCCAGTTCCAAACCCTG)GTCATTGGTATCATGAGTGCCCTAGTGGGTAT
CCCTGTATTGCTGCTGCTGGCCTGGGCCCTAGCTGTCTTCTGCTCAACAAGTATG
TCAGAGGCCAGAGGAGCTGGAAGCAAGGACGACACTCTGAAGGAGGAGCCTTCA
GCAGCACCTGTCCCTAGTGTGGCCTATGAGGAGCTGGACTTCCAGGGACGAGAG
AAGACACCAGAGCTCCCTACCGCCTGTGTGCACACAGAATATGCCACCATTGTCT
TCACTGAAGGGCTGGGTGCCTCGGCCATGGGACGTAGGGGCTCAGCTGATGGCC
TGCAGGGTCCTCGGCCTCCAAGACATGAGGATGGACATTGTTCTTGGCCTCTTTG
ACCAGATTCTTCAGCCATTAGCATGCTGCAGACCCTCCACAGAGAGCACCGGTCCGTCC
CTCAGTCAAGAGGAGCATGCAGGCTACAGTTCAGCCAAGGCTCCCAGGGTCTGAGCTA
GCTGGAGTGACAGCCCAGCGCCTGCACCAATTCCAGCACATGCACTGTTGAGTGAGAG
CTCACTTCAGGTTTACCACAAGCTGGGAGCAGCAGGCTTCCCGGTTTCCTATTGTCACA
AGGTGCAGAGCTGGGGCCTAAGCCTATGTCTCCTGAATCCTACTGTTGGGCACTTCTAG
GGACTTGAGACACTATAGCCAATGGCCTCTGTGGGTTCTGTGCCTGGAAATGGAGAGA
TCTGAGTACAGCCTGCTTTGAATGGCCCTGTGAGGCAACCCCAAAGCAAGGGGGTCCA
GGTATACTATGGGCCCAGCACCTAAAGCCACCCTTGGGAGATGATACTCAGGTGGGAA
ATTCGTAGACTGGGGGACTGAACCAATCCCAAGATCTGGAAAAGTTTTGATGAAGACT
TGAAAAGCTCCTAGCTTCGGGGGTCTGGGAAGCATGAGCACTTACCAGGCAAAAGCTC
CGTGAGCGTATCTGCTGTCCTTCTGCATGCCCAGGTACCTCAGTTTTTTTCAACAGCAA
GGAAACTAGGGCAATAAAGGGAACCAGCAGAGCTAGAGCCACCCACACATCCAGGGG
GCACTTGACTCTCCCTACTCCTCCTAGGAACCAAAAGGACAAAGTCCATGTTGACAGC
AGGGAAGGAAAGGGGGATATAACCTTGACGCAAACCAACACTGGGGTGTTAGAATCT
CCTCATTCACTCTGTCCTGGAGTTGGGTTCTGGCTCTCCTTCACACCTAGGACTCTGAAA
TGAGCAAGCACTTCAGACAGTCAGGGTAGCAAGAGTCTAGCTGTCTGGTGGGCACCCA
AAATGACCAGGGCTTAAGTCCCTTTCCTTTGGTTTAAGCCCGTTATAATTAAATGGTAC
CAAAAGCTTTAAAAAAAAAAAAAAAAAAAAAAAAAAAAAAAAAAAAAAAAAAAAA
(SEQ ID NO:5)

Figure 8, continued...

Humanized PD-1 amino acid
MWVRQVPWSFTWAVLQLSWQSGWLLDSPDRPWNP(PTFSPALLVVTEGDNATFTCSFS
NTSESFVLNWYRMSPSNQTDKLAAFPEDRSQPGQDCRFRVTQLPNGRDFHMSVVRAR
RNDSGTYLCGAISLAPKAQIKESLRAELRVT)ERRAEVPTAHPSPSPRPAGQFQTLVIGI
MSALVGIPVLLLLAWAL*AVFCSTSMSEARGAGSKDDTLKEEPSAAPVPSVAYEELDFQGREKT
PELPTACVHTEYATIVFTEGLGASAMGRRGSADGLQGPRPPRHEDGHCSWPL* (SEQ ID NO:6)

Human 883 bp DNA fragment
AAGAGGCTCTGCAGTGGAGGCCAGTGCCCATCCCCGGGTGGCAGAGGCCCCAGCAGA
GACTTCTCAATGACATTCCAGCTGGGGTGGCCCTTCCAGAGCCCTTGCTGCCCGAGGGA
TGTGAGCAGGTGGCCGGGGAGGCTTTGTGGGGCCACCCAGCCCCTTCCTCACCTCTCTC
CATCTCTCAGACTCCCCAGACAGGCCCTGGAACCCCCCCACCTTCTCCCCAGCCCTGCT
CGTGGTGACCGAAGGGGACAACGCCACCTTCACCTGCAGCTTCTCCAACACATCGGAG
AGCTTCGTGCTAAACTGGTACCGCATGAGCCCCAGCAACCAGACGGACAAGCTGGCCG
CCTTCCCCGAGGACCGCAGCCAGCCCGGCCAGGACTGCCGCTTCCGTGTCACACAACT
GCCCAACGGGCGTGACTTCCACATGAGCGTGGTCAGGGCCCGGCGCAATGACAGCGGC
ACCTACCTCTGTGGGGCCATCTCCCTGGCCCCCAAGGCGCAGATCAAAGAGAGCCTGC
GGGCAGAGCTCAGGGTGACAGGTGCGGCCTCGGAGGCCCCGGGGCAGGGGTGAGCTG
AGCCGGTCCTGGGGTGGGTGTCCCTCCTGCACAGGATCAGGAGCTCCAGGGTCGTAG
GGCAGGGACCCCCCAGCTCCAGTCCAGGGCTCTGTCCTGCACCTGGGGAATGGTGACC
GGCATCTCTGTCCTCTAGCTCTGGAAGCACCCCAGCCCCTCTAGTCTGCCCTCACCCCT
GACCCTGACCCTCCACCCTGACCCCGTCCTAACCCCTGACCTTTGTGCCCTTCCAGAGA
GAAGGGCAGAAGTGCCCACAGCCCACCCCAGCCCCTCACCCAGGCCAGCCGGCCAGTT
CCAAACCCTG (SEQ ID NO:23)

SEQUENCE LISTING

```
<160> NUMBER OF SEQ ID NOS: 29

<210> SEQ ID NO 1
<211> LENGTH: 1972
<212> TYPE: DNA
<213> ORGANISM: Mus musculus

<400> SEQUENCE: 1
tgagcagcgg ggaggaggaa gaggagactg ctactgaagg cgacactgcc aggggctctg      60
ggcatgtggg tccggcaggt accctggtca ttcacttggg ctgtgctgca gttgagctgg     120
caatcagggt ggcttctaga ggtccccaat gggccctgga ggtccctcac cttctaccca     180
gcctggctca cagtgtcaga gggagcaaat gccaccttca cctgcagctt gtccaactgg     240
```

```
tcggaggatc ttatgctgaa ctggaaccgc ctgagtccca gcaaccagac tgaaaaacag      300
gccgccttct gtaatggttt gagccaaccc gtccaggatg cccgcttcca gatcatacag      360
ctgcccaaca ggcatgactt ccacatgaac atccttgaca cacggcgcaa tgacagtggc      420
atctacctct gtggggccat ctccctgcac cccaaggcaa aaatcgagga gagccctgga      480
gcagagctcg tggtaacaga gagaatcctg gagacctcaa caagatatcc cagcccctcg      540
cccaaaccag aaggccggtt tcaaggcatg gtcattggta tcatgagtgc cctagtgggt      600
atccctgtat tgctgctgct ggcctgggcc ctagctgtct tctgctcaac aagtatgtca      660
gaggccagag gagctggaag caaggacgac actctgaagg aggagccttc agcagcacct      720
gtccctagtg tggcctatga ggagctggac ttccagggac gagagaagac accagagctc      780
cctaccgcct gtgtgcacac agaatatgcc accattgtct tcactgaagg ctgggtgcc      840 tcggccatgg gacgtagggg ctcagctgat ggcctgcagg gtcctcggcc tccaagacat      900
gaggatggac attgttcttg gcctctttga ccagattctt cagccattag catgctgcag      960
accctccaca gagagcaccg gtccgtccct cagtcaagag gagcatgcag gctacagttc     1020
agccaaggct cccagggtct gagctagctg gagtgacagc ccagcgcctg caccaattcc     1080
agcacatgca ctgttgagtg agagctcact tcaggtttac cacaagctgg gagcagcagg     1140
cttcccggtt tcctattgtc acaaggtgca gagctgggc ctaagcctat gtctcctgaa     1200
tcctactgtt gggcacttct agggacttga gacactatag ccaatggcct ctgtgggttc     1260
tgtgcctgga atggagaga tctgagtaca gcctgctttg aatggccctg tgaggcaacc     1320
ccaaagcaag ggggtccagg tatactatgg gcccagcacc taaagccacc cttgggagat     1380
gatactcagg tgggaaattc gtagactggg ggactgaacc aatcccaaga tctggaaaag     1440
ttttgatgaa gacttgaaaa gctcctagct tcggggtct gggaagcatg agcacttacc     1500
aggcaaaagc tccgtgagcg tatctgctgt ccttctgcat gcccaggtac ctcagttttt     1560
ttcaacagca aggaaactag gcaataaag ggaaccagca gagctagagc cacccacaca     1620
tccagggggc acttgactct ccctactcct cctaggaacc aaaaggacaa agtccatgtt     1680
gacagcaggg aaggaaaggg ggatataacc ttgacgcaaa ccaacactgg ggtgttagaa     1740
tctcctcatt cactctgtcc tggagttggg ttctggctct ccttcacacc taggactctg     1800
aaatgagcaa gcacttcaga cagtcagggt agcaagagtc tagctgtctg gtgggcaccc     1860
aaaatgacca gggcttaagt ccctttcctt tggtttaagc ccgttataat taaatggtac     1920
caaaagcttt aaaaaaaaaa aaaaaaaaaa aaaaaaaaaa aaaaaaaaaa aa              1972
```

<210> SEQ ID NO 2
<211> LENGTH: 288
<212> TYPE: PRT
<213> ORGANISM: Mus musculus

<400> SEQUENCE: 2

```
Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60
```

| | | | | | | | | | | | | | | |
|---|---|---|---|---|---|---|---|---|---|---|---|---|---|---|
| Leu | Asn | Trp | Asn | Arg | Leu | Ser | Pro | Ser | Asn | Thr | Glu | Lys | Gln | Ala |
| 65 | | | | 70 | | | | 75 | | | | | 80 | |
| Ala | Phe | Cys | Asn | Gly | Leu | Ser | Gln | Pro | Val | Gln | Asp | Ala | Arg | Phe | Gln |
| | | | | 85 | | | | 90 | | | | | 95 | | |
| Ile | Ile | Gln | Leu | Pro | Asn | Arg | His | Asp | Phe | His | Met | Asn | Ile | Leu | Asp |
| | | | 100 | | | | | 105 | | | | | 110 | | |
| Thr | Arg | Arg | Asn | Asp | Ser | Gly | Ile | Tyr | Leu | Cys | Gly | Ala | Ile | Ser | Leu |
| | | 115 | | | | | 120 | | | | | 125 | | | |
| His | Pro | Lys | Ala | Lys | Ile | Glu | Glu | Ser | Pro | Gly | Ala | Glu | Leu | Val | Val |
| | 130 | | | | | 135 | | | | | 140 | | | | |
| Thr | Glu | Arg | Ile | Leu | Glu | Thr | Ser | Thr | Arg | Tyr | Pro | Ser | Pro | Ser | Pro |
| 145 | | | | | 150 | | | | | 155 | | | | | 160 |
| Lys | Pro | Glu | Gly | Arg | Phe | Gln | Gly | Met | Val | Ile | Gly | Ile | Met | Ser | Ala |
| | | | | 165 | | | | 170 | | | | | 175 | | |
| Leu | Val | Gly | Ile | Pro | Val | Leu | Leu | Leu | Leu | Ala | Trp | Ala | Leu | Ala | Val |
| | | | 180 | | | | | 185 | | | | | 190 | | |
| Phe | Cys | Ser | Thr | Ser | Met | Ser | Glu | Ala | Arg | Gly | Ala | Gly | Ser | Lys | Asp |
| | | 195 | | | | | 200 | | | | | 205 | | | |
| Asp | Thr | Leu | Lys | Glu | Glu | Pro | Ser | Ala | Ala | Pro | Val | Pro | Ser | Val | Ala |
| | 210 | | | | | 215 | | | | | 220 | | | | |
| Tyr | Glu | Glu | Leu | Asp | Phe | Gln | Gly | Arg | Glu | Lys | Thr | Pro | Glu | Leu | Pro |
| 225 | | | | | 230 | | | | | 235 | | | | | 240 |
| Thr | Ala | Cys | Val | His | Thr | Glu | Tyr | Ala | Thr | Ile | Val | Phe | Thr | Glu | Gly |
| | | | | 245 | | | | 250 | | | | | 255 | | |
| Leu | Gly | Ala | Ser | Ala | Met | Gly | Arg | Arg | Gly | Ser | Ala | Asp | Gly | Leu | Gln |
| | | | 260 | | | | | 265 | | | | | 270 | | |
| Gly | Pro | Arg | Pro | Pro | Arg | His | Glu | Asp | Gly | His | Cys | Ser | Trp | Pro | Leu |
| | | 275 | | | | | 280 | | | | | 285 | | | |

<210> SEQ ID NO 3
<211> LENGTH: 2115
<212> TYPE: DNA
<213> ORGANISM: Homo sapiens

<400> SEQUENCE: 3

```
agtttccctt ccgctcacct ccgcctgagc agtggagaag gcggcactct ggtgggctg      60 ctccaggcat gcagatccca caggcgccct ggccagtcgt ctgggcggtg ctacaactgg     120
gctggcggcc aggatggttc ttagactccc agacaggcc ctggaacccc ccaccttct      180 ccccagcccc gctcgtggtg accgaagggg acaacgccac cttcacctgc agcttctcca     240
acacatcgga gagcttcgtg ctaaactggt accgcatgag ccccagcaac agacggaca     300 agctggccgc cttccccgag gaccgcagcc agcccggcca ggactgccgc ttccgtgtca     360
cacaactgcc caacgggcgt gacttccaca tgagcgtggt cagggcccgg cgcaatgaca     420
gcggcaccta cctctgtggg gccatctccc tggccccaa ggcgcagatc aaagagagcc      480
tgcgggcaga gctcagggtg acagagagaa gggcagaagt gccacagcc cacccagcc      540 cctcacccag gccagccggc cagttccaaa ccctggtggt tggtgtcgtg ggcggcctgc     600
tgggcagcct ggtgctgcta gtctgggtcc tggccgtcat ctgctcccgg gccgcacgag     660
ggacaatagg agccaggcgc accggccagc ccctgaagga ggacccctca gccgtgcctg     720
tgttctctgt ggactatggg gagctggatt ccagtggcg agagaagacc ccggagcccc      780
ccgtgccctg tgtccctgag cagacggagt atgccaccat tgtctttcct agcggaatgg     840
gcacctcatc ccccgcccgc aggggctcag ctgacggcc tcggagtgcc cagccactga     900
```

-continued

```
ggcctgagga tggacactgc tcttggcccc tctgaccggc ttccttggcc accagtgttc    960
tgcagaccct ccaccatgag cccgggtcag cgcatttcct caggagaagc aggcagggtg   1020
caggccattg caggccgtcc aggggctgag ctgcctgggg gcgaccgggg ctccagcctg   1080
cacctgcacc aggcacagcc ccaccacagg actcatgtct caatgcccac agtgagccca   1140
ggcagcaggt gtcaccgtcc cctacaggga gggccagatg cagtcactgc ttcaggtcct   1200
gccagcacag agctgcctgc gtccagctcc ctgaatctct gctgctgctg ctgctgctgc   1260
tgctgctgcc tgcggcccgg ggctgaaggc gccgtggccc tgcctgacgc cccggagcct   1320
cctgcctgaa cttgggggct ggttggagat ggccttggag cagccaaggt gcccctggca   1380
gtggcatccc gaaacgccct ggacgcaggg cccaagactg gcacaggag  tgggaggtac   1440 atggggctgg ggactcccca ggagttatct gctccctgca ggcctagaga agtttcaggg   1500
aaggtcagaa gagctcctgg ctgtggtggg cagggcagga accccctcca cctttacaca   1560
tgcccaggca gcacctcagg cccttttgtgg ggcaggaag  ctgaggcagt aagcgggcag   1620
gcagagctgg aggcctttca ggcccagcca gcactctggc ctcctgccgc cgcattccac   1680
cccagcccct cacaccactc gggagaggga catcctacgg tcccaaggtc aggagggcag   1740
ggctggggtt gactcaggcc cctcccagct gtggccacct gggtgttggg agggcagaag   1800
tgcaggcacc tagggccccc catgtgccca ccctgggagc tctccttgga acccattcct   1860
gaaattattt aaaggggttg gccgggctcc caccagggcc tgggtgggaa ggtacaggcg   1920
ttcccccggg gcctagtacc cccgccgtgg cctatccact cctcacatcc acacactgca   1980
cccccactcc tggggcaggg ccaccagcat ccaggcggcc agcaggcacc tgagtggctg   2040
ggacaaggga tccccttcc ctgtggttct attatattat aattataatt aaatatgaga   2100
gcatgctaag gaaaa                                                   2115
```

<210> SEQ ID NO 4
<211> LENGTH: 288
<212> TYPE: PRT
<213> ORGANISM: Homo sapiens

<400> SEQUENCE: 4

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
```

```
              145                 150                 155                 160
Arg Pro Ala Gly Gln Phe Gln Thr Leu Val Val Gly Val Val Gly
                165                 170                 175
Leu Leu Gly Ser Leu Val Leu Leu Val Trp Val Leu Ala Val Ile Cys
            180                 185                 190
Ser Arg Ala Ala Arg Gly Thr Ile Gly Ala Arg Arg Thr Gly Gln Pro
            195                 200                 205
Leu Lys Glu Asp Pro Ser Ala Val Pro Val Phe Ser Val Asp Tyr Gly
    210                 215                 220
Glu Leu Asp Phe Gln Trp Arg Glu Lys Thr Pro Glu Pro Pro Val Pro
225                 230                 235                 240
Cys Val Pro Glu Gln Thr Glu Tyr Ala Thr Ile Val Phe Pro Ser Gly
                245                 250                 255
Met Gly Thr Ser Ser Pro Ala Arg Arg Gly Ser Ala Asp Gly Pro Arg
            260                 265                 270
Ser Ala Gln Pro Leu Arg Pro Glu Asp Gly His Cys Ser Trp Pro Leu
            275                 280                 285

<210> SEQ ID NO 5
<211> LENGTH: 1972
<212> TYPE: DNA
<213> ORGANISM: Artificial Sequence
<220> FEATURE:
<223> OTHER INFORMATION: Humanized Pdcd1

<400> SEQUENCE: 5
tgagcagcgg ggaggaggaa gaggagactg ctactgaagg cgacactgcc aggggctctg      60
ggcatgtggg tccggcaggt accctggtca ttcacttggg ctgtgctgca gttgagctgg     120
caatcagggt ggcttctaga ctccccagac aggccctgga accccccac  cttctcccca     180
gccctgctcg tggtgaccga aggggacaac gccaccttca cctgcagctt ctccaacaca     240
tcggagagct tcgtgctaaa ctggtaccgc atgagcccca gcaaccagac ggacaagctg     300
gccgccttcc ccgaggaccg cagccagccc ggccaggact ccgcttccg  tgtcacacaa     360
ctgcccaacg gcgtgacttt ccacatgagc gtggtcaggg cccggcgcaa tgacagcggc     420
acctacctct gtggggccat ctccctggcc ccaaggcgc  agatcaaaga gagcctgcgg     480
gcagagctca gggtgacaga gagaagggca gaagtgccca gcccacccc  agcccctca    540
cccaggccag ccggccagtt ccaaaccctg gtcattggta tcatgagtgc cctagtgggt     600
atccctgtat gctgctgct  ggcctgggcc ctagctgtct tctgctcaac aagtatgtca     660
gaggccagag gagctggaag caaggacgac actctgaagg aggagccttc agcagcacct     720
gtccctagtg tggcctatga ggagctggac ttcagggac  gagagaagac accagagctc     780
cctaccgcct gtgtgcacac agaatatgcc accattgtct tcactgaagg ctgggtgcc     840
tcggccatgg gacgtagggg ctcagctgat ggcctgcagg gtcctcggcc tccaagacat     900
gaggatggac attgttcttg gcctctttga ccagattctt cagccattag catgctgcag     960
accctccaca gagagcaccg gtccgtccct cagtcaagag gagcatgcag gctacagttc    1020
agccaaggct cccagggtct gagctagctg gagtgacagc ccagcgcctg caccaattcc    1080
agcacatgca ctgttgagtg agagctcact tcaggtttac cacaagctgg gagcagcagg    1140
cttcccggtt tcctattgtc acaaggtgca gagctggggc ctaagcctat gtctcctgaa    1200
tcctactgtt gggcacttct agggacttga gacactatag ccaatggcct ctgtgggttc    1260
tgtgcctgga aatggagaga tctgagtaca gcctgctttg aatggccctg tgaggcaacc    1320
```

```
ccaaagcaag ggggtccagg tatactatgg gcccagcacc taaagccacc cttgggagat    1380
gatactcagg tgggaaattc gtagactggg ggactgaacc aatcccaaga tctggaaaag    1440
ttttgatgaa gacttgaaaa gctcctagct tcgggggtct gggaagcatg agcacttacc    1500
aggcaaaagc tccgtgagcg tatctgctgt ccttctgcat gcccaggtac ctcagttttt    1560
ttcaacagca aggaaactag ggcaataaag ggaaccagca gagctagagc acccacaca    1620 tccaggggc acttgactct ccctactcct cctaggaacc aaaaggacaa agtccatgtt    1680
gacagcaggg aaggaaggg ggatataacc ttgacgcaaa ccaacactgg ggtgttagaa    1740
tctcctcatt cactctgtcc tggagttggg ttctggctct ccttcacacc taggactctg    1800
aaatgagcaa gcacttcaga cagtcagggt agcaagagtc tagctgtctg gtgggcaccc    1860
aaaatgacca gggcttaagt ccctttcctt tggtttaagc ccgttataat taaatggtac    1920
caaaagcttt aaaaaaaaaa aaaaaaaaaa aaaaaaaaaa aaaaaaaaaa aa            1972
```

<210> SEQ ID NO 6
<211> LENGTH: 288
<212> TYPE: PRT
<213> ORGANISM: Artificial Sequence
<220> FEATURE:
<223> OTHER INFORMATION: Humanized PD-1

<400> SEQUENCE: 6

```
Met Trp Val Arg Gln Val Pro Trp Ser Phe Thr Trp Ala Val Leu Gln
1               5                   10                  15

Leu Ser Trp Gln Ser Gly Trp Leu Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Ile Gly Ile Met Ser Ala
                165                 170                 175

Leu Val Gly Ile Pro Val Leu Leu Leu Ala Trp Ala Leu Ala Val
            180                 185                 190

Phe Cys Ser Thr Ser Met Ser Glu Ala Arg Gly Ala Gly Ser Lys Asp
        195                 200                 205

Asp Thr Leu Lys Glu Glu Pro Ser Ala Ala Pro Val Pro Ser Val Ala
    210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
```

```
                    245                 250                 255
Leu Gly Ala Ser Ala Met Gly Arg Arg Gly Ser Ala Asp Gly Leu Gln
            260                 265                 270

Gly Pro Arg Pro Pro Arg His Glu Asp Gly His Cys Ser Trp Pro Leu
        275                 280                 285
```

<210> SEQ ID NO 7
<211> LENGTH: 23
<212> TYPE: DNA
<213> ORGANISM: Artificial Sequence
<220> FEATURE:
<223> OTHER INFORMATION: Synthetic Oligonucleotide: 7106 hTU Forward

<400> SEQUENCE: 7
cccagcagag acttctcaat gac                                        23

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligonucleotide: 7106 hTU Probe

<400> SEQUENCE: 8
tggcccttcc agagcccttg                                            20

<210> SEQ ID NO 9
<211> LENGTH: 18
<212> TYPE: DNA
<213> ORGANISM: Artificial Sequence
<220> FEATURE:
<223> OTHER INFORMATION: Synthetic Oligonucleotide: 7106 hTU Reverse

<400> SEQUENCE: 9
cggccacctg ctcacatc                                              18

<210> SEQ ID NO 10
<211> LENGTH: 21
<212> TYPE: DNA
<213> ORGANISM: Artificial Sequence
<220> FEATURE:
<223> OTHER INFORMATION: Synthetic Oligonucleotide: 7106 hTD Forward

<400> SEQUENCE: 10
ggcatctctg tcctctagct c                                          21

<210> SEQ ID NO 11
<211> LENGTH: 24
<212> TYPE: DNA
<213> ORGANISM: Artificial Sequence
<220> FEATURE:
<223> OTHER INFORMATION: Synthetic Oligonucleotide: 7106 hTD Probe

<400> SEQUENCE: 11
aagcacccca gccctctag tctg                                        24

<210> SEQ ID NO 12
<211> LENGTH: 18
<212> TYPE: DNA
<213> ORGANISM: Artificial Sequence
<220> FEATURE:
<223> OTHER INFORMATION: Synthetic Oligonucleotide: 7106 hTD Reverse

<400> SEQUENCE: 12
gggctgtggg cacttctg                                              18

<210> SEQ ID NO 13
<211> LENGTH: 22
<212> TYPE: DNA
<213> ORGANISM: Artificial Sequence
<220> FEATURE:
<223> OTHER INFORMATION: Synthetic Oligonucleotide: 7106 TU Forward

<400> SEQUENCE: 13
ccttcctcac agctctttgt tc                                          22

<210> SEQ ID NO 14
<211> LENGTH: 25
<212> TYPE: DNA
<213> ORGANISM: Artificial Sequence
<220> FEATURE:
<223> OTHER INFORMATION: Synthetic Oligonucleotide: 7106 TU Probe

<400> SEQUENCE: 14
tctgcatttc agaggtcccc aatgg                                       25

<210> SEQ ID NO 15
<211> LENGTH: 19
<212> TYPE: DNA
<213> ORGANISM: Artificial Sequence
<220> FEATURE:
<223> OTHER INFORMATION: Synthetic Oligonucleotide: 7106 TU Reverse

<400> SEQUENCE: 15
gagccaggct gggtagaag                                              19

<210> SEQ ID NO 16
<211> LENGTH: 25
<212> TYPE: DNA
<213> ORGANISM: Artificial Sequence
<220> FEATURE:
<223> OTHER INFORMATION: Synthetic Oligonucleotide: 7106 TD Forward

<400> SEQUENCE: 16
cggtgtccta gaactctatt ctttg                                       25

<210> SEQ ID NO 17
<211> LENGTH: 27
<212> TYPE: DNA
<213> ORGANISM: Artificial Sequence
<220> FEATURE:
<223> OTHER INFORMATION: Synthetic Oligonucleotide: 7106 TD Probe

<400> SEQUENCE: 17
tcctggagac ctcaacaaga tatccca                                     27

<210> SEQ ID NO 18
<211> LENGTH: 19
<212> TYPE: DNA
<213> ORGANISM: Artificial Sequence
<220> FEATURE:
<223> OTHER INFORMATION: Synthetic Oligonucleotide: 7106 TD Reverse

<400> SEQUENCE: 18
tgaaaccggc cttctggtt                                              19

<210> SEQ ID NO 19
<211> LENGTH: 156
<212> TYPE: DNA
<213> ORGANISM: Artificial Sequence
<220> FEATURE:

<223> OTHER INFORMATION: Synthetic Oligonucleotide

<400> SEQUENCE: 19

```
tcaaaggaca gaatagtagc ctccagaccc taggttcagt tatgctgaag gaagagccct      60
ctcgagataa cttcgtataa tgtatgctat acgaagttat atgcatggcc tccgcgccgg     120
gttttggcgc ctcccgcggg cgcccccctc ctcacg                               156
```

<210> SEQ ID NO 20
<211> LENGTH: 236
<212> TYPE: DNA
<213> ORGANISM: Artificial Sequence
<220> FEATURE:
<223> OTHER INFORMATION: Synthetic Oligonucleotide

<400> SEQUENCE: 20

```
ctggaataac ttcgtataat gtatgctata cgaagttatg ctagtaacta taacggtcct      60
aaggtagcga gctagcaaga ggctctgcag tggaggccag tgcccatccc cgggtggcag     120
aggccccagc agagacttct caatgacatt ccagctgggg tggcccttcc agagcccttg     180
ctgcccgagg gatgtgagca ggtggccggg gaggctttgt ggggccaccc agcccc        236
```

<210> SEQ ID NO 21
<211> LENGTH: 160
<212> TYPE: DNA
<213> ORGANISM: Artificial Sequence
<220> FEATURE:
<223> OTHER INFORMATION: Synthetic Oligonucleotide

<400> SEQUENCE: 21

```
cccttccaga gagaagggca gaagtgccca cagcccaccc cagcccctca cccaggccag      60
ccggccagtt ccaaaccctg gtcattggta tcatgagtgc cctagtgggt atccctgtat     120
tgctgctgct ggcctgggcc ctagctgtct tctgctcaac                           160
```

<210> SEQ ID NO 22
<211> LENGTH: 232
<212> TYPE: DNA
<213> ORGANISM: Artificial Sequence
<220> FEATURE:
<223> OTHER INFORMATION: Synthetic Oligonucleotide

<400> SEQUENCE: 22

```
tcaaaggaca gaatagtagc ctccagaccc taggttcagt tatgctgaag gaagagccct      60
ctcgagataa cttcgtataa tgtatgctat acgaagttat gctagtaact ataacggtcc     120
taaggtagcg agctagcaag aggctctgca gtggaggcca gtgcccatcc ccgggtggca     180
gaggccccag cagagacttc tcaatgacat tccagctggg gtggcccttc ca             232
```

<210> SEQ ID NO 23
<211> LENGTH: 883
<212> TYPE: DNA
<213> ORGANISM: Artificial Sequence
<220> FEATURE:
<223> OTHER INFORMATION: Synthetic Oligonucleotide: Human 883 bp DNA
     fragment

<400> SEQUENCE: 23

```
aagaggctct gcagtggagg ccagtgccca tccccgggtg gcagaggccc cagcagagac      60
ttctcaatga cattccagct ggggtggccc ttccagagcc cttgctgccc gagggatgtg     120
agcaggtggc cggggaggct ttgtggggcc acccagcccc ttcctcacct ctctccatct     180
```

```
ctcagactcc ccagacaggc cctggaaccc ccccaccttc tccccagccc tgctcgtggt      240
gaccgaaggg gacaacgcca ccttcacctg cagcttctcc aacacatcgg agagcttcgt      300
gctaaactgg taccgcatga gccccagcaa ccagacggac aagctggccg ccttccccga      360
ggaccgcagc cagcccggcc aggactgccg cttccgtgtc acacaactgc caacgggcg       420 tgacttccac atgagcgtgg tcagggcccg gcgcaatgac agcggcacct acctctgtgg      480
ggccatctcc ctggccccca aggcgcagat caaagagagc ctgcgggcag agctcagggt      540
gacaggtgcg gcctcggagg ccccggggca ggggtgagct gagccggtcc tggggtgggt      600
gtcccctcct gcacaggatc aggagctcca gggtcgtagg gcaggaccc cccagctcca      660 gtccagggct ctgtcctgca cctggggaat ggtgaccggc atctctgtcc tctagctctg      720
gaagcacccc agcccctcta gtctgccctc accctgacc ctgaccctcc acctgaccc       780 cgtcctaacc cctgaccttt gtgccttcc agagagaagg gcagaagtgc ccacagccca      840
ccccagcccc tcacccaggc cagccggcca gttccaaacc ctg                       883
```

<210> SEQ ID NO 24
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 24
gctctggctg gtcttcagta tg                                              22

<210> SEQ ID NO 25
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 25
ttgccgtatg gttggtttga ac                                              22

<210> SEQ ID NO 26
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 26
agcagctctg ccctcat                                                    17

<210> SEQ ID NO 27
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 27
acttccacat gagcgtgg                                                   18

<210> SEQ ID NO 28
<211> LENGTH: 18
<212> TYPE: DNA
<213> ORGANISM: Artificial Sequence
<220> FEATURE:
<223> OTHER INFORMATION: Synthetic Oligonucleotide

```
<400> SEQUENCE: 28
gggctgtggg cacttctg                                                   18

<210> SEQ ID NO 29
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 29
gcagatcaaa gagagcctgc                                                 20
```

NON-HUMAN ANIMALS HAVING A HUMANIZED PROGRAMMED CELL DEATH 1 GENE

CROSS REFERENCE TO RELATED APPLICATIONS

This application claims the benefit of priority of U.S. Provisional Application Nos. 62/014,181 filed Jun. 19, 2014, 62/086,518 filed Dec. 2, 2014, and 62/138,221 filed Mar. 25, 2015, the entire contents of which are incorporated herein by reference.

INCORPORATION BY REFERENCE OF SEQUENCE LISTING

The Sequence Listing in an ASCII text file, named 31969_SEQ.txt of 23 KB, created on Jun. 4, 2015, and submitted to the United States Patent and Trademark Office via EFS-Web, is incorporated herein by reference.

BACKGROUND

Although an intense focus of medical research and development has been devoted to cancer immunotherapy and significant improvements have been made, cancer remains a major challenge in the healthcare industry worldwide. This major challenge is due, in part, to the ability of cancer cells to evade the monitoring mechanisms of the immune system, which is partly the result of inhibition and/or down-regulation of anti-tumor immunity. Still, development of in vivo systems to optimally determine the therapeutic potential of new cancer therapies that are designed to activate and/or promote anti-tumor immunity and determine the molecular aspects of how cancer cells provide inhibitory signals to immune cells (e.g., T cells) is lacking. Such systems provide a source for assays for assessing the therapeutic efficacy of candidate agents that promote an anti-tumor environment in vivo.

SUMMARY

The present invention encompasses the recognition that it is desirable to engineer non-human animals to permit improved systems for identifying and developing new therapeutics that can be used for the treatment of cancer. The present invention also encompasses the recognition that it is desirable to engineer non-human animals to permit improved systems for identifying and developing new therapeutics that can be used to treat autoimmune (or inflammatory) diseases, disorders or conditions. Further, the present invention also encompasses the recognition that non-human animals having a humanized Pdcd1 gene and/or otherwise expressing, containing, or producing a human or humanized PD-1 polypeptide are desirable, for example for use in identifying and developing cancer therapeutics that up-regulate anti-tumor immunity. In some embodiments, non-human animals of the present invention provide improved in vivo systems for the identification and development of combination therapies that include targeting PD-1.

In some embodiments, the present invention provides a non-human animal having a genome comprising a Pdcd1 gene that includes genetic material from two different species (e.g., a human and a non-human). In some embodiments, the Pdcd1 gene of a non-human animal as described herein encodes a PD-1 polypeptide that contains human and non-human portions, wherein the human and non-human portions are linked together and form a functional PD-1 polypeptide. In some embodiments, the Pdcd1 gene of a non-human animal as described herein encodes a PD-1 polypeptide that contains an extracellular domain, in whole or in part, of a human PD-1 polypeptide.

In some embodiments, the present invention provides a non-human animal that expresses a PD-1 polypeptide, which PD-1 polypeptide comprises a human portion and an endogenous portion. In some embodiments, a PD-1 polypeptide of the present invention is translated in a cell of the non-human animal with a non-human signal peptide; in some certain embodiments, a rodent signal peptide.

In some embodiments, an endogenous portion comprises an intracellular portion of an endogenous PD-1 polypeptide. In some embodiments, an endogenous portion further comprises a transmembrane portion of an endogenous PD-1 polypeptide. In some embodiments, an endogenous portion has an amino acid sequence that is at least 50%, at least 60%, at least 70%, at least 80%, at least 90%, or at least 95% identical to a corresponding amino acid sequence of a mouse PD-1 polypeptide that appears in FIG. 8. In some embodiments, an endogenous portion has an amino acid sequence that is substantially identical to a corresponding amino acid sequence of a mouse PD-1 polypeptide that appears in FIG. 8. In some embodiments, an endogenous portion has an amino acid sequence that is identical to a corresponding amino acid sequence of a mouse PD-1 polypeptide that appears in FIG. 8.

In some embodiments, a human portion comprises amino acids 35-145, 27-145, 27-169, 26-169 or 21-170 of a human PD-1 polypeptide. In some embodiments, a human portion comprises an amino acid sequence that is at least 50%, at least 60%, at least 70%, at least 80%, at least 90%, or at least 95% identical to a corresponding amino acid sequence of a human PD-1 polypeptide that appears in FIG. 8. In some embodiments, a human portion comprises an amino acid sequence that is substantially identical to a corresponding amino acid sequence of a human PD-1 polypeptide that appears in FIG. 8. In some embodiments, a human portion comprises an amino acid sequence that is identical to a corresponding amino acid sequence of a human PD-1 polypeptide that appears in FIG. 8.

In some embodiments, a PD-1 polypeptide, which comprises a human portion and an endogenous portion, is encoded by an endogenous Pdcd1 gene. In some certain embodiments, an endogenous Pdcd1 gene comprises endogenous Pdcd1 exons 1, 4 and 5. In some certain embodiments, an endogenous Pdcd1 gene further comprises an endogenous Pdcd1 exon 3 in whole or in part. In some certain embodiments, an endogenous Pdcd1 gene comprises SEQ ID NO:21. In some certain embodiments, an endogenous Pdcd1 gene comprises SEQ ID NO:22. In some certain embodiments, an endogenous Pdcd1 gene comprises SEQ ID NO:21 and SEQ ID NO:22.

In some embodiments, a PD-1 polypeptide expressed by a non-human animal as described herein has an amino acid sequence that is at least 50%, at least 60%, at least 70%, at least 80%, at least 90%, or at least 95% identical to SEQ ID NO:6. In some embodiments, a PD-1 polypeptide expressed by a non-human animal as described herein has an amino acid sequence that is substantially identical to SEQ ID NO:6. In some embodiments, a PD-1 polypeptide expressed by a non-human animal as described herein has an amino acid sequence that is identical to SEQ ID NO:6.

In some embodiments, the present invention provides a humanized Pdcd1 locus comprising one or more exons of a non-human Pdcd1 gene operably linked to one or more exons, in whole or in part, of a human Pdcd1 gene. In some embodiments, a humanized Pdcd1 locus further comprises 5' and 3' non-human Pdcd1 untranslated regions (UTRs) flanking the one or more exons of a human Pdcd1 gene. In some embodiments, a humanized Pdcd1 locus is under the control of a rodent promoter; in some certain embodiments, an endogenous rodent promoter.

In some embodiments, a humanized Pdcd1 locus comprises non-human Pdcd1 exons 1, 3, 4 and 5 operably linked to a human Pdcd1 exon 2. In some embodiments, a humanized Pdcd1 locus comprises non-human Pdcd1 exons 1, 4 and 5, a human Pdcd1 exon 2 and further comprises a Pdcd1 exon 3, which Pdcd1 exon 3 comprises a human portion and a non-human portion, and wherein said non-human and human exons are operably linked. In some embodiments, a human portion of a Pdcd1 exon 3 includes nucleotides that encode a PD-1 stalk sequence. In some embodiments, a human portion of a Pdcd1 exon 3 includes about 71 bp of a human Pdcd1 exon 3. In some embodiments, a non-human portion of a Pdcd1 exon 3 includes nucleotides that encode a transmembrane sequence. In some embodiments, a non-human portion of a Pdcd1 exon 3 includes about 91 bp of a rodent Pdcd1 exon 3.

In some embodiments, the present invention provides a non-human animal comprising a Pdcd1 gene that comprises an endogenous portion and a human portion, where the endogenous and human portions are operably linked to a rodent Pdcd1 promoter. In some embodiments, the rodent Pdcd1 promoter is an endogenous rodent Pdcd1 promoter.

In some embodiments, an endogenous portion comprises endogenous Pdcd1 exons 1, 4 and 5. In some embodiments, an endogenous portion further comprises endogenous Pdcd1 exon 3 in whole or in part. In some embodiments, exons 1, 3 in whole or in part, 4 and 5 of an endogenous Pdcd1 gene are at least 50%, at least 60%, at least 70%, at least 80%, at least 90%, or at least 95% identical to the corresponding exons 1, 3 in whole or in part, 4 and 5 of an endogenous Pdcd1 gene that appears in FIG. 8. In some embodiments, exons 1, 3 in whole or in part, 4 and 5 of an endogenous Pdcd1 gene are at substantially identical to the corresponding exons 1, 3 in whole or in part, 4 and 5 of an endogenous Pdcd1 gene that appears in FIG. 8. In some embodiments, exons 1, 3 in whole or in part, 4 and 5 of an endogenous Pdcd1 gene are at identical to the corresponding exons 1, 3 in whole or in part, 4 and 5 of an endogenous Pdcd1 gene that appears in FIG. 8.

In some embodiments, a human portion encodes amino acids 21-170, 26-169, 27-169, 27-145 or 35-145 of a human PD-1 polypeptide.

In some embodiments, a human portion comprises exon 2 of a human Pdcd1 gene. In some embodiments, a human portion further comprises a human Pdcd1 exon 3 in whole or in part. In some embodiments, human Pdcd1 exons 2 and 3, in whole or in part, are at least 50%, at least 60%, at least 70%, at least 80%, at least 90%, or at least 95% identical to the corresponding exons 2 and 3, in whole or in part, of a human Pdcd1 gene that appears in FIG. 8. In some embodiments, human Pdcd1 exons 2 and 3, in whole or in part, are substantially identical to the corresponding exons 2 and 3, in whole or in part, of a human Pdcd1 gene that appears in FIG. 8. In some embodiments, human Pdcd1 exons 2 and 3, in whole or in part, are identical to the corresponding exons 2 and 3, in whole or in part, of a human Pdcd1 gene that appears in FIG. 8. In some embodiments, a human portion comprises a sequence that is codon-optimized for expression in a non-human animal; in some embodiments, expression in a rodent; in some certain embodiments, expression in a mouse; in some certain embodiments, expression in a rat.

In some embodiments, a human portion comprises a sequence that is at least 50%, at least 60%, at least 70%, at least 80%, at least 90%, or at least 95% identical to SEQ ID NO:23. In some embodiments, a human portion comprises a sequence that is substantially identical to SEQ ID NO:23. In some embodiments, a human portion comprises a sequence that is identical to SEQ ID NO:23. In some embodiments, a human portion comprises SEQ ID NO:23.

In some embodiments, the present invention provides a PD-1 polypeptide produced (or generated) by a non-human animal as described herein. In some certain embodiments, a PD-1 polypeptide produced by a non-human animal as described herein comprises an amino acid sequence that is at least 50%, at least 60%, at least 70%, at least 80%, at least 90%, or at least 95% identical to SEQ ID NO:6. In some certain embodiments, a PD-1 polypeptide produced by a non-human animal as described herein comprises an amino acid sequence that is substantially identical to SEQ ID NO:6. In some certain embodiments, a PD-1 polypeptide produced by a non-human animal as described herein comprises an amino acid sequence that is identical to SEQ ID NO:6.

In some embodiments, the present invention provides an isolated cell or tissue from a non-human animal as described herein. In some embodiments, the present invention provides an isolated cell or tissue that comprises a Pdcd1 gene as described herein. In some embodiments, a cell is a lymphocyte. In some embodiments, a cell is selected from a B cell, dendritic cell, macrophage, monocyte (e.g., an activated monocyte), NK cell, and T cell (e.g., an activated T cell). In some embodiments, a tissue is selected from adipose, bladder, brain, breast, bone marrow, eye, heart, intestine, kidney, liver, lung, lymph node, muscle, pancreas, plasma, serum, skin, spleen, stomach, thymus, testis, ovum, and a combination thereof.

In some embodiments, the present invention provides a non-human embryonic stem cell whose genome comprises a Pdcd1 gene as described herein. In some embodiments, a non-human embryonic stem cell is a mouse embryonic stem cell and is from a 129 strain, C57BL/6 strain or a BALB/c strain. In some embodiments, a non-human embryonic stem cell is a mouse embryonic stem cell and is from a 129 strain, C57BL/6 strain or a mixture thereof. In some embodiments, a non-human embryonic stem cell is a mouse embryonic stem cell and is from a mixture of 129 and C57BL/6 strains.

In some embodiments, a non-human embryonic stem cell has a genome comprising a Pdcd1 gene that comprises SEQ ID NO:19, SEQ ID NO:20, SEQ ID NO:21, SEQ ID NO: 22 or a combination thereof.

In some embodiments, the present invention provides the use of a non-human embryonic stem cell as described herein to make a non-human animal. In some certain embodiments, a non-human embryonic stem cell is a mouse embryonic stem cell and is used to make a mouse comprising a Pdcd1 gene as described herein. In some certain embodiments, a non-human embryonic stem cell is a rat embryonic stem cell and is used to make a rat comprising a Pdcd1 gene as described herein.

In some embodiments, the present invention provides a non-human embryo comprising, made from, obtained from, or generated from a non-human embryonic stem cell comprising a Pdcd1 gene as described herein. In some certain embodiments, a non-human embryo is a rodent embryo; in some embodiments, a mouse embryo; in some embodiments, a rat embryo.

In some embodiments, the present invention provides the use of a non-human embryo as described herein to make a non-human animal. In some certain embodiments, a non-human embryo is a mouse embryo and is used to make a mouse comprising a Pdcd1 gene as described herein. In some certain embodiments, a non-human embryo is a rat embryo and is used to make a rat comprising a Pdcd1 gene as described herein.

In some embodiments, the present invention provides a targeting vector (or nucleic acid construct) as described herein. In some embodiments, the present invention provides a targeting vector (or nucleic acid construct) that comprises a humanized Pdcd1 gene as described herein. In some embodiments, the present invention provides a targeting vector (or nucleic acid construct) that comprises a Pdcd1 gene that encodes a PD-1 polypeptide that comprises a human extracellular domain in whole or in part; in some certain embodiments a PD-1 polypeptide that comprises amino acids 21-170, 26-169, 27-169, 27-145 or 35-145 of a human PD-1 polypeptide.

In some embodiments, a targeting vector (or nucleic acid construct) comprises one or more exons, in whole or in part, of a non-human Pdcd1 gene operably linked to one or more exons, in whole or in part, of a human Pdcd1 gene. In some embodiments, a targeting vector (or nucleic acid construct) comprises 5' and 3' non-human Pdcd1 untranslated regions (UTRs) flanking the one or more exons of a human Pdcd1 gene. In some embodiments, a targeting vector (or nucleic acid construct) comprises one or more selection markers. In some embodiments, a targeting vector (or nucleic acid construct) comprises one or more site-specific recombination sites. In some embodiments, a targeting vector (or nucleic acid construct) comprises a human Pdcd1 exon 2. In some embodiments, a targeting vector (or nucleic acid construct) comprises a human Pdcd1 exon 2 and a human Pdcd1 exon 3 in whole or in part.

In some embodiments, the present invention provides use of a targeting vector (or nucleic acid construct) as described herein to make a modified non-human embryonic stem cell. In some embodiments, the present invention provides use of a targeting vector (or nucleic acid construct) as described herein to make a modified non-human embryo. In some embodiments, the present invention provides use of a targeting vector (or nucleic acid construct) as described herein to make a non-human animal.

In some embodiments, the present invention provides a method of making a non-human animal that expresses a PD-1 polypeptide from an endogenous Pdcd1 gene, wherein the PD-1 polypeptide comprises a human sequence, the method comprising (a) inserting a genomic fragment into an endogenous Pdcd1 gene in a rodent embryonic stem cell, said genomic fragment comprising a nucleotide sequence that encodes a human PD-1 polypeptide in whole or in part; (b) obtaining the rodent embryonic stem cell generated in (a); and, creating a rodent using the rodent embryonic stem cell of (b).

In some embodiments, a human sequence comprises amino acids 35-145, 27-145, 27-169, 26-169 or 21-170 of a human PD-1 polypeptide.

In some embodiments, a nucleotide sequence comprises human Pdcd1 exon 2. In some embodiments, a nucleotide sequence further comprises human Pdcd1 exon 3 in whole or in part. In some embodiments, a nucleotide sequence comprises one or more selection markers. In some embodiments, a nucleotide sequence comprises one or more site-specific recombination sites.

In some embodiments, the present invention provides a method of making a non-human animal whose genome comprises a Pdcd1 gene that encodes a PD-1 polypeptide having a human portion and an endogenous portion, which portions are operably linked to a rodent Pdcd1 promoter, the method comprising modifying the genome of a non-human animal so that it comprises a Pdcd1 gene that encodes a PD-1 polypeptide having a human portion and an endogenous portion, which portions are operably linked to a rodent Pdcd1 promoter, thereby making said non-human animal.

In some embodiments, a rodent Pdcd1 promoter is an endogenous rodent Pdcd1 promoter.

In some embodiments, a human portion comprises amino acids 35-145, 27-145, 27-169, 26-169 or 21-170 of a human PD-1 polypeptide.

In some embodiments, a Pdcd1 gene is modified to include human Pdcd1 exon 2. In some embodiments, a Pdcd1 gene is modified to include human Pdcd1 exon 2 and human Pdcd1 exon 3 in whole or in part.

In some embodiments, modifying the genome of a non-human animal is performed in a non-human embryonic stem cell followed by generating a non-human animal with said non-human embryonic stem cell. In some certain embodiments, the non-human embryonic stem cell is a rodent embryonic stem cell; in some embodiments, a mouse embryonic stem cell; in some embodiments, a rat embryonic stem cell.

In some embodiments, the present invention provides a non-human animal obtainable by methods as described herein.

In some embodiments, the present invention provides a method of reducing tumor growth in a non-human animal, the method comprising the steps of administering a drug targeting human PD-1 to a non-human animal whose genome comprises a Pdcd1 gene that encodes a PD-1 polypeptide having a human portion and an endogenous portion, which portions are operably linked to a rodent Pdcd1 promoter; the administering being performed under conditions and for a time sufficient that tumor growth is reduced in the non-human animal.

In some embodiments, the present invention provides a method of killing tumor cells in a non-human animal, the method comprising the steps of administering a drug targeting human PD-1 to a non-human animal whose genome comprises a Pdcd1 gene that encodes a PD-1 polypeptide having a human portion and an endogenous portion, which portions are operably linked to a rodent Pdcd1 promoter; the administering being performed under conditions and for a time sufficient that the drug mediates killing of the tumor cells in the non-human animal.

In some embodiments, the present invention provides a method of assessing the pharmacokinetic properties of a drug targeting human PD-1, the method comprising the steps of administering the drug to a non-human animal whose genome comprises a Pdcd1 gene that encodes a PD-1 polypeptide having a human portion and an endogenous portion, which portions are operably linked a rodent Pdcd1 promoter; and performing an assay to determine one or more pharmacokinetic properties of the drug targeting human PD-1.

In many embodiments, a non-human animal as described herein is a rodent whose genome includes a Pdcd1 gene that encodes a PD-1 polypeptide having a human portion and an endogenous portion, which portions are operably linked to a rodent Pdcd1 promoter. In many embodiments, a rodent Pdcd1 promoter is an endogenous rodent Pdcd1 promoter. In many embodiments, a human portion comprises amino acids 35-145, 27-145, 27-169, 26-169 or 21-170 of a human PD-1 polypeptide.

In some embodiments, a drug targeting human PD-1 is a PD-1 antagonist. In some embodiments, a drug targeting human PD-1 is a PD-1 agonist. In some embodiments, a drug targeting human PD-1 is an anti-PD-1 antibody. In some embodiments, a drug targeting human PD-1 is administered intravenously, intraperitoneally, or subcutaneously.

In some embodiments, the present invention provides a non-human animal tumor model, which non-human animal expresses a PD-1 polypeptide comprising a human portion and an endogenous portion.

In some embodiments, the present invention provides a non-human animal tumor model, which non-human animal has a genome comprising a Pdcd1 gene that comprises an endogenous portion and a human portion, wherein the endogenous and human portions are operably linked to a non-human animal Pdcd1 promoter.

In some embodiments, the present invention provides a non-human animal tumor model obtained by (a) providing a non-human animal whose genome comprises a Pdcd1 gene that includes an endogenous portion and a human portion, which endogenous and human portions are operatively linked to a non-human animal Pdcd1 promoter; and (b) implanting one or more tumor cells in the rodent of (a); thereby providing said non-human animal tumor model.

In some embodiments, a non-human animal tumor model of the present invention is a rodent tumor model. In some embodiments, a non-human animal Pdcd1 promoter is a rodent Pdcd1 promoter.

In some embodiments, the present invention provides a method for identification or validation of a drug or vaccine, the method comprising the steps of delivering a drug or vaccine to a non-human animal whose genome includes a Pdcd1 gene that encodes a PD-1 polypeptide, which PD-1 polypeptide comprises a human portion and an endogenous portion, and monitoring one or more of the immune response to the drug or vaccine, the safety profile of the drug or vaccine, or the effect on a disease, disorder or condition. In some embodiments, monitoring the safety profile includes determining if the non-human animal exhibits a side effect or adverse reaction as a result of delivering the drug or vaccine. In some embodiments, a side effect or adverse reaction is selected from morbidity, mortality, alteration in body weight, alteration of the level of one or more enzymes (e.g., liver), alteration in the weight of one or more organs, loss of function (e.g., sensory, motor, organ, etc.), increased susceptibility to one or more diseases, alterations to the genome of the non-human animal, increase or decrease in food consumption and complications of one or more diseases. In some embodiments, the disease, disorder or condition is induced in the non-human animal. In some embodiments, the disease, disorder or condition induced in the non-human animal is associated with a disease, disorder or condition suffered by one or more human patients in need of treatment. In some certain embodiments, the drug is an antibody.

In some embodiments, the present invention provides use of a non-human animal as described herein in the development of a drug or vaccine for use in medicine, such as use as a medicament.

In some embodiments, the present invention provides use of a non-human animal as described herein in the manufacture of a medicament for the treatment of cancer, neoplasm, an infectious disease, an inflammatory disease, disorder or condition, or an autoimmune disease, disorder or condition.

In various embodiments, a Pdcd1 gene of the present invention includes a Pdcd1 gene as described herein. In various embodiments, a Pdcd1 gene of the present invention encodes a PD-1 polypeptide having a human portion and an endogenous portion, which portions are operably linked to a rodent Pdcd1 promoter. In various embodiments, a rodent promoter is an endogenous rodent promoter. In various embodiments, a human portion comprises a human Pdcd1 exon 2. In various embodiments, a human portion comprises a human Pdcd1 exon 2 and further comprises a human Pdcd1 exon 3 in whole or in part.

In various embodiments, a PD-1 polypeptide of the present invention includes a PD-1 polypeptide as described herein. In various embodiments, a non-human animal of the present invention does not detectably express a full-length endogenous non-human PD-1 polypeptide. In various embodiments, a non-human animal of the present invention does not detectably express an extracellular portion of an endogenous PD-1 polypeptide. In various embodiments, a non-human animal of the present invention does not detectably express an N-terminal immunoglobulin V domain of an endogenous PD-1 polypeptide.

In various embodiments, a non-human animal of the present invention is a rodent; in some embodiments, a mouse; in some embodiments, a rat. In some embodiments, a mouse of the present invention is selected from the group consisting of a 129 strain, a BALB/C strain, a C57BL/6 strain, and a mixed 129×C57BL/6 strain; in some certain embodiments, 50% 129 and 50% C57BL/6; in some certain embodiments, 25% 129 and 75% C57BL/6.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description of certain embodiments that follows. It should be understood, however, that the detailed description, while indicating certain embodiments of the present invention, is given by way of illustration only, not limitation. Various changes and modifications within the scope of the invention will become apparent to those skilled in the art from the detailed description.

BRIEF DESCRIPTION OF THE DRAWING

The Drawing included herein, which is composed of the following Figures, is for illustration purposes only and not for limitation.

FIG. 8 sets forth exemplary murine, human and humanized Pdcd1 and PD-1 sequences, and an exemplary human nucleic acid sequence for humanization of a non-human Pdcd1 gene. For mRNA sequences, bold font indicates coding sequence and consecutive exons, where indicated, are separated by alternating underlined text; for humanized mRNA sequences, human sequences are contained within parentheses. For protein sequences, signal peptides are underlined, extracellular sequences are bold font, immunoglobulin V domain sequences are within parentheses, and intracellular sequences are italicized; and for humanized protein sequences, non-human sequences are indicated in regular font, and human sequences are indicated in bold font.

DEFINITIONS

Figure 1:
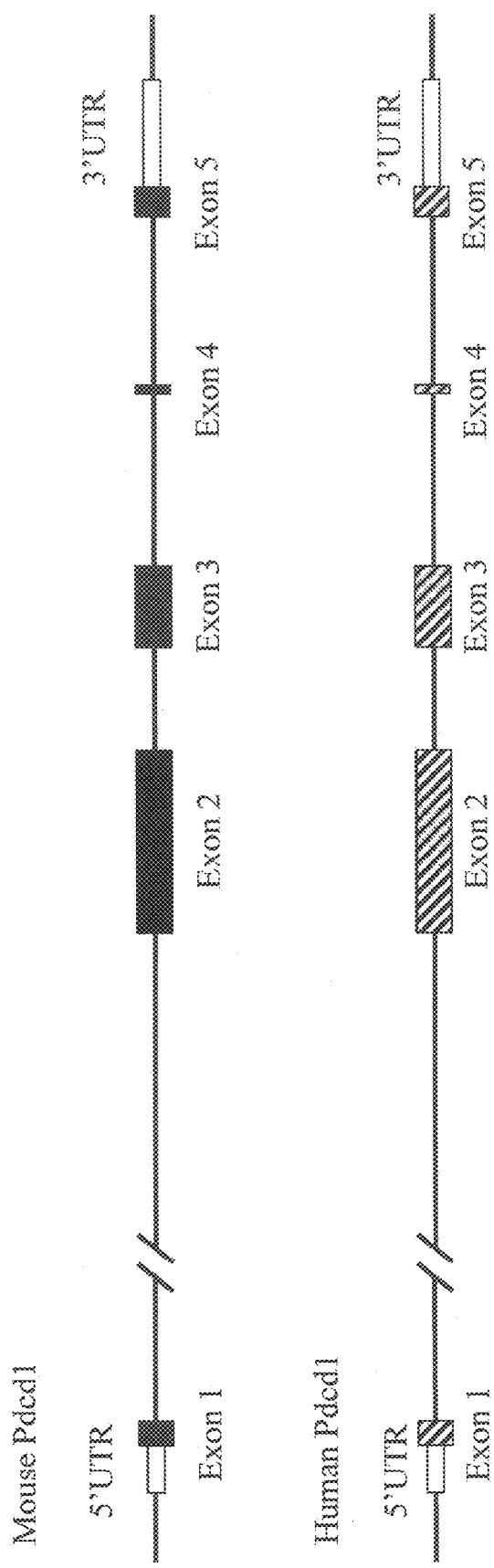
FIG. 1 shows a diagram, not to scale, of the genomic organization of a non-human (e.g., mouse) and human Programmed cell death 1 (Pdcd1) genes. Exons and untranslated regions (UTRs) are numbered beneath each exon and above each UTR.

This invention is not limited to particular methods and experimental conditions described herein, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. All publications mentioned herein are hereby incorporated by reference.

The term "approximately", as applied herein to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "biologically active" includes a characteristic of any agent that has activity in a biological system, in vitro or in vivo (e.g., in an organism). For instance, an agent that, when present in an organism, has a biological effect within that organism, is considered to be biologically active. In particular embodiments, where a protein or polypeptide is biologically active, a portion of that protein or polypeptide that shares at least one biological activity of the protein or polypeptide is typically referred to as a "biologically active" portion.

The term "comparable" includes to two or more agents, entities, situations, sets of conditions, etc. that may not be identical to one another but that are sufficiently similar to permit comparison between them so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

The term "conservative", e.g., as in a conservative amino acid substitution, includes substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a receptor to bind to a ligand. Examples of groups of amino acids that have side chains with similar chemical properties include: aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet et al. (1992) Exhaustive Matching of the Entire Protein Sequence Database, Science 256:1443-45, hereby incorporated by reference. In some embodiments, the substitution is a moderately conservative substitution wherein the substitution has a nonnegative value in the PAM250 log-likelihood matrix.

The term "control" includes the art-understood meaning of a "control" being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. As used herein, a "control" may include a "control animal". A "control animal" may have a modification as described herein, a modification that is different as described herein, or no modification (i.e., a wild-type animal). In one experiment, the "test" (i.e., the variable being tested) is applied. In the second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control.

The term "disruption" includes the result of a homologous recombination event with a DNA molecule (e.g., with an endogenous homologous sequence such as a gene or gene locus). In some embodiments, a disruption may achieve or represent an insertion, deletion, substitution, replacement, missense mutation, or a frame-shift of a DNA sequence(s), or any combination thereof. Insertions may include the insertion of entire genes or fragments of genes, e.g., exons, which may be of an origin other than the endogenous sequence (e.g., a heterologous sequence). In some embodiments, a disruption may increase expression and/or activity of a gene or gene product (e.g., of a protein encoded by a gene). In some embodiments, a disruption may decrease expression and/or activity of a gene or gene product. In some embodiments, a disruption may alter sequence of a gene or an encoded gene product (e.g., an encoded protein). In some embodiments, a disruption may truncate or fragment a gene or an encoded gene product (e.g., an encoded protein). In some embodiments, a disruption may extend a gene or an encoded gene product; in some such embodiments, a disruption may achieve assembly of a fusion protein. In some embodiments, a disruption may affect level but not activity of a gene or gene product. In some embodiments, a disruption may affect activity but not level of a gene or gene product. In some embodiments, a disruption may have no significant effect on level of a gene or gene product. In some embodiments, a disruption may have no significant effect on activity of a gene or gene product. In some embodiments, a disruption may have no significant effect on either level or activity of a gene or gene product.

The terms "determining", "measuring", "evaluating", "assessing", "assaying" and "analyzing" are used interchangeably to refer to any form of measurement, and include determining if an element is present or not. These terms include both quantitative and/or qualitative determinations. Assaying may be relative or absolute. "Assaying for the presence of" can be determining the amount of something present and/or determining whether or not it is present or absent.

The term "dosing regimen" or "therapeutic regimen" includes a set of unit doses, in some embodiments, more than one, that are administered individually to a subject, typically separated by periods of time. In some embodiments, a given therapeutic agent has a recommended dosing regiment, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses.

The phrase "endogenous locus" or "endogenous gene" includes a genetic locus found in a parent or reference organism. In some embodiments, the endogenous locus has a sequence found in nature. In some embodiments, the endogenous locus is a wild type locus. In some embodiments, the reference organism is a wild-type organism. In some embodiments, the reference organism is an engineered organism. In some embodiments, the reference organism is a laboratory-bred organism (whether wild-type or engineered).

The phrase "endogenous promoter" includes a promoter that is naturally associated, e.g., in a wild-type organism, with an endogenous gene.

The term "heterologous" includes an agent or entity from a different source. For example, when used in reference to a polypeptide, gene, or gene product or present in a particular cell or organism, the term clarifies that the relevant polypeptide, gene, or gene product: 1) was engineered by the hand of man; 2) was introduced into the cell or organism (or a precursor thereof) through the hand of man (e.g., via genetic engineering); and/or 3) is not naturally produced by or present in the relevant cell or organism (e.g., the relevant cell type or organism type).

The term "host cell" includes a cell into which a heterologous (e.g., exogenous) nucleic acid or protein has been introduced. Persons of skill upon reading this disclosure will understand that such terms refer not only to the particular subject cell, but also is used to refer to the progeny of such a cell. Because certain modifications may occur in succeeding generations due to either mutation or environmental influences, such progeny may not, in fact, be identical to the parent cell, but are still included within the scope of the term "host cell". In some embodiments, a host cell is or comprises a prokaryotic or eukaryotic cell. In general, a host cell is any cell that is suitable for receiving and/or producing a heterologous nucleic acid or protein, regardless of the Kingdom of life to which the cell is designated. Exemplary cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell). In some embodiments, a host cell is or comprises an isolated cell. In some embodiments, a host cell is part of a tissue. In some embodiments, a host cell is part of an organism.

The term "humanized" includes nucleic acids or proteins whose structures (i.e., nucleotide or amino acid sequences) include portions that correspond substantially or identically with structures of a particular gene or protein found in nature in a non-human animal, and also include portions that differ from that found in the relevant particular non-human gene or protein and instead correspond more closely with comparable structures found in a corresponding human gene or protein. In some embodiments, a "humanized" gene is one that encodes a polypeptide having substantially the amino acid sequence as that of a human polypeptide (e.g., a human protein or portion thereof—e.g., characteristic portion thereof). To give but one example, in the case of a membrane receptor, a "humanized" gene may encode a polypeptide having an extracellular portion, in whole or in part, having an amino acid sequence as that of a human extracellular portion and the remaining sequence as that of a non-human (e.g., mouse) polypeptide. In some embodiments, a humanized gene comprises at least a portion of a DNA sequence of a human gene. In some embodiment, a humanized gene comprises an entire DNA sequence of a human gene. In some embodiments, a humanized protein comprises a sequence having a portion that appears in a human protein. In some embodiments, a humanized protein comprises an entire sequence of a human protein and is expressed from an endogenous locus of a non-human animal that corresponds to the homolog or ortholog of the human gene.

The term "identity", e.g., as in connection with a comparison of sequences, includes identity as determined by a number of different algorithms known in the art that can be used to measure nucleotide and/or amino acid sequence identity. In some embodiments, identities as described herein are determined using a ClustalW v. 1.83 (slow) alignment employing an open gap penalty of 10.0, an extend gap penalty of 0.1, and using a Gonnet similarity matrix (MACVECTOR™ 10.0.2, MacVector Inc., 2008).

The term "isolated" includes a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. A substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when: a) by virtue of its origin or source of derivation is not associated with some or all of the components that accompany it in its native state in nature; b) it is substantially free of other polypeptides or nucleic acids of the same species from the species that produces it in nature; or c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components: a) with which it is associated in nature; and/or b) with which it was associated when initially produced.

The phrase "non-human animal" includes any vertebrate organism that is not a human. In some embodiments, a non-human animal is a cyclostome, a bony fish, a cartilaginous fish (e.g., a shark or a ray), an amphibian, a reptile, a mammal, and a bird. In some embodiments, a non-human mammal is a primate, a goat, a sheep, a pig, a dog, a cow, or a rodent. In some embodiments, a non-human animal is a rodent such as a rat or a mouse.

The phrase "nucleic acid" includes any compound and/or substance that is or can be incorporated into an oligonucleotide chain. In some embodiments, a "nucleic acid" is a compound and/or substance that is or can be incorporated into an oligonucleotide chain via a phosphodiester linkage. As will be clear from context, in some embodiments, "nucleic acid" includes individual nucleic acid residues (e.g., nucleotides and/or nucleosides); in some embodiments, "nucleic acid" includes an oligonucleotide chain comprising individual nucleic acid residues. In some embodiments, a "nucleic acid" is or comprises RNA; in some embodiments, a "nucleic acid" is or comprises DNA. In some embodiments, a "nucleic acid" is, comprises, or consists of one or more natural nucleic acid residues. In some embodiments, a "nucleic acid" is, comprises, or consists of one or more nucleic acid analogs. In some embodiments, a nucleic acid analog differs from a "nucleic acid" in that it does not utilize a phosphodiester backbone. For example, in some embodiments, a "nucleic acid" is, comprises, or consists of one or more "peptide nucleic acids", which are known in the art and have peptide bonds instead of phosphodiester bonds in the backbone, are considered within the scope of the present invention. Alternatively or additionally, in some embodiments, a "nucleic acid" has one or more phosphorothioate and/or 5'-N-phosphoramidite linkages rather than phosphodiester bonds. In some embodiments, a "nucleic acid" is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a "nucleic acid" is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a "nucleic acid" comprises one or more modified sugars (e.g., 2'-fluororibose, ribose, 2'-deoxyribose, arabinose, and hexose) as compared with those in natural nucleic acids. In some embodiments, a "nucleic acid" has a nucleotide sequence that encodes a functional gene product such as an RNA or protein. In some embodiments, a "nucleic acid" includes one or more introns. In some embodiments, a "nucleic acid" is prepared by one or more of isolation from a natural source, enzymatic synthesis by polymerization based on a complementary template (in vivo or in vitro), reproduction in a recombinant cell or system, and chemical synthesis. In some embodiments, a "nucleic acid" is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a "nucleic acid" is single stranded; in some embodiments, a "nucleic acid" is double stranded. In some embodiments, a "nucleic acid" has a nucleotide sequence comprising at least one element that encodes, or is the complement of a sequence that encodes, a polypeptide. In some embodiments, a "nucleic acid" has enzymatic activity.

The phrase "operably linked" includes a juxtaposition wherein the components described are in a relationship permitting them to function in their intended manner A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" includes polynucleotide sequences, which are necessary to effect the expression and processing of coding sequences to which they are ligated. "Expression control sequences" include: appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism. For example, in prokaryotes, such control sequences generally include promoter, ribosomal binding site, and transcription termination sequence, while in eukaryotes, typically, such control sequences include promoters and transcription termination sequence. The term "control sequences" is intended to include components whose presence is essential for expression and processing, and can also include additional components whose presence is advantageous, for example, leader sequences and fusion partner sequences.

The term "patient" or "subject" includes any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a non-human animal. In some embodiments, a patient (e.g., a non-human animal patient) may have a modification as described herein, a modification that is different as described herein or no modification (i.e., a wild-type non-human animal patient). In some embodiments, a non-human animal is suffering from or is susceptible to one or more disorders or conditions. In some embodiments, a non-human animal displays one or more symptoms of a disorder or condition. In some embodiments, a non-human animal has been diagnosed with one or more disorders or conditions.

The term "polypeptide" includes any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that contains portions that occur in nature separately from one another (i.e., from two or more different organisms, for example, human and non-human portions). In some embodiments, a polypeptide has an amino acid sequence that is engineered in that it is designed and/or produced through action of the hand of man.

The term "recombinant", is intended to include polypeptides (e.g., PD-1 polypeptides as described herein) that are designed, engineered, prepared, expressed, created or isolated by recombinant means, such as polypeptides expressed using a recombinant expression vector transfected into a host cell, polypeptides isolated from a recombinant, combinatorial human polypeptide library (Hoogenboom H. R., (1997) *TIB Tech.* 15:62-70; Azzazy H., and Highsmith W. E., (2002) *Clin. Biochem.* 35:425-445; Gavilondo J. V., and Larrick J. W. (2002) *BioTechniques* 29:128-145; Hoogenboom H., and Chames P. (2000) *Immunology Today* 21:371-378), antibodies isolated from an animal (e.g., a mouse) that is transgenic for human immunoglobulin genes (see e.g., Taylor, L. D., et al. (1992) *Nucl. Acids Res.* 20:6287-6295; Kellermann S-A., and Green L. L. (2002) *Current Opinion in Biotechnology* 13:593-597; Little M. et al. (2000) *Immunology Today* 21:364-370; Murphy, A. J., et al. (2014) *Proc. Natl. Acad. Sci. U.S.A* 111(14):5153-5158) or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements result from mutagenesis (e.g., in vivo or in vitro) of a known sequence element, e.g., from a natural or synthetic source. For example, in some embodiments, a recombinant polypeptide is comprised of sequences found in the genome of a source organism of interest (e.g., human, mouse, etc.). In some embodiments, a recombinant polypeptide has an amino acid sequence that resulted from mutagenesis (e.g., in vitro or in vivo, for example in a non-human animal), so that the amino acid sequences of the recombinant polypeptides are sequences that, while originating from and related to polypeptides sequences, may not naturally exist within the genome of a non-human animal in vivo.

The term "replacement" includes a process through which a "replaced" nucleic acid sequence (e.g., a gene) found in a host locus (e.g., in a genome) is removed from that locus, and a different, "replacement" nucleic acid is located in its place. In some embodiments, the replaced nucleic acid sequence and the replacement nucleic acid sequences are comparable to one another in that, for example, they are homologous to one another and/or contain corresponding elements (e.g., protein-coding elements, regulatory elements, etc.). In some embodiments, a replaced nucleic acid sequence includes one or more of a promoter, an enhancer, a splice donor site, a splice receiver site, an intron, an exon, an untranslated region (UTR); in some embodiments, a replacement nucleic acid sequence includes one or more coding sequences. In some embodiments, a replacement nucleic acid sequence is a homolog of the replaced nucleic acid sequence. In some embodiments, a replacement nucleic acid sequence is an ortholog of the replaced sequence. In some embodiments, a replacement nucleic acid sequence is or comprises a human nucleic acid sequence. In some embodiments, including where the replacement nucleic acid sequence is or comprises a human nucleic acid sequence, the replaced nucleic acid sequence is or comprises a rodent sequence (e.g., a mouse or rat sequence). The nucleic acid sequence so placed may include one or more regulatory sequences that are part of source nucleic acid sequence used to obtain the sequence so placed (e.g., promoters, enhancers, 5'- or 3'-untranslated regions, etc.). For example, in various embodiments, the replacement is a substitution of an endogenous sequence with a heterologous sequence that results in the production of a gene product from the nucleic acid sequence so placed (comprising the heterologous sequence), but not expression of the endogenous sequence; the replacement is of an endogenous genomic sequence with a nucleic acid sequence that encodes a polypeptide that has a similar function as a polypeptide encoded by the endogenous sequence (e.g., the endogenous genomic sequence encodes a PD-1 polypeptide, and the DNA fragment encodes one or more human PD-1 polypeptides). In various embodiments, an endogenous gene or fragment thereof is replaced with a corresponding human gene or fragment thereof. A corresponding human gene or fragment thereof is a human gene or fragment that is an ortholog of, or is substantially similar or the same in structure and/or function, as the endogenous gene or fragment thereof that is replaced.

The phrase "Programmed cell death 1 protein" or "PD-1 protein" includes a type I transmembrane protein that belongs to the CD28/CTLA-4 family of T cell regulators. The protein structure of a PD-1 protein includes an extracellular amino-terminal immunoglobulin V domain, a transmembrane domain and a carboxyl-terminal intracellular tail, which intracellular tail contains an immunoreceptor tyrosine-based inhibitory motif (ITIM) and an immunoreceptor tyrosine-based switch motif. PD-1 is expressed on the cell surface and interacts with PD-L1 and PD-L2, members of the B7 family immune-regulatory ligands (Collins, M. et al. (2005) Genome Biol. 6:223). PD-1 is expressed in, inter alia, activated T cells, B cells, macrophages, monocytes, mast cells, and also in many tumors. PD-1 has been shown to be involved in negative regulation of immune response and, in particular, negative regulation of T cell responses. By way of illustration, nucleotide and amino acid sequences of mouse and human Pdcd1 genes, which encode PD-1 proteins, are provided in FIG. 8. Persons of skill upon reading this disclosure will recognize that one or more endogenous Pdcd1 genes in a genome (or all) can be replaced by one or more heterologous Pdcd1 genes (e.g., polymorphic variants, subtypes or mutants, genes from another species, humanized forms, etc.).

A "PD-1-expressing cell" includes a cell that expresses a PD-1 type I membrane protein. In some embodiments, a PD-1-expressing cell expresses a PD-1 type I membrane protein on its surface. In some embodiments, a PD-1 protein is expressed on the surface of the cell in an amount sufficient to mediate cell-to-cell interactions. Exemplary PD-1-expressing cells include B cells, macrophages and T cells. PD-1-expressing cells regulate various cellular processes via the interaction of PD-1 expressed on the surface of immune cells (e.g., T and B cells) and play a role in determining the differentiation and fate of such cells. In some embodiments, non-human animals of the present invention demonstrate regulation of various cellular processes (as described herein) via humanized PD-1 proteins expressed on the surface of one more cells of the non-human animal. In some embodiments, non-human animals of the present invention demonstrate negative regulation of signaling through T cell receptors (TCRs) via humanized PD-1 proteins expressed on the surface of one or more cells of the non-human animal. In some embodiments, non-human animals demonstrate negative regulation of immune responses via humanized PD-1 proteins expressed on the surface of one or more cells of the non-human animal.

The term "reference" includes a standard or control agent, cohort, individual, population, sample, sequence or value against which an agent, animal, cohort, individual, population, sample, sequence or value of interest is compared. In some embodiments, a reference agent, cohort, individual, population, sample, sequence or value is tested and/or determined substantially simultaneously with the testing or determination of the agent, cohort, individual, population, sample, sequence or value of interest. In some embodiments, a reference agent, cohort, individual, population, sample, sequence or value is a historical reference, optionally embodied in a tangible medium. In some embodiments, a reference may refer to a control. As used herein, a "reference" may include a "reference animal". A "reference animal" may have a modification as described herein, a modification that is different as described herein or no modification (i.e., a wild-type animal). Typically, as would be understood by those skilled in the art, a reference agent, animal, cohort, individual, population, sample, sequence or value is determined or characterized under conditions comparable to those utilized to determine or characterize the agent, animal (e.g., a mammal), cohort, individual, population, sample, sequence or value of interest.

The term "substantially" includes the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

The phrase "substantial homology" includes a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. Typical amino acid categorizations are summarized in Table 1 and 2.

TABLE 1

| Alanine | Ala | A | Nonpolar | Neutral | 1.8 |
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

TABLE 2

| Ambiguous Amino Acids | 3-Letter | 1-Letter |
| --- | --- | --- |
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul et al. (1990) Basic local alignment search tool, *J. Mol. Biol.*, 215(3): 403-410; Altschul et al. (1997) *Methods in Enzymology*; Altschul et al., "Gapped BLAST and PSI-BLAST: a new generation of protein database search programs", *Nucleic Acids Res.* 25:3389-3402; Baxevanis et al. (1998) Bioinformatics: A Practical Guide to the Analysis of Genes and Proteins, Wiley; and Misener et al. (eds.) (1999) Bioinformatics Methods and Protocols (*Methods in Molecular Biology*, Vol. 132), Humana Press. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 9, 10, 11, 12, 13, 14, 15, 16, 17 or more residues. In some embodiments, the relevant stretch includes contiguous residues along a complete sequence. In some embodiments, the relevant stretch includes discontinuous residues along a complete sequence. In some embodiments, the relevant stretch is at least 10, 15, 20, 25, 30, 35, 40, 45, 50, or more residues.

The phrase "substantial identity" includes a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul et al. (1990) Basic local alignment search tool, *J. Mol. Biol.*, 215(3): 403-410; Altschul et al., *Methods in Enzymology*; Altschul et al. (1997) *Nucleic Acids Res.* 25:3389-3402; Baxevanis et al. (1998) Bioinformatics: A Practical Guide to the Analysis of Genes and Proteins, Wiley; and Misener et al., (eds.) (1999) Bioinformatics Methods and Protocols (*Methods in Molecular Biology, Vol. 132*), Humana Press. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, or more residues.

The phrase "targeting vector" or "targeting construct" includes a polynucleotide molecule that comprises a targeting region. A targeting region comprises a sequence that is identical or substantially identical to a sequence in a target cell, tissue or animal and provides for integration of the targeting construct into a position within the genome of the cell, tissue or animal via homologous recombination. Targeting regions that target using site-specific recombinase recognition sites (e.g., loxP or Frt sites) are also included. In some embodiments, a targeting construct of the present invention further comprises a nucleic acid sequence or gene of particular interest, a selectable marker, control and or regulatory sequences, and other nucleic acid sequences that allow for recombination mediated through exogenous addition of proteins that aid in or facilitate recombination involving such sequences. In some embodiments, a targeting construct of the present invention further comprises a gene of interest in whole or in part, wherein the gene of interest is a heterologous gene that encodes a protein, in whole or in part, that has a similar function as a protein encoded by an endogenous sequence. In some embodiments, a targeting construct of the present invention further comprises a humanized gene of interest, in whole or in part, wherein the humanized gene of interest encodes a protein, in whole or in part, that has a similar function as a protein encoded by the endogenous sequence.

The phrase "therapeutically effective amount" includes an amount that produces the desired effect for which it is administered. In some embodiments, the term refers to an amount that is sufficient, when administered to a subject (e.g., an animal) suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to subjects in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

The term "treatment" (also "treat" or "treating"), in its broadest sense includes any administration of a substance (e.g., provided compositions) that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be administered to a subject who does not exhibit signs of the relevant disease, disorder and/or condition and/or of a subject who exhibits only early signs of the disease, disorder, and/or condition. Alternatively or additionally, in some embodiments, treatment may be administered to a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

The term "variant" includes an entity that shows significant structural identity with a reference entity, but differs structurally from the reference entity in the presence or level of one or more chemical moieties as compared with the reference entity. In many embodiments, a "variant" also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A "variant", by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs. double, E vs. Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a "variant polypeptide" may differ from a reference polypeptide as a result of one or more differences in amino acid sequence and/or one or more differences in chemical moieties (e.g., carbohydrates, lipids, etc.) covalently attached to the polypeptide backbone. In some embodiments, a "variant polypeptide" shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a "variant polypeptide" does not share at least one characteristic sequence element with a reference polypeptide. In some embodiments, the reference polypeptide has one or more biological activities. In some embodiments, a "variant polypeptide" shares one or more of the biological activities of the reference polypeptide. In some embodiments, a "variant polypeptide" lacks one or more of the biological activities of the reference polypeptide. In some embodiments, a "variant polypeptide" shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a "variant" has 10, 9, 8, 7, 6, 5, 4, 3, 2, or 1 substituted residue as compared with a parent. Often, a "variant" has a very small number (e.g., fewer than 5, 4, 3, 2, or 1) number of substituted functional residues (i.e., residues that participate in a particular biological activity). Furthermore, a "variant" typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

The term "vector" includes a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

The term "wild-type" includes an entity having a structure and/or activity as found in nature in a "normal" (as contrasted with mutant, diseased, altered, etc.) state or context. Those of ordinary skill in the art will appreciate that wild-type genes and polypeptides often exist in multiple different forms (e.g., alleles).

DETAILED DESCRIPTION OF CERTAIN EMBODIMENTS

The present invention provides, among other things, improved and/or engineered non-human animals having humanized genetic material encoding a Programmed cell death 1 (Pdcd1) gene for determining the therapeutic efficacy of Pdcd1 modulators (e.g., an anti-PD-1 antibody) for the treatment of cancer, and assays in T cell responses and signal transduction. It is contemplated that such non-human animals provide an improvement in determining the therapeutic efficacy of PD-1 modulators and their potential for PD-1 blockade. Therefore, the present invention is particularly useful for the development of anti-PD-1 therapies for the treatment of various cancers, as well as for augmenting immune responses to treat and/or remove viral infection in non-human animals. In particular, the present invention encompasses the humanization of a murine Pdcd1 gene resulting in expression of a humanized PD-1 protein on the surface of cells of the non-human animal. Such humanized PD-1 proteins have the capacity to provide a source of human PD-1$^+$ cells for determining the efficacy of anti-PD-1 therapeutics to promote anti-tumor immune responses. In some embodiments, non-human animals of the present invention demonstrate augmented immune responses via blockade of PD-1 signaling through the humanized PD-1 protein expressed on the surface of cells of the non-human animal. In some embodiments, humanized PD-1 proteins have a sequence corresponding to the N-terminal immunoglobulin V domain, in whole or in part, of a human PD-1 protein. In some embodiments, humanized PD-1 proteins have a sequence corresponding to the intracellular tail of a murine PD-1 protein; in some embodiments, a sequence corresponding to the transmembrane domain and intracellular tail of a murine PD-1 protein. In some embodiments, humanized PD-1 proteins have a sequence corresponding to amino acid residues 21-170 (or 26-169, 27-169, or 27-145, or 35-145) of a human PD-1 protein. In some embodiments, non-human animals of the present invention comprise an endogenous Pdcd1 gene that contains genetic material from the non-human animal and a heterologous species (e.g., a human). In some embodiments, non-human animals of the present invention comprise a humanized Pdcd1 gene, wherein the humanized Pdcd1 gene comprises exon 2 and exon 3, in whole or in part, of a human PDCD1 gene. In some certain embodiments, non-human animals of the present invention comprise a humanized Pdcd1 gene, wherein the humanized Pdcd1 gene comprises 883 bp of a human PDCD1 gene corresponding to exon 2 and the first 71 bp of exon 3 (i.e., encoding the stalk) of a human PDCD1 gene.

Various aspects of the invention are described in detail in the following sections. The use of sections is not meant to limit the invention. Each section can apply to any aspect of the invention. In this application, the use of "or" means "and/or" unless stated otherwise.

Programmed Cell Death 1 (Pdcd1) Gene

Pdcd1 (also referred to as CD279) was originally discovered as an upregulated gene in a T cell hybridoma that was undergoing apoptosis (Ishida, Y. et al. (1992) EMBO J. 11(11):3887-3895). The Pdcd1 gene consists of 5 exons that encode PD-1, which is a type I membrane protein (referred to as PD-1) that includes an N-terminal immunoglobulin V (IgV) domain, a stalk (~20 amino acids in length), a transmembrane domain, and an intracellular tail that contains both an immunoreceptor tyrosine inhibitory motif (ITIM) and an immunoreceptor tyrosine switch motif (ITSM). PD-1 is expressed on many cell types such as, for example, B cells, dendritic cells, activated monocytes, natural killer (NK) cells and activated T cells (Keir, M. E., et al. (2008) Annu. Rev. Immunol. 26:677-704). Various splice variants of PD-1 have also been reported and vary based on which exon is lacking (Nielsen, C. et al. (2005) Cell. Immunol. 235:109-116). Indeed, certain splice variants have been observed as a causative factor in autoimmune diseases (Wan, B. et al. (2006) J. Immunol. 177(12):8844-8850). Further, Pdcd1-deficient mice have been reported to develop autoimmune conditions (Nishimura, H. et al. (1998) Intern. Immunol. 10(10):1563-1572; Nishimura, H. et al. (1999) Immunity 11:141-151; Nishimura, H. et al. (2001) Science 291:319-322), which have lead the way to solidifying PD-1 as a negative regulator of activated lymphocytes and serves to protect against the development of autoimmune disease. Interestingly, tumors have been discovered to use PD-1 signaling to evade surveillance by the immune system. Therefore, PD-1 and at least one of its ligands (i.e., PD-L1) are currently being explored as targets for cancer therapy by promotion of anti-tumor activity in tumor microenvironments via PD-1 blockade (see e.g., Pedoeem, A. et al. (2014) Clin. Immunol. 153:145-152; and Philips, G. K. and Atkins, M. (2014) Intern. Immunol. 8 pages).

A more thorough and detailed understanding of PD-1-mediated functions and the PD-1 pathway is needed to develop practical targeted therapies for future cancer treatment.

Pdcd1 and PD-1 Sequences

Exemplary murine, human and humanized Pdcd1 and PD-1 sequences are set forth in FIG. 8. An exemplary human nucleic acid sequence for humanization of a non-human Pdcd1 gene is also set forth in FIG. 8.

Humanized Pdcd1 Non-Human Animals

Non-human animals are provided that express humanized PD-1 proteins on the surface of cells of the non-human animals resulting from a genetic modification of an endogenous locus (e.g., a Pdcd1 locus) of the non-human animal that encodes a PD-1 protein. Suitable examples described herein include rodents, in particular, mice.

A humanized Pdcd1 gene, in some embodiments, comprises genetic material from a heterologous species (e.g., humans), wherein the humanized Pdcd1 gene encodes a PD-1 protein that comprises the encoded portion of the genetic material from the heterologous species. In some embodiments, a humanized Pdcd1 gene of the present invention comprises genomic DNA of a heterologous species that encodes the extracellular portion of a PD-1 protein that is expressed on the plasma membrane of a cell. Non-human animals, embryos, cells and targeting constructs for making non-human animals, non-human embryos, and cells containing said humanized Pdcd1 gene are also provided.

In some embodiments, an endogenous Pdcd1 gene is deleted. In some embodiments, an endogenous Pdcd1 gene is altered, wherein a portion of the endogenous Pdcd1 gene is replaced with a heterologous sequence (e.g., a human PDCD1 sequence, in whole or in part). In some embodiments, all or substantially all of an endogenous Pdcd1 gene is replaced with a heterologous gene (e.g., a human PDCD1 gene). In some embodiments, a portion of a heterologous Pdcd1 gene is inserted into an endogenous non-human Pdcd1 gene at an endogenous Pdcd1 locus. In some embodiments, the heterologous gene is a human gene. In some embodiments, the modification or humanization is made to one of the two copies of the endogenous Pdcd1 gene, giving rise to a non-human animal that is heterozygous with respect to the humanized Pdcd1 gene. In other embodiments, a non-human animal is provided that is homozygous for a humanized Pdcd1 gene.

In various aspects, a non-human animal contains a human PDCD1 gene, in whole or in part, at an endogenous non-human Pdcd1 locus. Thus, such non-human animals can be described as having a heterologous Pdcd1 gene. The replaced, inserted, modified or altered Pdcd1 gene at the endogenous Pdcd1 locus or a protein expressed from such gene can be detected using a variety of methods including, for example, PCR, Western blot, Southern blot, restriction fragment length polymorphism (RFLP), or a gain or loss of allele assay. In some embodiments, the non-human animal is heterozygous with respect to the humanized Pdcd1 gene.

In various embodiments, a humanized Pdcd1 gene according to the present invention includes a Pdcd1 gene that has a second exon having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a second exon that appears in a human PDCD1 gene of FIG. 8.

In various embodiments, a humanized Pdcd1 gene according to the present invention includes a Pdcd1 gene that has a second exon having a sequence that is substantially identical to a second exon that appears in a human PDCD1 gene of FIG. 8.

In various embodiments, a humanized Pdcd1 gene according to the present invention includes a Pdcd1 gene that has a second exon having a sequence that is identical to a second exon that appears in a human PDCD1 gene of FIG. 8.

In various embodiments, a humanized Pdcd1 gene according to the present invention includes a Pdcd1 gene that has a third exon having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a third exon that appears in a humanized Pdcd1 mRNA sequence of FIG. 8.

In various embodiments, a humanized Pdcd1 gene according to the present invention includes a Pdcd1 gene that has a third exon having a sequence that is substantially identical to a third exon that appears in a humanized Pdcd1 mRNA sequence of FIG. 8.

In various embodiments, a humanized Pdcd1 gene according to the present invention includes a Pdcd1 gene that has a third exon having a sequence that is identical to a third exon that appears in a humanized Pdcd1 mRNA sequence of FIG. 8.

In various embodiments, a humanized Pdcd1 gene according to the present invention includes a Pdcd1 gene that comprises a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to SEQ ID NO:21 or SEQ ID NO:23.

In various embodiments, a humanized Pdcd1 gene according to the present invention includes a Pdcd1 gene that comprises a sequence that is substantially identical to SEQ ID NO:21 or SEQ ID NO:23.

In various embodiments, a humanized Pdcd1 gene according to the present invention includes a Pdcd1 gene that comprises a sequence that is identical to SEQ ID NO:21 or SEQ ID NO:23.

In various embodiments, a humanized Pdcd1 gene according to the present invention includes a Pdcd1 gene that has a second exon and a portion of a third exon each having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a second exon and a portion of a third exon that appear in a human PDCD1 gene of FIG. 8.

In various embodiments, a humanized Pdcd1 gene according to the present invention includes a Pdcd1 gene that has a first, fourth and fifth exon each having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a first, fourth and fifth exon that appear in a mouse Pdcd1 gene of FIG. 8.

In various embodiments, a humanized Pdcd1 gene according to the present invention includes a Pdcd1 gene that has a first, a portion of a third, a fourth and a fifth exon each having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a first, a portion of a third, a fourth and a fifth exon that appear in a mouse Pdcd1 gene of FIG. 8.

In various embodiments, a humanized Pdcd1 gene according to the present invention includes a Pdcd1 gene that has a 5' untranslated region and a 3' untranslated region each having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a 5' untranslated region and a 3' untranslated region that appear in a mouse Pdcd1 gene of FIG. 8.

In various embodiments, a humanized Pdcd1 gene according to the present invention includes a Pdcd1 gene that has a nucleotide coding sequence (e.g., a cDNA sequence) at least 50% (e.g., 50%, 55%, 60%, 65%, 70%, 75%, 80%, 85%, 90%, 91%, 92%, 93%, 94%, 95%, 96%, 97%, 98%, 99% or more) identical to a nucleotide coding sequence that appears in a humanized Pdcd1 nucleotide coding sequence of FIG. 8.

In various embodiments, a humanized Pdcd1 mRNA sequence according to the present invention comprises a sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to a humanized mRNA sequence that appears in FIG. 8.

In various embodiments, a humanized Pdcd1 gene according to the present invention encodes a PD-1 polypeptide having an amino acid sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to an amino acid sequence that appears in a PD-1 polypeptide sequence of FIG. 8.

In various embodiments, a humanized PD-1 protein produced by a non-human animal of the present invention has an extracellular portion having an amino acid sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to an extracellular portion of a human PD-1 protein that appears in FIG. 8.

In various embodiments, a humanized PD-1 protein produced by a non-human animal of the present invention has an extracellular portion, which extracellular portion comprises an amino acid sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to amino acid residues 21-170 that appear in a human or humanized PD-1 protein of FIG. 8.

In various embodiments, a humanized PD-1 protein produced by a non-human animal of the present invention has an extracellular portion, which extracellular portion comprises an amino acid sequence that is substantially identical to amino acid residues 21-170 that appear in a human or humanized PD-1 protein of FIG. 8.

In various embodiments, a humanized PD-1 protein produced by a non-human animal of the present invention has an extracellular portion, which extracellular portion comprises an amino acid sequence that is identical to amino acid residues 21-170 that appear in a human or humanized PD-1 protein of FIG. 8.

In various embodiments, a humanized PD-1 protein produced by a non-human animal of the present invention has an extracellular portion, which extracellular portion comprises an amino acid sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to amino acid residues 26-169 that appear in a human or humanized PD-1 protein of FIG. 8.

In various embodiments, a humanized PD-1 protein produced by a non-human animal of the present invention has an extracellular portion, which extracellular portion comprises an amino acid sequence that is substantially identical to amino acid residues 26-169 that appear in a human or humanized PD-1 protein of FIG. 8.

In various embodiments, a humanized PD-1 protein produced by a non-human animal of the present invention has an extracellular portion, which extracellular portion comprises an amino acid sequence that is identical to amino acid residues 26-169 that appear in a human or humanized PD-1 protein of FIG. 8.

In various embodiments, a humanized PD-1 protein produced by a non-human animal of the present invention has an extracellular portion, which extracellular portion comprises an amino acid sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to amino acid residues 27-169 that appear in a human or humanized PD-1 protein of FIG. 8.

In various embodiments, a humanized PD-1 protein produced by a non-human animal of the present invention has an extracellular portion, which extracellular portion comprises an amino acid sequence that is substantially identical to amino acid residues 27-169 that appear in a human or humanized PD-1 protein of FIG. 8.

In various embodiments, a humanized PD-1 protein produced by a non-human animal of the present invention has an extracellular portion, which extracellular portion comprises an amino acid sequence that is identical to amino acid residues 27-169 that appear in a human or humanized PD-1 protein of FIG. 8.

In various embodiments, a humanized PD-1 protein produced by a non-human animal of the present invention has an extracellular portion, which extracellular portion comprises an amino acid sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to amino acid residues 27-145 that appear in a human or humanized PD-1 protein of FIG. 8.

In various embodiments, a humanized PD-1 protein produced by a non-human animal of the present invention has an extracellular portion, which extracellular portion comprises an amino acid sequence that is substantially identical to amino acid residues 27-145 that appear in a human or humanized PD-1 protein of FIG. 8.

In various embodiments, a humanized PD-1 protein produced by a non-human animal of the present invention has an extracellular portion, which extracellular portion comprises an amino acid sequence that is identical to amino acid residues 27-145 that appear in a human or humanized PD-1 protein of FIG. 8.

In various embodiments, a humanized PD-1 protein produced by a non-human animal of the present invention has an extracellular portion, which extracellular portion comprises an amino acid sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to amino acid residues 35-145 that appear in a human or humanized PD-1 protein of FIG. 8.

In various embodiments, a humanized PD-1 protein produced by a non-human animal of the present invention has an extracellular portion, which extracellular portion comprises an amino acid sequence that is substantially identical to amino acid residues 35-145 that appear in a human or humanized PD-1 protein of FIG. 8.

In various embodiments, a humanized PD-1 protein produced by a non-human animal of the present invention has an extracellular portion, which extracellular portion comprises an amino acid sequence that is identical to amino acid residues 35-145 that appear in a human or humanized PD-1 protein of FIG. 8.

In various embodiments, a humanized PD-1 protein produced by a non-human animal of the present invention has an N-terminal immunoglobulin V domain having an amino acid sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to an N-terminal immunoglobulin V domain of a human or humanized PD-1 protein that appears in FIG. 8.

In various embodiments, a humanized PD-1 protein produced by a non-human animal of the present invention has an N-terminal immunoglobulin V domain having an amino acid sequence that is substantially identical to an N-terminal immunoglobulin V domain that appears in a human or humanized PD-1 protein of FIG. 8.

In various embodiments, a humanized PD-1 protein produced by a non-human animal of the present invention has an N-terminal immunoglobulin V domain having an amino acid sequence that is identical to an N-terminal immunoglobulin V domain that appears in a human or humanized PD-1 protein of FIG. 8.

In various embodiments, a humanized PD-1 protein produced by a non-human animal of the present invention has a transmembrane domain having a sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to a transmembrane domain of a mouse PD-1 protein that appears in FIG. 8.

In various embodiments, a humanized PD-1 protein produced by a non-human animal of the present invention has an intracellular tail having a sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to an intracellular tail of a mouse PD-1 protein that appears in FIG. 8.

In various embodiments, a humanized PD-1 protein produced by a non-human animal of the present invention has an amino acid sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to amino acid residues 27-169 (or 26-169) that appear in a human PD-1 protein of FIG. 8.

In various embodiments, a humanized PD-1 protein produced by a non-human animal of the present invention has an amino acid sequence that is substantially identical to amino acid residues 27-169 (or 26-169) that appear in a human PD-1 protein of FIG. 8.

In various embodiments, a humanized PD-1 protein produced by a non-human animal of the present invention has an amino acid sequence that is identical to amino acid residues 27-169 (or 26-169) that appear in a human PD-1 protein of FIG. 8.

In various embodiments, a humanized PD-1 protein produced by a non-human animal of the present invention has an amino acid sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to an amino acid sequence of a humanized PD-1 protein that appears in FIG. 8.

In various embodiments, a humanized PD-1 protein produced by a non-human animal of the present invention has an amino acid sequence that is substantially identical to an amino acid sequence of a humanized PD-1 protein that appears in FIG. 8.

In various embodiments, a humanized PD-1 protein produced by a non-human animal of the present invention has an amino acid sequence that is identical to an amino acid sequence of a humanized PD-1 protein that appears in FIG. 8.

Compositions and methods for making non-human animals that express a humanized PD-1 protein, including specific polymorphic forms, allelic variants (e.g., single amino acid differences) or alternatively spliced isoforms, are provided, including compositions and methods for making non-human animals that express such proteins from a human promoter and a human regulatory sequence. In some embodiments, compositions and methods for making non-human animals that express such proteins from an endogenous promoter and an endogenous regulatory sequence are also provided. In some certain embodiments, endogenous promoters and endogenous regulatory sequences are endogenous rodent promoters and endogenous rodent regulatory sequences. The methods include inserting the genetic material encoding a human PD-1 protein in whole or in part at a precise location in the genome of a non-human animal that corresponds to an endogenous Pdcd1 gene thereby creating a humanized Pdcd1 gene that expresses a PD-1 protein that is human in whole or in part. In some embodiments, the methods include inserting genomic DNA corresponding to exon 2 and exon 3, in whole or in part, of a human PDCD1 gene into an endogenous Pdcd1 gene of the non-human animal thereby creating a humanized gene that encodes a PD-1 protein that contains a human portion containing amino acids encoded by the inserted exons.

Where appropriate, the coding region of the genetic material or polynucleotide sequence(s) encoding a human (or humanized) PD-1 protein in whole or in part may be modified to include codons that are optimized for expression from cells in the non-human animal (e.g., see U.S. Pat. Nos. 5,670,356 and 5,874,304). Codon optimized sequences are synthetic sequences, and preferably encode the identical polypeptide (or a biologically active fragment of a full length polypeptide which has substantially the same activity as the full length polypeptide) encoded by the non-codon optimized parent polynucleotide. In some embodiments, the coding region of the genetic material encoding a human (or humanized) PD-1 protein, in whole or in part, may include an altered sequence to optimize codon usage for a particular cell type (e.g., a rodent cell). For example, the codons of the genomic DNA corresponding to exon 2 and a portion of exon 3 (e.g., 71 bp) of a human PDCD1 gene to be inserted into an endogenous Pdcd1 gene of a non-human animal (e.g., a rodent) may be optimized for expression in a cell of the non-human animal. Such a sequence may be described as a codon-optimized sequence.

A humanized Pdcd1 gene approach employs a relatively minimal modification of the endogenous gene and results in natural PD-1-mediated signal transduction in the non-human animal, in various embodiments, because the genomic sequence of the Pdcd1 sequences are modified in a single fragment and therefore retain normal functionality by including necessary regulatory sequences. Thus, in such embodiments, the Pdcd1 gene modification does not affect other surrounding genes or other endogenous Pdcd1-interacting genes (e.g., PD-L1, PD-L2, etc.). Further, in various embodiments, the modification does not affect the assembly of a functional PD-1 transmembrane protein on the cell membrane and maintains normal effector functions via binding and subsequent signal transduction through the cytoplasmic portion of the protein which is unaffected by the modification.

A schematic illustration (not to scale) of the genomic organization of an endogenous murine Pdcd1 gene and a human PDCD1 gene is provided in FIG. 1. An exemplary method for humanizing an endogenous murine Pdcd1 gene using a genomic fragment containing exon 2 and a portion of exon 3 of a human PDCD1 gene is provided in FIG. 2. As illustrated, an 883 bp genomic DNA fragment containing exon 2 and a portion of exon 3 (e.g., the first 71 bp) of a human PDCD1 gene is inserted into the place of a 900 bp sequence of an endogenous murine Pdcd1 gene locus by a targeting construct. The 883 bp human DNA fragment may be cloned directly from human DNA or synthesized from a source sequence (e.g., Genbank accession no. NM_005018.2). This genomic DNA includes the portion of the gene that encodes substantially all of the extracellular portion (e.g., amino acid residues 27-169 or 26-169) of a human PD-1 protein responsible for ligand binding.

Figure 2:
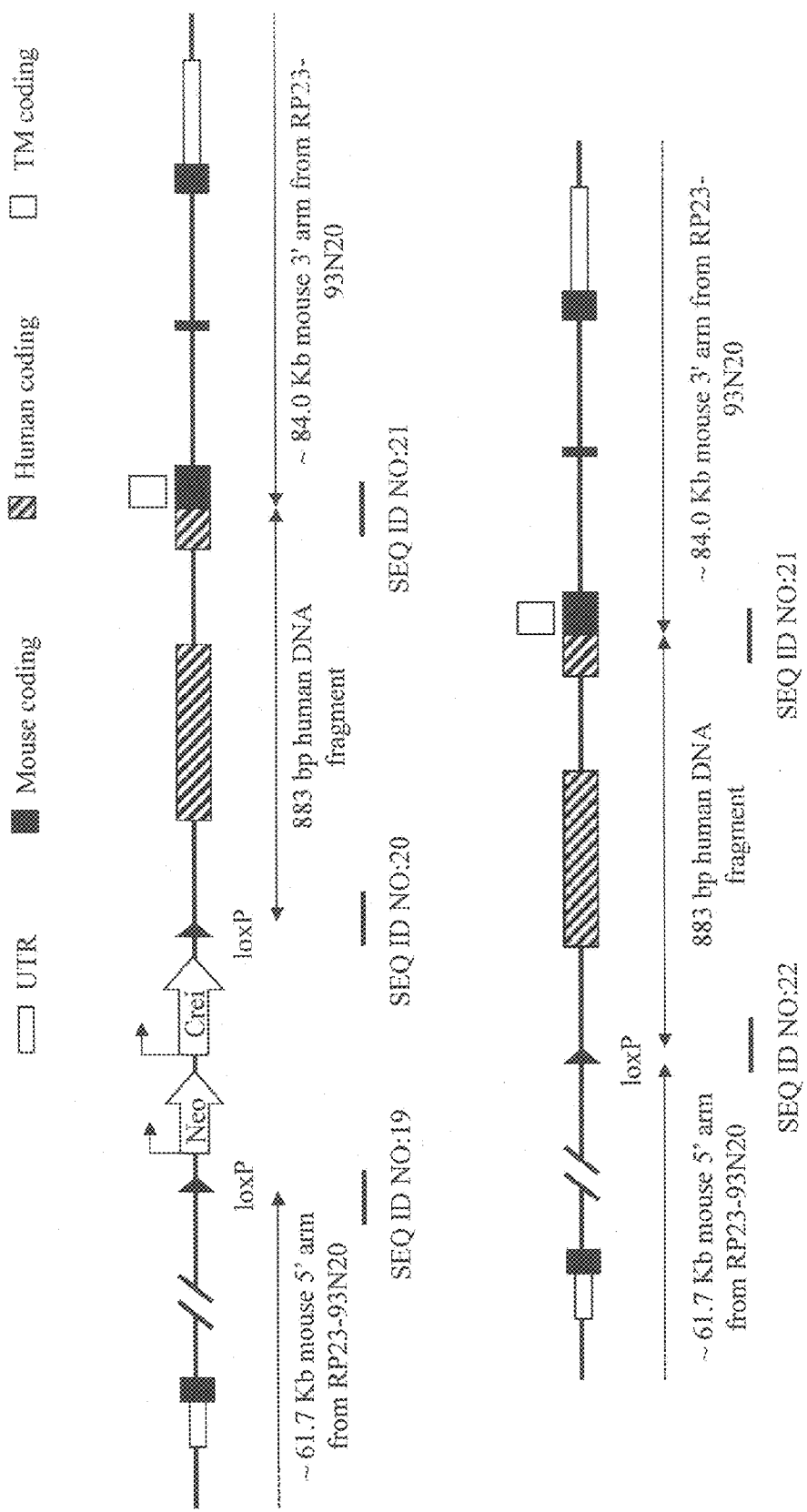
FIG. 2 shows a diagram, not to scale, of an exemplary method for humanization of a non-human Programmed cell death 1 (Pdcd1) gene. Selected nucleotide junction locations are marked with a line below each junction. Sequences of these selected nucleotide junctions are indicated by SEQ ID NOs.

A non-human animal (e.g., a mouse) having a humanized Pdcd1 gene at the endogenous Pdcd1 locus can be made by any method known in the art. For example, a targeting vector can be made that introduces a human Pdcd1 gene in whole or in part with a selectable marker gene. FIG. 2 illustrates a targeting vector that contains an endogenous Pdcd1 locus of a mouse genome comprising an insertion of an 883 bp human DNA fragment that includes exon 2 and the first 71 bp of exon 3 of a human PDCD1 gene. As illustrated, the targeting construct contains a 5' homology arm containing sequence upstream of exon 2 of an endogenous murine Pdcd1 gene (~61.7 Kb), followed by a drug selection cassette (e.g., a neomycin resistance gene flanked on both sides by loxP sequences; ~5 Kb), a genomic DNA fragment containing exon 2 and the first 71 bp of exon 3 of a human Pdcd1 gene (883 bp), and a 3' homology arm containing the remaining sequence of an endogenous murine exon 3 (i.e., portion which encodes a transmembrane portion of a PD-1 protein), exon 4 and exon 5 of an endogenous murine Pdcd1 gene (~84 Kb). The targeting construct contains a self-deleting drug selection cassette (e.g., a neomycin resistance gene flanked by loxP sequences; see U.S. Pat. Nos. 8,697,851, 8,518,392 and 8,354,389, all of which are herein incorporated by reference). Upon electroporation in embryonic stem cells, a modified endogenous Pdcd1 gene is created that exchanges 900 bp of an endogenous wild-type Pdcd1 gene with 883 bp of a human PDCD1 gene (i.e., exon 2 and the first 71 bp of exon 3), which is contained in the targeting vector. A humanized Pdcd1 gene is created resulting in a cell or non-human animal that expresses a humanized PD-1 protein that contains amino acids encoded by the 883 bp human DNA fragment (i.e., exon 2 and 71 bp of exon 3 of a human PDCD1 gene). The drug selection cassette is removed in a development-dependent manner, i.e., progeny derived from mice whose germ line cells containing the humanized Pdcd1 gene described above will shed the selectable marker from differentiated cells during development (see bottom of FIG. 2).

Although embodiments employing a humanized Pdcd1 gene in a mouse (i.e., a mouse with a Pdcd1 gene that encodes a PD-1 protein that includes a human portion and a mouse portion) are extensively discussed herein, other non-human animals that comprise a humanized Pdcd1 gene are also provided. In some embodiments, such non-human animals comprise a humanized Pdcd1 gene operably linked to a rodent Pdcd1 promoter. In some embodiments, such non-human animals comprise a humanized Pdcd1 gene operably linked to an endogenous Pdcd1 promoter; in some embodiments, an endogenous rodent Pdcd1 promoter. In some embodiments, such non-human animals express a humanized PD-1 protein from an endogenous locus, wherein the humanized PD-1 protein comprises amino acid residues 21-170 (or 26-169, or 27-169, 27-145 or 35-145) of a human PD-1 protein. Such non-human animals include any of those which can be genetically modified to express a PD-1 protein as disclosed herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. For example, for those non-human animals for which suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing somatic cell nuclear transfer (SCNT) to transfer the genetically modified genome to a suitable cell, e.g., an enucleated oocyte, and gestating the modified cell (e.g., the modified oocyte) in a non-human animal under suitable conditions to form an embryo.

Methods for modifying a non-human animal genome (e.g., a pig, cow, rodent, chicken, etc. genome) include, e.g., employing a zinc finger nuclease (ZFN) or a transcription activator-like effector nuclease (TALEN) to modify a genome to include a humanized Pdcd1 gene.

In some embodiments, a non-human animal of the present invention is a mammal. In some embodiments, a non-human animal of the present invention is a small mammal, e.g., of the superfamily Dipodoidea or Muroidea. In some embodiments, a genetically modified animal of the present invention is a rodent. In some embodiments, a rodent of the present invention is selected from a mouse, a rat, and a hamster. In some embodiments, a rodent of the present invention is selected from the superfamily Muroidea. In some embodiments, a genetically modified animal of the present invention is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, white-tailed rats, Malagasy rats and mice), Platacanthomyidae (e.g., spiny dormice), and Spalacidae (e.g., mole rats, bamboo rats, and zokors). In some certain embodiments, a genetically modified rodent of the present invention is selected from a true mouse or rat (family Muridae), a gerbil, a spiny mouse, and a crested rat. In some certain embodiments, a genetically modified mouse of the present invention is from a member of the family Muridae. In some embodiment, a non-human animal of the present invention is a rodent. In some certain embodiments, a rodent of the present invention is selected from a mouse and a rat. In some embodiments, a non-human animal of the present invention is a mouse.

In some embodiments, a non-human animal of the present invention is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some certain embodiments, a mouse of the present invention is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129/SvJae, 129S6 (129/SvEvTac), 129S7, 129S8, 129T1, 129T2 (see, e.g., Festing et al., 1999, Mammalian Genome 10:836; Auerbach, W. et al., 2000, Biotechniques 29(5):1024-1028, 1030, 1032). In some certain embodiments, a genetically modified mouse of the present invention is a mix of an aforementioned 129 strain and an aforementioned C57BL/6 strain. In some certain embodiments, a mouse of the present invention is a mix of aforementioned 129 strains, or a mix of aforementioned BL/6 strains. In some certain embodiments, a 129 strain of the mix as described herein is a 129S6 (129/SvEvTac) strain. In some embodiments, a mouse of the present invention is a BALB strain, e.g., BALB/c strain. In some embodiments, a mouse of the present invention is a mix of a BALB strain and another aforementioned strain.

In some embodiments, a non-human animal of the present invention is a rat. In some certain embodiments, a rat of the present invention is selected from a Wistar rat, an LEA strain, a Sprague Dawley strain, a Fischer strain, F344, F6, and Dark Agouti. In some certain embodiments, a rat strain as described herein is a mix of two or more strains selected from the group consisting of Wistar, LEA, Sprague Dawley, Fischer, F344, F6, and Dark Agouti.

Methods Employing Non-Human Animals Having Humanized Pdcd1 Genes

Investigation into PD-1 function has employed the use of various Pdcd1 mutant and transgenic non-human animals (e.g., see Nishimura, H. et al. (1998) Intern. Immunol. 10(10):1563-1572; Nishimura, H. et al. (1999) Immunity 11:141-151; Nishimura, H. et al. (2001) Science 291:319-322; Iwai, Y. et al. (2004) Intern. Immunol. 17(2):133-144; Keir, M. E. et al. (2005) J. Immunol. 175:7372-7379; Keir, M. E. et al. (2007) J. Immunol. 179:5064-5070; Carter, L. L. et al. (2007) J. Neuroimmunol. 182:124-134; Chen, L. et al. (2007) Europ. Soc. Organ Transplant. 21:21-29; Okazaki, T. et al. (2011) J. Exp. Med. 208(2):395-407; U.S. Pat. No. 7,414,171; and European Patent No. 1 334 659 B1; which references are herein incorporated by reference). Such mutant and transgenic animals have been useful in determining the molecular aspects of PD-1 expression, function and regulation of various cellular processes. However, they are not without limitation. For example, PD-1-deficient mice generated by knock-in of a human PD-1 cDNA into exon 1 of a mouse Pdcd1 gene did not express human PD-1 even after stimulation with PMA (Carter, L. L. et al., supra). Further, considerable phenotypic differences among PD-1 mutant animals in different genetic backgrounds has complicated investigation, especially when attempting to assign various functions and/or regulatory activities to PD-1. Still, other transgenic animals have been created that overexpress PD-1 (Chen, L. et al., supra). Such animals have displayed different expression patterns of the transgene, which can reasonably be attributed to construct design. Further, due to the use of the same source genetic material (i.e., mouse), PD-1 overexpression may have corresponded to endogenous PD-1 rather than transgenic PD-1 due to possible position effects of the transgene. While PD-1 transgenic mice have proved useful in elucidating some PD-1-mediated biological function, they have demonstrated variability in the results obtained, which are based, at least in part, from the different approaches employed to make them. Therefore, current in vivo systems exploiting PD-1-mediated biology are incomplete. The molecular aspects of PD-1-mediated biological function and signaling pathways has not been exploited in transgenic mice to its fullest potential.

Non-human animals of the present invention provide an improved in vivo system and source of biological materials (e.g., cells) expressing human (or humanized) PD-1 that are useful for a variety of assays. In various embodiments, non-human animals of the present invention are used to develop therapeutics that target PD-1 and/or modulate PD-1 signaling (e.g., interfering with interactions with PD-L1 and/or PD-L2). In various embodiments, non-human animals of the present invention are used to identify, screen and/or develop candidate therapeutics (e.g., antibodies) that bind human PD-1. In various embodiments, non-human animals of the present invention are used to screen and develop candidate therapeutics (e.g., antibodies) that block interaction of human PD-1 with human PD-L1 and/or human PD-L2. In various embodiments, non-human animals of the present invention are used to determine the binding profile of antagonists and/or agonists of a humanized PD-1 on the surface of a cell of a non-human animal as described herein; in some embodiments, non-human animals of the present invention are used to determine the epitope or epitopes of one or more candidate therapeutic antibodies that bind human PD-1.

In various embodiments, non-human animals of the present invention are used to determine the pharmacokinetic profiles of anti-PD-1 antibodies. In various embodiments, one or more non-human animals of the present invention and one or more control or reference non-human animals are each exposed to one or more candidate therapeutic anti-PD-1 antibodies at various doses (e.g., 0.1 mg/kg, 0.2 mg/kg, 0.3 mg/kg, 0.4 mg/kg, 0.5 mg/kg, 1 mg/kg, 2 mg/kg, 3 mg/kg, 4 mg/kg, 5 mg/mg, 7.5 mg/kg, 10 mg/kg, 15 mg/kg, 20 mg/kg, 25 mg/kg, 30 mg/kg, 40 mg/kg, or 50 mg/kg or more). Candidate therapeutic antibodies may be dosed via any desired route of administration including parenteral and non-parenteral routes of administration. Parenteral routes include, e.g., intravenous, intraarterial, intraportal, intramuscular, subcutaneous, intraperitoneal, intraspinal, intrathecal, intracerebro ventricular, intracranial, intrapleural or other routes of injection. Non-parenteral routes include, e.g., oral, nasal, transdermal, pulmonary, rectal, buccal, vaginal, ocular. Administration may also be by continuous infusion, local administration, sustained release from implants (gels, membranes or the like), and/or intravenous injection. Blood is isolated from non-human animals (humanized and control) at various time points (e.g., 0 hr, 6 hr, 1 day, 2 days, 3 days, 4 days, 5 days, 6 days, 7 days, 8 days, 9 days, 10 days, 11 days, or up to 30 or more days). Various assays may be performed to determine the pharmacokinetic profiles of administered candidate therapeutic antibodies using samples obtained from non-human animals as described herein including, but not limited to, total IgG, anti-therapeutic antibody response, agglutination, etc.

In various embodiments, non-human animals of the present invention are used to measure the therapeutic effect of blocking or modulating PD-1 signaling and the effect on gene expression as a result of cellular changes. In various embodiments, a non-human animal of the present invention or cells isolated therefrom are exposed to a candidate therapeutic that binds a humanized PD-1 protein (or a human portion of a PD-1 protein) on the surface of a cell of the non-human animal and, after a subsequent period of time, analyzed for effects on PD-1-dependent processes, for example, adhesion, apoptosis, cytokine production, inflammation, proliferation, self-tolerance and viral infection (or responses).

Non-human animals of the present invention express humanized PD-1 protein, thus cells, cell lines, and cell cultures can be generated to serve as a source of humanized PD-1 for use in binding and functional assays, e.g., to assay for binding or function of a PD-1 antagonist or agonist, particularly where the antagonist or agonist is specific for a human PD-1 sequence or epitope or, alternatively, specific for a human PD-1 sequence or epitope that associates with PD-L1 and/or PD-L2. In various embodiments, PD-1 epitopes bound by candidate therapeutic antibodies can be determined using cells isolated from non-human animals of the present invention. In various embodiments, a humanized PD-1 protein expressed by a non-human animal as described herein may comprise a variant amino acid sequence. Variant human PD-1 proteins (e.g., polymorphisms) associated with autoimmune and infectious diseases have been reported (e.g., see Lee, Y. H. et al. (2014) Z. Rheumatol. PMID: 24942602; Mansur, A. et al. (2014) J. Investig. Med. 62(3): 638-643; Nasi, M. et al. (2013) Intern. J. Infect. Dis. 17:e845-e850; Piskin, I. E. et al. (2013) Neuropediatrics 44(4):187-190; Carter, L. L. et al. (2007) J. Neuroimmunol. 182(1-2):124-134; Wan, B. et al. (2006) J. Immunol. 177 (12):8844-8850). Exemplary human PD-1 variants include those listed in the SNP GeneView webpage from NCBI and are summarized in Table 3. In various embodiments, non-human animals of the present invention express a humanized PD-1 protein variant. In various embodiments, the variant is polymorphic at an amino acid position associated with ligand binding. In various embodiments, non-human animals of the present invention are used to determine the effect of ligand binding through interaction with a polymorphic variant of human PD-1. In some certain embodiments, non-human animals of the present invention express a human PD-1 variant that appears in Table 3.

TABLE 3

| Chromosome position | mRNA position | Variant ID No. | Allele | Amino acid | Codon position | Amino acid position |
|---|---|---|---|---|---|---|
| 241851110 | 883 | rs372765600 | A | Gln [Q] | 2 | 272 |
|  |  |  | G | Arg [R] | 2 | 272 |
| 241851118 | 875 | rs368411538 | T | Asp [D] | 3 | 269 |
|  |  |  | C | Asp [D] | 3 | 269 |
| 241851121 | 872 | rs2227981 | A | Ala [A] | 3 | 268 |
|  |  |  | C | Ala [A] | 3 | 268 |
|  |  |  | G | Ala [A] | 3 | 268 |
|  |  |  | T | Ala [A] | 3 | 268 |
| 241851135 | 858 | rs146642159 | T | Cys [C] | 1 | 264 |
|  |  |  | C | Arg [R] | 1 | 264 |
| 241851138 | 855 | rs143359677 | A | Thr [T] | 1 | 263 |
|  |  |  | G | Ala [A] | 1 | 263 |
| 241851160 | 833 | rs141228784 | T | Ser [S] | 3 | 255 |
|  |  |  | C | Ser [S] | 3 | 255 |
| 241851163 | 830 | rs200434733 | C | Pro [P] | 3 | 254 |
|  |  |  | T | Pro [P] | 3 | 254 |
| 241851171 | 822 | rs201961957 | A | Ile [I] | 1 | 252 |
|  |  |  | G | Val [V] | 1 | 252 |
| 241851188 | 805 | rs201540918 | T | Met [M] | 2 | 246 |
|  |  |  | C | Thr [T] | 2 | 246 |
| 241851190 | 803 | rs201481671 | A | Gln [Q] | 3 | 245 |
|  |  |  | G | Gln [Q] | 3 | 245 |
| 241851210 | 783 | rs137861407 | A | Met [M] | 1 | 239 |
|  |  |  | G | Val [V] | 1 | 239 |
| 241851220 | 773 | rs370462869 | A | Pro [P] | 3 | 235 |
|  |  |  | G | Pro [P] | 3 | 235 |
| 241851237 | 756 | rs147213978 | C | Arg [R] | 1 | 230 |
|  |  |  | T | Trp [W] | 1 | 230 |
| 241851264 | 729 | rs373940258 | A | Met [M] | 1 | 221 |
|  |  |  | G | Val [V] | 1 | 221 |
| 241851274 | 719 | rs373831349 | G | Pro [P] | 3 | 217 |
|  |  |  | T | Pro [P] | 3 | 217 |
| 241851279 | 714 | rs376257658 | A | Met [M] | 1 | 216 |
|  |  |  | G | Val [V] | 1 | 216 |
| 241851281 | 712 | rs2227982 | T | Val [V] | 2 | 215 |
|  |  |  | C | Ala [A] | 2 | 215 |

TABLE 3-continued

| Chromosome position | mRNA position | Variant ID No. | Allele | Amino acid | Codon position | Amino acid position |
|---|---|---|---|---|---|---|
| 241851954 | 690 | rs148456597 | A | Thr [T] | 1 | 208 |
|  |  |  | C | Pro [P] | 1 | 208 |
| 241851961 | 683 | rs146821282 | G | Thr [T] | 3 | 205 |
|  |  |  | T | Thr [T] | 3 | 205 |
|  |  |  | C | Thr [T] | 3 | 205 |
| 241852204 | 654 | rs144217487 | A | Thr [T] | 1 | 196 |
|  |  |  | G | Ala [A] | 1 | 196 |
| 241852205 | 653 | rs141119263 | T | Ala [A] | 3 | 195 |
|  |  |  | C | Ala [A] | 3 | 195 |
| 241852209 | 649 | rs200312345 | A | Gln [Q] | 2 | 194 |
|  |  |  | G | Arg [R] | 2 | 194 |
| 241852258 | 600 | rs55667829 | T | Leu [L] | 1 | 178 |
|  |  |  | C | Leu [L] | 1 | 178 |
| 241852271 | 587 | rs377191240 | T | Val [V] | 3 | 173 |
|  |  |  | C | Val [V] | 3 | 173 |
| 241852310 | 548 | rs370660750 | G | Pro [P] | 3 | 160 |
|  |  |  | C | Pro [P] | 3 | 160 |
| 241852644 | 481 | rs138031190 | A | Gln [Q] | 2 | 138 |
|  |  |  | T | Leu [L] | 2 | 138 |
| 241852658 | 467 | rs374762232 | A | Gln [Q] | 3 | 133 |
|  |  |  | G | Gln [Q] | 3 | 133 |
| 241852661 | 464 | rs41400345 | A | Ala [A] | 3 | 132 |
|  |  |  | G | Ala [A] | 3 | 132 |
| 241852691 | 434 | rs367833850 | T | Leu [L] | 3 | 122 |
|  |  |  | C | Leu [L] | 3 | 122 |
| 241852697 | 428 | rs186074812 | T | Thr [T] | 3 | 120 |
|  |  |  | C | Thr [T] | 3 | 120 |
| 241852715 | 410 | rs141299049 | A | Arg [R] | 3 | 114 |
|  |  |  | G | Arg [R] | 3 | 114 |
| 241852716 | 409 | rs55679128 | A | Gln [Q] | 2 | 114 |
|  |  |  | G | Arg [R] | 2 | 114 |
| 241852720 | 405 | rs200323895 | A | Thr [T] | 1 | 113 |
|  |  |  | G | Ala [A] | 1 | 113 |
| 241852729 | 396 | rs190602950 | A | Met [M] | 1 | 110 |
|  |  |  | G | Val [V] | 1 | 110 |
| 241852730 | 395 | rs370268595 | T | Ser [S] | 3 | 109 |
|  |  |  | C | Ser [S] | 3 | 109 |
| 241852743 | 382 | rs368009835 | G | Gly [G] | 2 | 105 |
|  |  |  | A | Asp [D] | 2 | 105 |
| 241852746 | 379 | rs138016578 | A | His [H] | 2 | 104 |
|  |  |  | G | Arg [R] | 2 | 104 |
| 241852750 | 375 | rs56124337 | A | Arg [R] | 1 | 103 |
|  |  |  | G | Gly [G] | 1 | 103 |
| 241852751 | 374 | rs55637807 | T | Asn [N] | 3 | 102 |
|  |  |  | C | Asn [N] | 3 | 102 |
| 241852755 | 370 | rs371902970 | T | Leu [L] | 2 | 101 |
|  |  |  | C | Pro [P] | 2 | 101 |
| 241852788 | 337 | rs144257658 | T | Val [V] | 2 | 90 |
|  |  |  | G | Gly [G] | 2 | 90 |
| 241852808 | 317 | rs55804130 | T | Pro [P] | 3 | 83 |
|  |  |  | C | Pro [P] | 3 | 83 |
| 241852817 | 308 | rs373755187 | A | Ala [A] | 3 | 80 |
|  |  |  | T | Ala [A] | 3 | 80 |
|  |  |  | C | Ala [A] | 3 | 80 |
| 241852860 | 265 | rs28615468 | C | Thr [T] | 2 | 66 |
|  |  |  | A | Asn [N] | 2 | 66 |
| 241852866 | 259 | rs142434414 | G | Gly [G] | 2 | 64 |
|  |  |  | T | Val [V] | 2 | 64 |
| 241852877 | 248 | rs181904226 | A | Ser [S] | 3 | 60 |
|  |  |  | G | Ser [S] | 3 | 60 |
| 241852892 | 233 | rs55993679 | T | Ser [S] | 3 | 55 |
|  |  |  | C | Ser [S] | 3 | 55 |
| 241852904 | 221 | rs373582646 | G | Thr [T] | 3 | 51 |
|  |  |  | C | Thr [T] | 3 | 51 |
| 241852910 | 215 | rs141718335 | T | Asn [N] | 3 | 49 |
|  |  |  | C | Asn [N] | 3 | 49 |
| 241852922 | 203 | rs374726495 | T | Thr [T] | 3 | 45 |
|  |  |  | C | Thr [T] | 3 | 45 |
| 241852928 | 197 | rs147586902 | C | Val [V] | 3 | 43 |
|  |  |  | G | Val [V] | 3 | 43 |
| 241852930 | 195 | rs368829632 | A | Met [M] | 1 | 43 |
|  |  |  | G | Val [V] | 1 | 43 |
| 241852951 | 174 | rs373081859 | G | Ala [A] | 1 | 36 |
|  |  |  | A | Thr [T] | 1 | 36 |

TABLE 3-continued

| Chromosome position | mRNA position | Variant ID No. | Allele | Amino acid | Codon position | Amino acid position |
|---|---|---|---|---|---|---|
| 241852952 | 173 | rs41444844 | G | Pro [P] | 3 | 35 |
|  |  |  | C | Pro [P] | 3 | 35 |
| 241852974 | 151 | rs56234260 | T | Leu [L] | 2 | 28 |
|  |  |  | C | Pro [P] | 2 | 28 |
| 241858780 | 127 | rs368550965 | A | Gln [Q] | 2 | 20 |
|  |  |  | G | Arg [R] | 2 | 20 |
| 241858800 | 107 | rs370111035 | A | Ala [A] | 3 | 13 |
|  |  |  | G | Ala [A] | 3 | 13 |
| 241858808 | 99 | rs142544044 | A | Ile [I] | 1 | 11 |
|  |  |  | G | Val [V] | 1 | 11 |

Cells from non-human animals of the present invention can be isolated and used on an ad hoc basis, or can be maintained in culture for many generations. In various embodiments, cells from a non-human animal of the present invention are immortalized (e.g., via use of a virus) and maintained in culture indefinitely (e.g., in serial cultures).

In various embodiments, cells and/or non-human animals of the present invention are used in various immunization regimens to determine the PD-1-mediated functions in the immune response to an antigen. In some embodiments, candidate therapeutics that bind to, or block one or more functions of, human (or humanized) PD-1 are characterized in a non-human animal of the present invention. Suitable measurements include various cellular assays, proliferation assays, serum immunoglobulin analysis (e.g., antibody titer), cytotoxicity assays, characterization of ligand-receptor interactions (e.g., immunoprecipitation assays). In some embodiments, non-human animals of the present invention are used to characterize the PD-1-mediated functions regulating an immune response to an antigen. In some embodiments, the antigen is associated with an autoimmune disease, disorder or condition. In some embodiments, the antigen is associated with an inflammatory disease, disorder or condition. In some embodiments, the antigen is a test antigen (e.g., ovalbumin or OVA). In some embodiments, the antigen is a target associated with a disease or condition suffered by one or more human patients in need of treatment.

In various embodiments, non-human animals of the present invention are used in serum assays for determining titers of autoantibody production for testing the pharmaco-toxicological aspects of candidate therapeutics that target human PD-1. In some embodiments, autoantibody production in non-human animals of the present invention results from one or more autoimmune diseases, disorders or conditions induced in the non-human animal.

In various embodiments, non-human animals of the present invention are used for challenge with one or more antigens to determine the therapeutic potential of compounds or biological agents to modulate PD-1-dependent regulation of an immune response, including but not limited to, the specific T cell-dependent and B cell-dependent responses to a given antigen.

In various embodiments, cells and/or non-human animals of the present invention are used in a survival and/or proliferation assay (e.g., employing B or T cells) to screen and develop candidate therapeutics that modulate human PD-1 signaling Activation or loss of PD-1 plays an important role in the regulation of T cell responses, and regulation of self-tolerance by PD-1 may result from the activation of specific epitopes of the extracellular domain of PD-1, therefore, candidate PD-1 modulators (e.g., antagonists or agonists) may be identified, characterized and developed using cells of non-human animals of the present invention and/or a non-human animal as described herein. In some embodiments, cells and/or non-human animals of the present invention are used in survival or death assay(s) to determine the effect on proliferation or apoptosis of a specific cell(s) (e.g., cancer cells) in the presence and absence of PD-1.

In various embodiments, cells and/or non-human animals of the present invention are used in xenotransplantation of heterologous (e.g., human) cells or tissue to determine the PD-1-mediated functions in the physiological (e.g., immune) response to the transplanted human cells or tissue. In some embodiments, candidate therapeutics that bind, or block one or more functions of, human PD-1 are characterized in a non-human animal of the present invention. Suitable measurements include various cellular assays, proliferation assays, serum immunoglobulin analysis (e.g., antibody titer), cytotoxicity assays, and characterization of ligand-receptor interactions (immunoprecipitation assays). In some embodiments, non-human animals of the present invention are used to characterize the PD-1-mediated functions regulating an immune response to an antigen. In some embodiments, the antigen is associated with a neoplasm. In some embodiments, the antigen is associated with an autoimmune disease, disorder or condition. In some embodiments, the antigen is associated with an inflammatory disease, disorder or condition. In some embodiments, the antigen is a target associated with a disease or condition suffered by one or more human patients in need of treatment.

In various embodiments, non-human animals of the present invention are used in transplantation or adoptive transfer experiments to determine the therapeutic potential of compounds or biological agents to modulate PD-1-dependent regulation of new lymphocytes and their immune function. In various embodiments, non-human animals of the present invention are transplanted with human T cells; in some embodiments, naïve T cells; in some embodiments, activated T cells.

In various embodiments, cells of non-human animals of the present invention are used to in T cell assays to determine the therapeutic potential of compounds or biological agents to modulate PD-1-dependent regulation of T cell-dependent response and function. Exemplary T cell assays include, but are not limited to, ELISpot, intracellular cytokine staining, major histocompatibility complex (MHC) restriction, viral suppression assays, cytotoxicity assays, proliferation assays and regulatory T cell suppression assays.

In various embodiments, cells of non-human animals of the present invention are used in a cell transmigration assay to screen and develop candidate therapeutics that modulate human PD-1. Cell transmigration involves the migration of cells across the endothelium and transmigration assays permit the measurement of interactions with, and transmigration of, the endothelium by leukocytes or tumor cells.

In various embodiments, cells of non-human animals of the present invention are used in tumor cell growth (or proliferation) assays to determine the therapeutic potential of compounds or biological agents to modulate PD-1-dependent regulation and/or apoptosis of tumor cells.

In various embodiments, cells of non-human animals of the present invention are used in cytokine production assays to determine the therapeutic potential of compounds or biological agents to modulate PD-1-dependent regulation of cytokine release from T cells. In some embodiments, cells of non-human animals of the present invention are used for detection (and/or measurement) of intracellular cytokine release resulting from interaction of humanized PD-1 with a drug targeting human PD-1 or a PD-1 ligand (e.g., PD-L1 or PD-L2).

In various embodiments, an autoimmune disease, disorder or condition is induced in one or more non-human animals of the present invention to provide an in vivo system for determining the therapeutic potential of compounds or biological agents to modulate PD-1-dependent regulation of one or more functions of the autoimmune disease, disorder or condition. Exemplary autoimmune diseases, disorders or conditions that may be induced in one or more non-human animals of the present invention include diabetes, experimental autoimmune encephalomyelitis (e.g., a model for multiple sclerosis), rheumatoid arthritis, and systemic lupus erythematosus.

Non-human animals of the present invention provide an in vivo system for the analysis and testing of a drug or vaccine. In various embodiments, a candidate drug or vaccine may be delivered to one or more non-human animals of the present invention, followed by monitoring of the non-human animals to determine one or more of the immune response to the drug or vaccine, the safety profile of the drug or vaccine, or the effect on a disease or condition. In some embodiments, the vaccine targets a virus such as, for example, human immunodeficiency virus or hepatitis virus (e.g. HCV). Exemplary methods used to determine the safety profile include measurements of toxicity, optimal dose concentration, efficacy of the drug or vaccine, and possible risk factors. Such drugs or vaccines may be improved and/or developed in such non-human animals.

Non-human animals of the present invention provide an in vivo system for assessing the pharmacokinetic properties of a drug targeting human PD-1. In various embodiments, a drug targeting human PD-1 may be delivered or administered to one or more non-human animals of the present invention, followed by monitoring of, or performing one or more assays on, the non-human animals (or cells isolated therefrom) to determine the effect of the drug on the non-human animal. Pharmacokinetic properties include, but are not limited to, how an animal processes the drug into various metabolites (or detection of the presence or absence of one or more drug metabolites, including, toxic metabolites), drug half-life, circulating levels of drug after administration (e.g., serum concentration of drug), anti-drug response (e.g., anti-drug antibodies), drug absorption and distribution, route of administration, routes of excretion and/or clearance of the drug. In some embodiments, pharmacokinetic and pharmacodynamic properties of drugs (e.g., PD-1 modulators) are monitored in or through the use of non-human animals of the present invention.

Non-human animals of the present invention provide an in vivo system for assessing the on-target toxicity of a drug targeting human PD-1. In various embodiments, a drug targeting human PD-1 may be delivered or administered to one or more non-human animals of the present invention, followed by monitoring of or performing one or more assays on the non-human animals (or cells isolated therefrom) to determine the on-target toxic effect of the drug on the non-human animal. Typically, drugs are intended to modulate one or more functions of their targets. To give but one example, a PD-1 modulator is intended to modulate PD-1-mediated functions (e.g., PD-1 signal transduction) through interacting in some way with the PD-1 molecule on the surface of one or more cells. In some embodiments, such a modulator may have an adverse effect that is an exaggeration of the desired pharmacologic action(s) of the modulator. Such effects are termed on-target effects. Exemplary on-target effects include too high of a dose, chronic activation/inactivation, and correct action in an incorrect tissue. In some embodiments, on-target effects of a drug targeting PD-1 identified in or through the use of non-human animals of the present invention are used to determine a previously unknown function(s) of PD-1.

Non-human animals of the present invention provide an in vivo system for assessing the off-target toxicity of a drug targeting human PD-1. In various embodiments, a drug targeting human PD-1 may be delivered or administered to one or more non-human animals of the present invention, followed by monitoring of or performing one or more assays on the non-human animals (or cells isolated therefrom) to determine the off-target toxic effect of the drug on the non-human animal. Off-target effects can occur when a drug interacts with an unintended target (e.g., cross-reactivity to a common epitope). Such interactions can occur in an intended or unintended tissue. To give but one example, mirror image isomers (enantiomers) of a drug can lead to off-target toxic effects. Further, a drug can inappropriately interact with and unintentionally activate different receptor subtypes. Exemplary off-target effects include incorrect activation/inhibition of an incorrect target regardless of the tissue in which the incorrect target is found. In some embodiments, off-target effects of a drug targeting human PD-1 are determined by comparing the effects of administering the drug to non-human animals of the present invention to one or more reference non-human animals.

In some embodiments, performing an assay includes determining the effect on the phenotype and/or genotype of the non-human animal to which the drug is administered. In some embodiments, performing an assay includes determining lot-to-lot variability for a PD-1 modulator (e.g., an antagonist or an agonist). In some embodiments, performing an assay includes determining the differences between the effects of a drug targeting PD-1 administered to a non-human animal of the present invention and a reference non-human animal. In various embodiments, reference non-human animals may have a modification as described herein, a modification that is different as described herein (e.g., one that has a disruption, deletion or otherwise non-functional Pdcd1 gene) or no modification (i.e., a wild-type non-human animal).

Exemplary parameters that may be measured in non-human animals (or in and/or using cells isolated therefrom) for assessing the pharmacokinetic properties, on-target toxicity, and/or off-target toxicity of a drug targeting human PD-1 include, but are not limited to, agglutination, autophagy, cell division, cell death, complement-mediated hemolysis, DNA integrity, drug-specific antibody titer, drug metabolism, gene expression arrays, metabolic activity, mitochondrial activity, oxidative stress, phagocytosis, protein biosynthesis, protein degradation, protein secretion, stress response, target tissue drug concentration, non-target tissue drug concentration, transcriptional activity and the like. In various embodiments, non-human animals of the present invention are used to determine a pharmaceutically effective dose of a PD-1 modulator.

Non-human animals of the present invention provide an improved in vivo system for the development and characterization of candidate therapeutics for use in cancer. In various embodiments, non-human animals of the present invention may be implanted with a tumor, followed by administration of one or more candidate therapeutics. In some embodiments, candidate therapeutics may include a multi-specific antibody (e.g., a bi-specific antibody) or an antibody cocktail; in some embodiments, candidate therapeutics include combination therapy such as, for example, administration of mono-specific antibodies dosed sequentially or simultaneously. The tumor may be allowed sufficient time to be established in one or more locations within the non-human animal. Tumor cell proliferation, growth, survival, etc. may be measured both before and after administration with the candidate therapeutic(s). Cytoxicity of candidate therapeutics may also be measured in the non-human animal as desired.

Non-human animals of the present invention may be used to develop one or more disease models to evaluate or assess candidate therapeutics and/or therapeutic regimens (e.g., monotherapy, combination therapy, dose range testing, etc.) to effectively treat diseases, disorders or conditions that affect humans. Various disease conditions may be established in non-human animals of the present invention followed by administration of one or more candidate molecules (e.g., drugs targeting PD-1) so that efficacy of the one or more candidate molecules in a disease condition can determined. In some embodiments, disease models include autoimmune, inflammatory and/or neoplastic diseases, disorders or conditions.

To give but one example, non-human animals of the present invention provide an improved animal model for prophylactic and/or therapeutic treatment of a tumor or tumor cells. In various embodiments, non-human animals of the present invention may be implanted with one or more tumor cells, followed by administration of one or more candidate therapeutics (e.g., antibodies). In some embodiments, administration of one or more candidate therapeutics is performed subsequent to (e.g., minutes or hours but typically on the same day as) implantation of one or more tumor cells and one or more candidate therapeutics are evaluated in non-human animals of the present invention for efficacy in preventing establishment of a solid tumor and/or growth of tumor cells in said non-human animals. In some embodiments, administration of one or more candidate therapeutics is performed subsequent to (e.g., days after) implantation of one or more tumor cells and, in some certain embodiments, after a sufficient time such that one or more implanted tumor cells have reached a predetermined size (e.g., volume) in non-human animals of the present invention; and one or more candidate therapeutics are evaluated for efficacy in treatment of one or more established tumors. Non-human animals may be placed into different treatment groups according to dose so that an optimal dose or dose range that correlates to effective treatment of an established tumor can be determined.

Candidate molecules can be administered to non-human animal disease models using any method of administration including parenteral and non-parenteral routes of administration. Parenteral routes include, e.g., intravenous, intraarterial, intraportal, intramuscular, subcutaneous, intraperitoneal, intraspinal, intrathecal, intracerebroventricular, intracranial, intrapleural or other routes of injection. Non-parenteral routes include, e.g., oral, nasal, transdermal, pulmonary, rectal, buccal, vaginal, ocular. Administration may also be by continuous infusion, local administration, sustained release from implants (gels, membranes or the like), and/or intravenous injection. When a combination therapy is evaluated in non-human animals of the present invention, candidate molecules can be administered via the same administration route or via different administration routes. When a dosing regimen is evaluated in non-human animals of the present invention, candidate molecules may be administered at bimonthly, monthly, triweekly, biweekly, weekly, daily, at variable intervals and/or in escalating concentrations to determine a dosing regimen that demonstrates a desired therapeutic or prophylactic effect in a non-human animal in which one or more disease models has been established.

Non-human animals of the present invention provide an improved in vivo system for the development and characterization of candidate therapeutics for use in infectious diseases. In various embodiments, non-human animals of the present invention may be infected by injection with a virus (e.g., MHV, HIV, HCV, etc.) or pathogen (e.g., bacteria), followed by administration of one or more candidate therapeutics. In some embodiments, candidate therapeutics may include a multi-specific antibody (e.g., a bi-specific antibody) or an antibody cocktail; in some embodiments, candidate therapeutics include combination therapy such as, for example, administration of mono-specific antibodies dosed sequentially or simultaneously; in some embodiments, candidate therapeutics may include a vaccine. The virus or pathogen may be allowed sufficient time to be established in one or more locations or cells within the non-human animal so that one or more symptoms associated with infection of the virus or pathogen develop in the non-human animal. T cell proliferation and growth may be measured both before and after administration with the candidate therapeutic(s). Further, survival, serum and/or intracellular cytokine analysis, liver and/or spleen histopathology may be measured in non-human animals infected with the virus or pathogen. In some embodiments, non-human animals of the present invention are used to determine the extent of organ damage associated with viral infection. In some embodiments, non-human animals of the present invention are used to determine the cytokine expression profile in various organs of non-human animals infected with a particular virus.

Non-human animals of the present invention can be employed to assess the efficacy of a therapeutic drug targeting human cells. In various embodiments, a non-human animal of the present invention is transplanted with human cells, and a drug candidate targeting such human cells is administered to such non-human animal. The therapeutic efficacy of the drug is then determined by monitoring the human cells in the non-human animal after the administration of the drug. Drugs that can be tested in the non-human animals include both small molecule compounds, i.e., compounds of molecular weights of less than 1500 kD, 1200 kD, 1000 kD, or 800 daltons, and large molecular compounds (such as proteins, e.g., antibodies), which have intended therapeutic effects for the treatment of human diseases and conditions by targeting (e.g., binding to and/or acting on) human cells.

In some embodiments, the drug is an anti-cancer drug, and the human cells are cancer cells, which can be cells of a primary cancer or cells of cell lines established from a primary cancer. In these embodiments, a non-human animal of the present invention is transplanted with human cancer cells, and an anti-cancer drug is given to the non-human animal. The efficacy of the drug can be determined by assessing whether growth or metastasis of the human cancer cells in the non-human animal is inhibited as a result of the administration of the drug.

In specific embodiments, the anti-cancer drug is an antibody molecule, which binds an antigen on human cancer cells. In particular embodiments, the anti-cancer drug is a bi-specific antibody that binds to an antigen on human cancer cells, and to an antigen on other human cells, for example, cells of the human immune system (or "human immune cells") such as B cells and T cells.

EXAMPLES

The following examples are provided so as to describe to those of ordinary skill in the art how to make and use methods and compositions of the invention, and are not intended to limit the scope of what the inventors regard as their invention. Unless indicated otherwise, temperature is indicated in Celsius, and pressure is at or near atmospheric.

Example 1

Humanization of an Endogenous Programmed Cell Death 1 (Pdcd1) Gene

This example illustrates exemplary methods of humanizing an endogenous Pdcd1 gene encoding Programmed cell death protein 1 (PD-1) in a non-human mammal such as a rodent (e.g., a mouse). The methods described in this example can be employed to humanize an endogenous Pdcd1 gene of a non-human animal using any human sequence, or combination of human sequences (or sequence fragments) as desired. In this example, an ~883 bp human DNA fragment containing exon 2, intron 2, and the first 71 bp of exon 3 of a human PDCD1 gene that appears in GenBank accession NM_005018.2 (SEQ ID NO:23) is employed for humanizing an endogenous Pdcd1 gene of a mouse. A targeting vector for humanization of the genetic material encoding an extracellular N-terminal IgV domain, of an endogenous Pdcd1 gene was constructed using VELOCIGENE® technology (see, e.g., U.S. Pat. No. 6,586,251 and Valenzuela et al., 2003, Nature Biotech. 21(6):652-659; herein incorporated by reference).

Briefly, mouse bacterial artificial chromosome (BAC) clone RP23-93N20 (Invitrogen) was modified to delete the sequence containing exon 2, intron 2 and part of exon 3 of an endogenous Pdcd1 gene and insert exon 2, intron 2 and part of exon 3 of a human PDCD1 gene using an ~883 bp human DNA fragment, which encodes amino acids 26-169 of a human PD-1 polypeptide. Endogenous DNA containing exon 1, portion of exon 3 (i.e., that encodes the transmembrane domain), 4 and 5 as well as the 5' and 3' untranslated regions (UTRs) were retained. Sequence analysis of the ~883 bp human DNA fragment confirmed all human PDCD1 exons (i.e., exon 2 and 71 bp of exon 3) and splicing signals. Sequence analysis revealed that the sequence matched the reference genome and PDCD1 transcript NM_005018.2.

In more detail, first, a small bacterial homologous recombination donor was constructed from a synthetic DNA fragment containing the following: [(HindIII)-(mouse upstream 78 bp)-(XhoI/NheI restriction enzyme sites)-(human PDCD1 883 bp)-(mouse downstream 75 bp)-(HindIII)].

This fragment was synthesized by Genescript Inc. (Piscataway, N.J.) and cloned into an ampicillin-resistant plasmid vector. The XhoI-NheI sites were employed to ligate a ~4,996 bp self-deleting neomycin cassette flanked by recombinase recognition sites (loxP-hUb1-em7-Neo-pA-mPrm1-Crei-loxP; see U.S. Pat. Nos. 8,697,851, 8,518,392 and 8,354,389, which are herein incorporated by reference). Subsequent selection employed neomycin. The flanking HindIII sites were used to linearize the targeting vector prior to homologous recombination with mouse BAC clone RP23-93N20. By design, the junction between the Human PDCD1 883 bp fragment and the mouse downstream 75 bp preserved the open reading frame in exon 3 (FIG. 2). The resulting targeting vector contained, from 5' to 3', a 5' homology arm containing ~61.7 kb of mouse genomic DNA from BAC clone RP23-93N20, a self-deleting neomycin cassette flanked by loxP sites, an 883 bp human genomic DNA fragment (containing exon 2 through the first 71 bp of exon 3 of a human Pdcd1 gene) and ~84 kb of mouse genomic DNA from BAC clone RP23-93N20.

Figure 3:
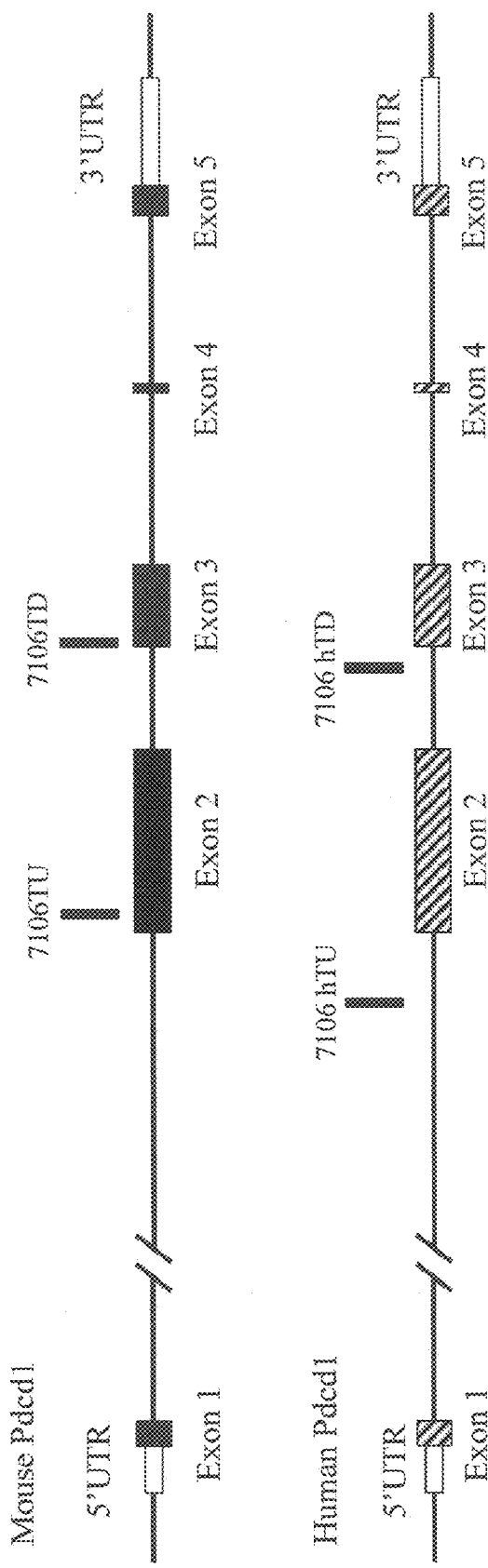
FIG. 3 shows a diagram, not to scale, of the genomic organization of a mouse and human Programmed cell death 1 (Pdcd1) genes indicating the approximate locations of probes used in an assay described in Example 1.

The modified RP23-93N20 BAC clone described above was used to electroporate mouse embryonic stem (ES) cells to create modified ES cells comprising an endogenous Pdcd1 gene that is humanized from exon 2 through to part of exon 3 (i.e., deletion of 900 bp of the endogenous Pdcd1 gene and insertion of 883 bp of human sequence). Positively targeted ES cells containing a humanized Pdcd1 gene were identified by an assay (Valenzuela et al., supra) that detected the presence of the human PDCD1 sequences (e.g., exon 2 and part of exon 3) and confirmed the loss and/or retention of mouse Pdcd1 sequences (e.g., exon 2 and part of exon 3, and/or exons 1, 4 and 5). Table 4 sets forth the primers and probes that were used to confirm humanization of an endogenous Pdcd1 gene as described above (FIG. 3). The nucleotide sequence across the upstream insertion point included the following, which indicates endogenous mouse sequence (contained within the parentheses below with an XhoI restriction site italicized) upstream of the 5' end of self-deleting neomycin cassette of the insertion point linked contiguously to a loxP site (bolded) and cassette sequence present at the insertion point: (TCAAAGGACA GAATAG-TAGC CTCCAGACCC TAGGTTCAGT TATGCTGAAG GAAGAGCCCT CTCGAG)ATAACTTCGT ATAATG-TATG CTATACGAAG TTATATGCAT GGCCTCCGCG CCGGGTTTTG GCGCCTCCCG CGGGCGCCCC CCTC-CTCACG (SEQ ID NO:19). The nucleotide sequence across the downstream insertion point at the 3' end of the self-deleting neomycin cassette included the following, which indicates cassette sequence (contained within the parentheses below with loxP sequence bolded and an NheI restriction site italicized) contiguous with human Pdcd1 genomic sequence downstream of the insertion point: (CTG-GAATAAC TTCGTATAAT GTATGCTATA CGAAGT-TATG CTAGTAACTA TAACGGTCCT AAGGTAGCGA GCTAGC) AAGAGGCTCT GCAGTGGAGG CCAGTGC-CCA TCCCCGGGTG GCAGAGGCCC CAGCAGAGAC TTCTCAATGA CATTCCAGCT GGGGTGGCCC TTC-CAGAGCC CTTGCTGCCC GAGGGATGTG AGCAG-GTGGC CGGGGAGGCT TTGTGGGGCC ACCCAGC-CCC (SEQ ID NO:20). The nucleotide sequence across the downstream insertion point at the 3' end of the human PDCD1 genomic sequence included the following, which indicates human PDCD1 sequence contiguous with mouse Pdcd1 genomic sequence (contained within the parentheses below): CCCTTCCAGA GAGAAGGGCA GAAGTGC-CCA CAGCCCACCC CAGCCCCTCA CCCAGGCCAG CCGGCCAGTT CCAAACCCTG (GTCATTGGTA TCAT- GAGTGC CCTAGTGGGT ATCCCTGTAT TGCTGCT-GCT GGCCTGGGCC CTAGCTGTCT TCTGCTCAAC) (SEQ ID NO:21). The nucleotide sequence across the upstream insertion point after deletion of the neomycin cassette (77 bp remaining) included the following, which indicates mouse and human genomic sequence juxtaposed with remaining cassette sequence loxP sequence (contained within the parentheses below with XhoI and NheI restriction sites italicized and loxP sequence in bold): TCAAAGGACA GAATAGTAGC CTCCAGACCC TAGGTTCAGT TAT-GCTGAAG GAAGAGCCCT (CTCGAG ATAACTTCGT ATAATGTATG CTATACGAAG TTATGCTAGT AAC-TATAACG GTCCTAAGGT AGCGA GCTAGC) AAGAG GCTCTGCAGT GGAGGCCAGT GCCCATCCCC GGGTGGCAGA GGCCCCAGCA GAGACTTCTC AAT-GACATTC CAGCTGGGGT GGCCCTTCCA (SEQ ID NO:22).

Positive ES cell clones were then used to implant female mice using the VELOCIMOUSE® method (see, e.g., U.S. Pat. No. 7,294,754 and Poueymirou et al., 2007, Nature Biotech. 25(1):91-99) to generate a litter of pups containing an insertion of human PDCD1 exon 2 and part of human PDCD1 exon 3 into an endogenous Pdcd1 gene of a mouse. Mice bearing the humanization of exon 2 and 3 in part (i.e., the 883 bp human DNA fragment) of an endogenous Pdcd1 gene were again confirmed and identified by genotyping of DNA isolated from tail snips using a modification of allele assay (Valenzuela et al., supra) that detected the presence of the human PDCD1 gene sequences. Pups are genotyped and cohorts of animals heterozygous for the humanized Pdcd1 gene construct are selected for characterization.

TABLE 4

| Name | Primer | Sequence (5'-3') | |
|---|---|---|---|
| 7106 hTU | Forward | CCCAGCAGAGACTT CTCAATGAC | (SEQ ID NO: 7) |
| | Probe | TGGCCCTTCCAGAG CCCTTG | (SEQ ID NO: 8) |
| | Reverse | CGGCCACCTGCTCA CATC | (SEQ ID NO: 9) |
| 7106 hTD | Forward | GGCATCTCTGTCCT CTAGCTC | (SEQ ID NO: 10) |
| | Probe | AAGCACCCCAGCCC CTCTAGTCTG | (SEQ ID NO: 11) |
| | Reverse | GGGCTGTGGGCACT TCTG | (SEQ ID NO: 12) |
| 7106 TU | Forward | CCTTCCTCACAGCT CTTTGTTC | (SEQ ID NO: 13) |
| | Probe | TCTGCATTTCAGAG GTCCCCAATGG | (SEQ ID NO: 14) |
| | Reverse | GAGCCAGGCTGGGT AGAAG | (SEQ ID NO: 15) |
| 7106 TD | Forward | CGGTGTCCTAGAAC TCTATTCTTTG | (SEQ ID NO: 16) |
| | Probe | TCCTGGAGACCTCA ACAAGATATCCCA | (SEQ ID NO: 17) |
| | Reverse | TGAAACCGGCCTTC TGGTT | (SEQ ID NO: 18) |

Example 2

Expression of Humanized PD-1 on Activated T Cells

This Example demonstrates that non-human animals (e.g., rodents) modified to contain a humanized Pdcd1 gene according to Example 1 express a humanized PD-1 protein on the surface of activated lymphocytes. In this Example, activated T cells from mice heterozygous for humanization of an endogenous Pdcd1 gene as described in Example 1 were stained with anti-PD-1 antibodies to determine the expression of PD-1 in stimulated T cells isolated from wild-type and humanized mice.

Briefly, spleens were harvested and processed from a wild-type mouse and a mouse heterozygous for humanization of an endogenous Pdcd1 gene as described in Example 1 into single cell suspensions by mechanical dissociation. Cells were washed in media (RPMI supplemented with 10% FBS) and re-suspended at $1 \times 10^6$/mL and 200 μL (200,000 cells) were plated in 96-well plates. Cells in selected wells were stimulated with anti-CD3 and anti-CD28 antibodies (both at 1 μg/mL) for 72 hours. Cells were stained for FACS according to manufacturer's specifications with antibodies recognizing CD4, CD8, CD19 and human (clone MIH4, BD Biosciences) or mouse (clone J43, eBioscience) PD1. Stained cells were ran on LSRII flow cytometer and data was analyzed using Flowjo software. $CD8^+$ T cells were gated ($CD19^-CD8^+$) for expression of human and mouse PD1. Exemplary results are shown in FIG. 4.

Figure 4:
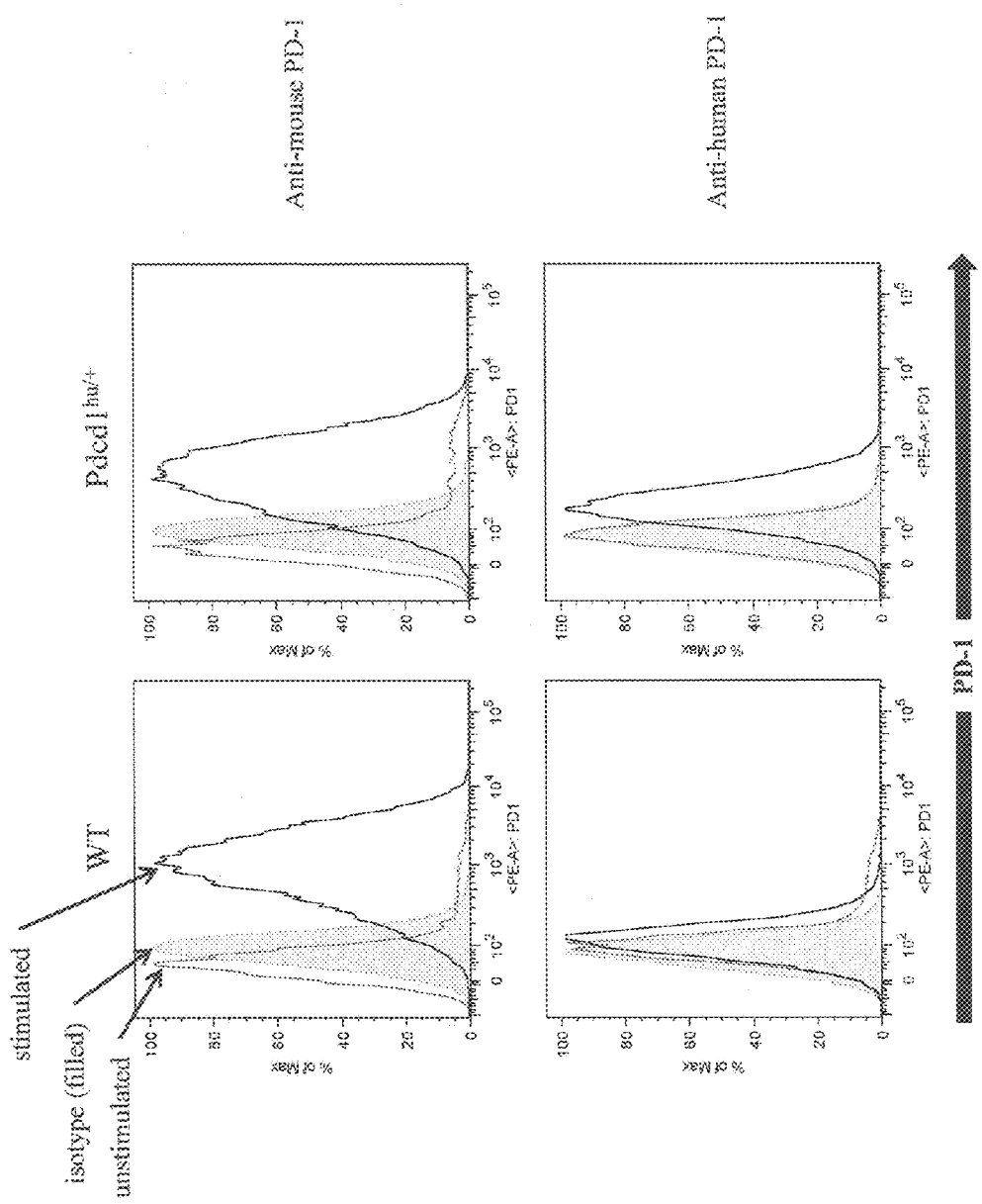
FIG. 4 shows exemplary histograms of T cells gated on CD19 and CD8 isolated from a wild-type mouse and a mouse heterozygous for humanization of an endogenous Pdcd1 gene as described in Example 1 that express mouse and/or humanized PD-1. Stimulated and unstimulated cell populations are indicated, as are cells stained with an isotype control.

As shown in FIG. 4, mice bearing a humanized Pdcd1 gene as described in Example 1 express a PD-1 polypeptide that comprises a human portion and an endogenous mouse portion. The human portion is detectably expressed via recognition by an antibody that recognizes a fully human PD-1 polypeptide.

Example 3

In Vivo Efficacy of PD-1 Modulators

This Example demonstrates that non-human animals (e.g., rodents) modified to contain a humanized Pdcd1 gene according to Example 1 can be used in an in vivo assay to screen PD-1 modulators (e.g., anti-PD-1 antibodies) and determine various characterisitics such as, for example, inhibition of tumor growth and/or killing of tumor cells. In this Example, several anti-PD-1 antibodies are screened in mice homozygous for humanization of an endogenous Pdcd1 gene as described in Example 1 to determine the optimal antibody dose that inhibits tumor growth and the extent to which anti-PD-1 antibodies mediate killing of tumor cells.

Briefly, mice were divided evenly according to body weight into five treatment or control groups for Study 1 (n=5/group), eight treatment or control groups for Study 2 (n=5/group), and five treatment or control groups for Study 3 (n=7/group). At day zero, mice were anesthetized by isoflurane inhalation and then subcutaneously injected with MC38.ova cells in suspension of 100 μL of DMEM into the right flank (Study 1: $5 \times 10^5$; Study 2/3: $1 \times 10^6$). MC38.ova (mouse colon adenocarcinoma) cells were engineered to express chicken ovalbumin in order to increase tumor immunogenicity. For Study 1, treatment groups were intraperitoneally injected with 200 μg of either one of three anti-PD-1 antibodies, or an isotype control antibody with irrelevant specificity on days 3, 7, 10, 14, and 17 of the experiment, while one group of mice was left untreated. For Study 2, treatment groups were intraperitoneally injected with either one of three anti-PD-1 antibodies at 10 mg/kg or 5 mg/kg per/dose, one anti-PD-1 antibody (Ab B, IgG4) at 10 mg/kg per dose, or an isotype control antibody with irrelevant specificity at 10 mg/kg on days 3, 7, 10, 14, and 17 of the experiment. For Study 3, treatment groups were intraperitoneally injected with either one of two anti-PD-1 antibodies at 5 mg/kg or 2.5 mg/kg per/dose, or a control antibody not specific to PD-1 (control) at 5 mg/kg on days 3, 7, 10, 14, and 17 of the experiment. Table 5 sets forth experimental dosing and treatment protocol for groups of mice.

For each of the studies, average tumor volumes determined by caliper measurements and percent survival at Day 14 or 17 and Day 23 or 24 of each experiment for each treatment group were recorded. The number of tumor-free mice were also assessed at the end of the study (Day 42 for Study 1 and Day 31 for Study 2 and Study 3). Mean tumor volume (mm$^3$)($\pm$SD), percent survival, and number of tumor-free mice were calculated for each study (Tables 7-9). Exemplary tumor growth curves are provided in FIG. 5.

As shown in Table 6 for Study 1, mice treated with Ab A did not develop any detectable tumors during the course of the study. Mice treated with Ab C exhibited a sustained reduced tumor volume as compared to controls at days 17 and 24 of the study; and 3 out of 5 mice were tumor free by the end of the experiment. In contrast, treatment with Ab B did not demonstrate significant efficacy in reducing tumor volume in this study as compared to controls. By day 23 of the study, 1 out of 5 mice died in the group that received Ab B, and 2 out of 5 mice died in the isotype control treatment group. In non-treatment and isotype control groups, some mice exhibited spontaneous regression of tumors (1 out of 5 mice and 2 out of 5 mice, respectively).

As shown in Table 7 for Study 2, mice treated with Ab A at 10 mg/kg did not develop detectable tumors during the course of the study. Groups of mice treated with 10 mg/kg of either Ab C or Ab D exhibited substantially reduced tumor volume as compared to controls at days 17 and 24 of the study. Four out of 5 mice in each group treated with 10 mg/kg of either Ab C or Ab D were tumor free at Day 31, whereas in the isotype control treatment group only 1 out of 5 animals was tumor free as a result of spontaneous tumor regression. Ab B tested at 10 mg/kg demonstrated substantially reduced tumor volume as compared to controls at days 17 and 24 of the study, but this antibody was the least efficacious anti-PD1 antibody with only 2 out of 5 mice surviving at the end of the experiment.

A dose-dependent response in tumor suppression at the tested doses (5 mg/kg and 10 mg/kg) was observed in groups treated with Ab A, Ab C, and Ab D. Ab A or Ab C therapy at 5 mg/kg was less efficacious, with 4 out of 5 tumor-free mice at the end of experiment on day 31, whereas 5 out of 5 mice remained tumor-free in 10 mg/kg dose group of Ab A. Dunett's test in 2 way ANOVA multiple comparisons revealed that the differences in tumor growth between the group treated with isotype control antibody at 10 mg/kg as reference and the groups treated at 10 mg/kg with Ab A, Ab C or Ab D were statistically significant with p value <0.005. The differences in tumor growth between the group treated with isotype control antibody at 10 mg/kg as reference and the groups treated at 5 mg/kg with Ab A, Ab C or Ab D were also statistically significant with a p value <0.05.

As shown in Table 8 for Study 3, 6 out or 7 mice treated with Ab A or Ab C at 5 mg/kg were tumor free at the end of the experiment, whereas there were no tumor free animals in the isotype control group. One tumor-bearing mouse in the IgG4 control group died on post-implantation day 17. Only 4 out of 7 mice treated with Ab C at 2.5 mg/kg remained tumor free at the end of the experiment. The difference in tumor volumes at day 21 between anti-PD-1 antibodies tested and an isotype control group was statistically significant as determined by one-way ANOVA with Dunnett's multiple comparison post-test with p<0.01. All four anti-PD-1 antibodies tested were equally more efficacious at the 5 mg/kg dose than at the 2.5 mg/kg dose.

Figure 5:
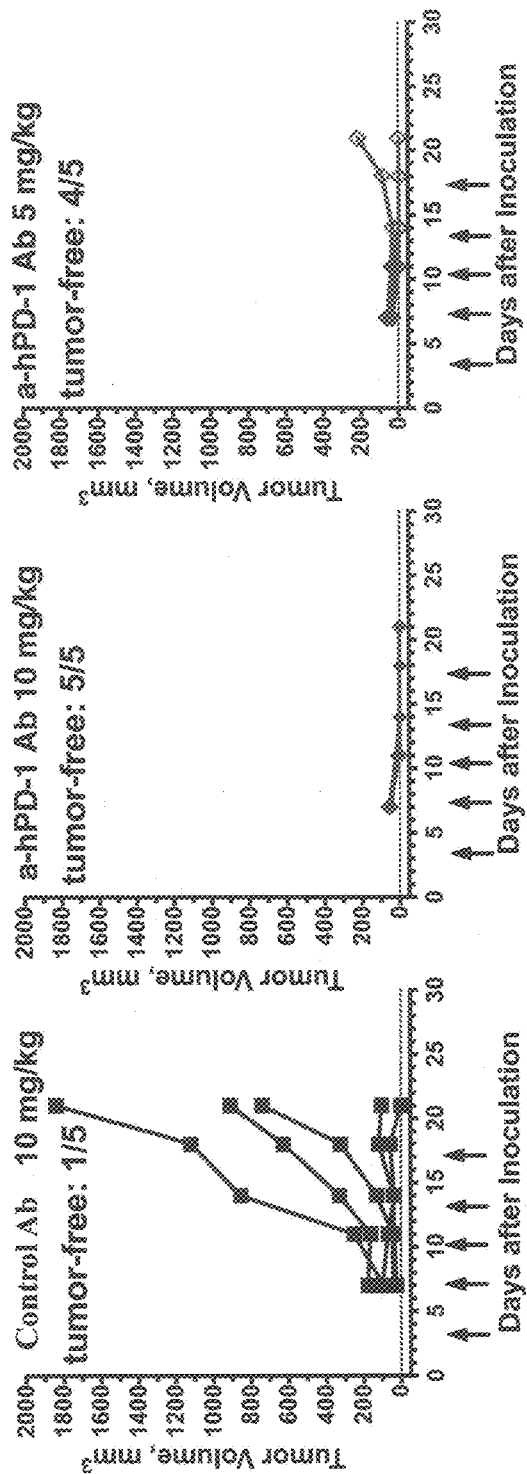
FIG. 5 shows exemplary tumor growth curves over 21 days in mice homozygous for humanization of an endogenous Pdcd1 gene as described in Example 1. Control: antibody not specific for PD-1, a-hPD-1 Ab: antibody specific for human PD-1. Arrows indicate the days for antibody treatment. The number of tumor-free mice on day 21 is shown for each treatment group.

As shown in FIG. 5, anti-PD-1 antibodies significantly inhibited tumor growth in a prophylactic MC38.ova tumor growth model in PD-1 humanized mice made according to Example 1. Anti-PD-1 Ab therapy at 10 mg/kg promoted tumor regression in all mice (5 out of 5) throughout the course of the experiment, whereas only one out of five animals remained tumor-free in the control group resulting from spontaneous tumor regression. Anti-PD-1 therapy at 5 mg/kg was slightly less efficacious, with four out of five tumor-free mice at the end of the experiment. One-way ANOVA with Dunnett's multiple comparison post-test revealed a significant difference in tumor volumes between anti-PD-1 and control antibody treatments with a p value <0.05 (5 mg/kg) and p value <0.01 (10 mg/kg).

In a similar experiment, intact functional PD-1 signaling in PD-1 humanized mice made according to Example 1 was investigated by measuring CD8$^+$ T cells and CD3$^+$ T cells responses and IFN$\gamma$ production in spleens of tumor-bearing mice treated with anti-PD-1 antibody.

Briefly, spleen cells were obtained from PD-1 humanized mice (75% C57BL/6/25% 129) treated with anti-PD-1 or control antibody at the end of the experiments on Day 21 (described above). Total RNA was isolated, and real-time PCR was performed on reverse transcribed cDNA using oligonucleotides and taqman probe mix specific for mouse CD8b (forward primer: GCTCTGGCTG GTCTTCAGTA TG, SEQ ID NO:24; reverse primer: TTGCCGTATG GTTGGTTTGA AC, SEQ ID NO:25; probe: AGCA-GCTCTG CCCTCAT, SEQ ID NO:26), mouse CD3$\zeta$ (Mm00446171_m1, Applied Biosystems), mouse IFN-$\gamma$ (Mm01168134_m1, Applied Biosystems), human PD-1 (forward primer: ACTTCCACAT GAGCGTGG, SEQ ID NO:27; reverse primer: GGGCTGTGGG CACTTCTG, SEQ ID NO:28; probe: GCAGATCAAA GAGAGCCTGC, SEQ ID NO:29) and mouse PD-1 (Mm01285676_m1, Applied Biosystems). Samples were normalized relative to expression of mouse cyclophilin B. Exemplary results are provided in FIG. 6.

Figure 6:
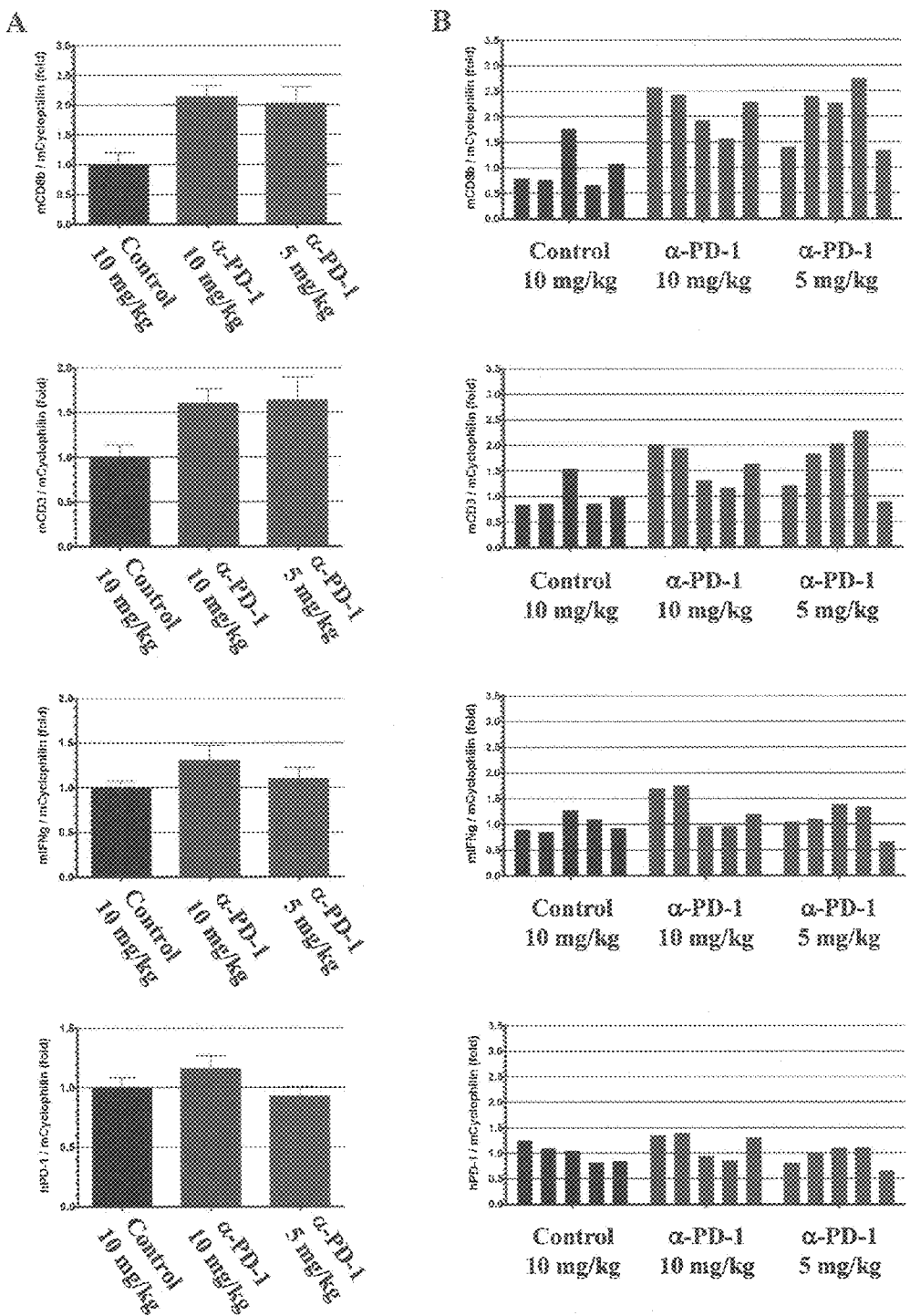
FIG. 6 shows exemplary real-time PCR analysis of CD8b, CD3, IFN-g and PD-1 mRNA expression in spleens in mice homozygous for humanization of an endogenous Pdcd1 gene as described in Example 1 after treatment with anti-PD-1 antibody. A, mean of five mice per group. B, expression levels for individual mice in each treatment group. Control: antibody not specific for PD-1; α-PD-1: anti-PD-1 antibody.

As shown in FIG. 6, administration of anti-hPD-1 antibody induced increased production of CD8$^+$ and CD3$^+$ T cells in spleens of humanized mice (made according to Example 1) bearing MC38.ova tumors. Further, activity of anti-hPD-1 antibody in tumor bearing PD-1 humanized mice was dependent on IFN$\gamma$, which confirmed proper signaling through humanized PD-1 on the cell surface. Overall, an increase in T cells and IFN$\gamma$ as compared to control-treated mice was observed for both treatment groups.

Human PD-1 mRNA expression was measured with human specific probes designed for the extracellular portion of the PD-1 protein and confirmed proper expression of humanized PD-1 protein on the cell surface. Additionally, measurement of mouse PD-1 mRNA expression with primers designed to detect the extracellular portion of mouse PD-1 failed to produce a product.

Taken together, this Example demonstrates that non-human animals of the present invention can be used to assess the in vivo efficacy of drugs (e.g., an antibody) targeting PD-1, and such animals are useful in discriminating the therapeutic effect of anti-PD-1 antibodies. Moreover, non-human animals described herein can be used to assess the extent to which drugs targeting PD-1 can inhibit tumor growth and/or mediate killing of tumor cells. Non-human animals (e.g., mice) of the present invention demonstrate functional PD-1-signaling and proper PD-1-dependent immune responses via humanized PD-1 as evidenced by expansion of T cells and cytokine expression (e.g., IFN-γ).

TABLE 5

| Study # | Antibody | Dosage |
|---|---|---|
| 1 | Isotype Control | 200 μg |
|   | No treatment | N/A |
|   | Ab A | 200 μg |
|   | Ab B | 200 μg |
|   | Ab C | 200 μg |
| 2 | Isotype Control | 10 mg/kg |
|   | Ab A | 10 mg/kg |
|   | Ab A | 5 mg/kg |

TABLE 5-continued

| Study # | Antibody | Dosage |
|---|---|---|
|   | Ab B | 10 mg/kg |
|   | Ab C | 10 mg/kg |
|   | Ab C | 5 mg/kg |
|   | Ab D | 10 mg/kg |
|   | Ab D | 5 mg/kg |
| 3 | Isotype Control | 5 mg/kg |
|   | Ab A | 5 mg/kg |
|   | Ab A | 2.5 mg/kg |
|   | Ab C | 5 mg/kg |
|   | Ab C | 2.5 mg/kg |

TABLE 6

Study 1

| Treatment group (n = 5) | Mean tumor volume ($mm^3$, ±SD) | | Survival (%) | | Tumor free mice |
|---|---|---|---|---|---|
|   | Day 17 200 μg/mouse | Day 23 200 μg/mouse | Day 17 200 μg/mouse | Day 23 200 μg/mouse | Day 42 200 μg/mouse |
| No treatment | 189 (±110) | 554 (±317) | 100% | 100% | 1/5 |
| Isotype Control | 86 (±114) | 515 (±859) | 100% | 60% | 2/5 |
| Ab A | 0 (0) | 0 (0) | 100% | 100% | 5/5 |
| Ab B | 89 (±176) | 445 (±889) | 100% | 80% | 3/5 |
| Ab C | 14 (±19) | 205 (±312) | 100% | 100% | 3/5 |

TABLE 7

Study 2

| Treatment group (n = 5) | Mean tumor volume ($mm^3$; ±SD) | | | | Survival (%) | | | | Tumor free Mice | |
|---|---|---|---|---|---|---|---|---|---|---|
|   | Day 17 | | Day 24 | | Day 17 | | Day 24 | | Day 31 | |
|   | 5 mg/kg | 10 mg/kg | 5 mg/kg | 10 mg/kg | 5 mg/kg | 10 mg/kg | 5 mg/kg | 10 mg/kg | 5 mg/kg | 10 mg/kg |
| Isotype Control | N/A | 449 (±434) | N/A | 824 (±858) | N/A | 100% | N/A | 60% | N/A | 1/5 |
| Ab A | 17 (±38) | 0 (0) | 104 (±233) | 0 (0) | 100 | 100 | 100 | 100 | 4/5 | 5/5 |
| Ab B | N/A | 124 (±209) | N/A | 359 (±657) | N/A | 100 | N/A | 80 | N/A | 2/5 |
| Ab C | 91 (±204) | 12 (±28) | 228 (±509) | 96 (±215) | 100 | 100 | 80 | 100 | 4/5 | 4/5 |
| Ab D | 94 (±160) | 10 (±21) | 328 (±559) | 67 (±150) | 100 | 100 | 80 | 100 | 3/5 | 4/5 |

TABLE 8

Study 3

| Treatment group (n = 7) | Mean tumor volume ($mm^3$; ±SD) | | | | Survival (%) | | | | Tumor free mice | |
|---|---|---|---|---|---|---|---|---|---|---|
|   | Days 14 | | Day 21 | | Day 14 | | Day 21 | | Day 31 | |
|   | 2.5 mg/kg | 5 mg/kg | 2.5 mg/kg | 5 mg/kg | 2.5 mg/kg | 5 mg/kg | 2.5 mg/kg | 5 mg/kg | 2.5 mg/kg | 5 mg/kg |
| Isotype Control | N/A | 94 (±44) | N/A | 405 (±326) | N/A | 100 | N/A | 86 | N/A | 0/7 |
| Ab A | 0 (0) | 0 (0) | 19 (±51) | 13 (±35) | 100 | 100 | 100 | 100 | 6/7 | 6/7 |
| Ab C | 41 (±68) | 7 (±20) | 87 (±123) | 16 (±42) | 100 | 100 | 100 | 100 | 4/7 | 6/7 |

Example 4

Rodent Model of Anti-PD-1 Tumor Therapy

This Example demonstrates that non-human animals (e.g., rodents) modified to contain a humanized Pdcd1 gene according to Example 1 can be used in a tumor model to determine optimal therapeutic dose(s) of PD-1 modulators (e.g., anti-PD-1 antibodies). In this Example, an anti-PD-1 antibody is administered to mice homozygous for humanization of an endogenous Pdcd1 gene as described in Example 1 to determine the optimal therapeutic dose for treatment of established tumors.

Briefly, mice containing a humanized Pdcd1 gene (as described in Example 1) were subcutaneously implanted with $1 \times 10^6$ MC38.Ova cells (described above) and subsequently randomized into six treatment groups (n=8-9 per group) once tumor volumes reached 80-120 mm$^3$ (day 0). Mice were intraperitoneally administered anti-hPD-1 antibody in an escalating dose range of 0.3-25 mg/kg (i.e., 0.3, 1, 3, 10 or 25 mg/kg) or an isotype control antibody at 25 mg/kg. Antibodies were dosed on days 0, 3, 7, 10 and 13. Tumor volumes were monitored by calipered measurements twice per week for the duration of the experiment (60 days). Exemplary tumor growth curves are provided in FIG. 7.

Figure 7:
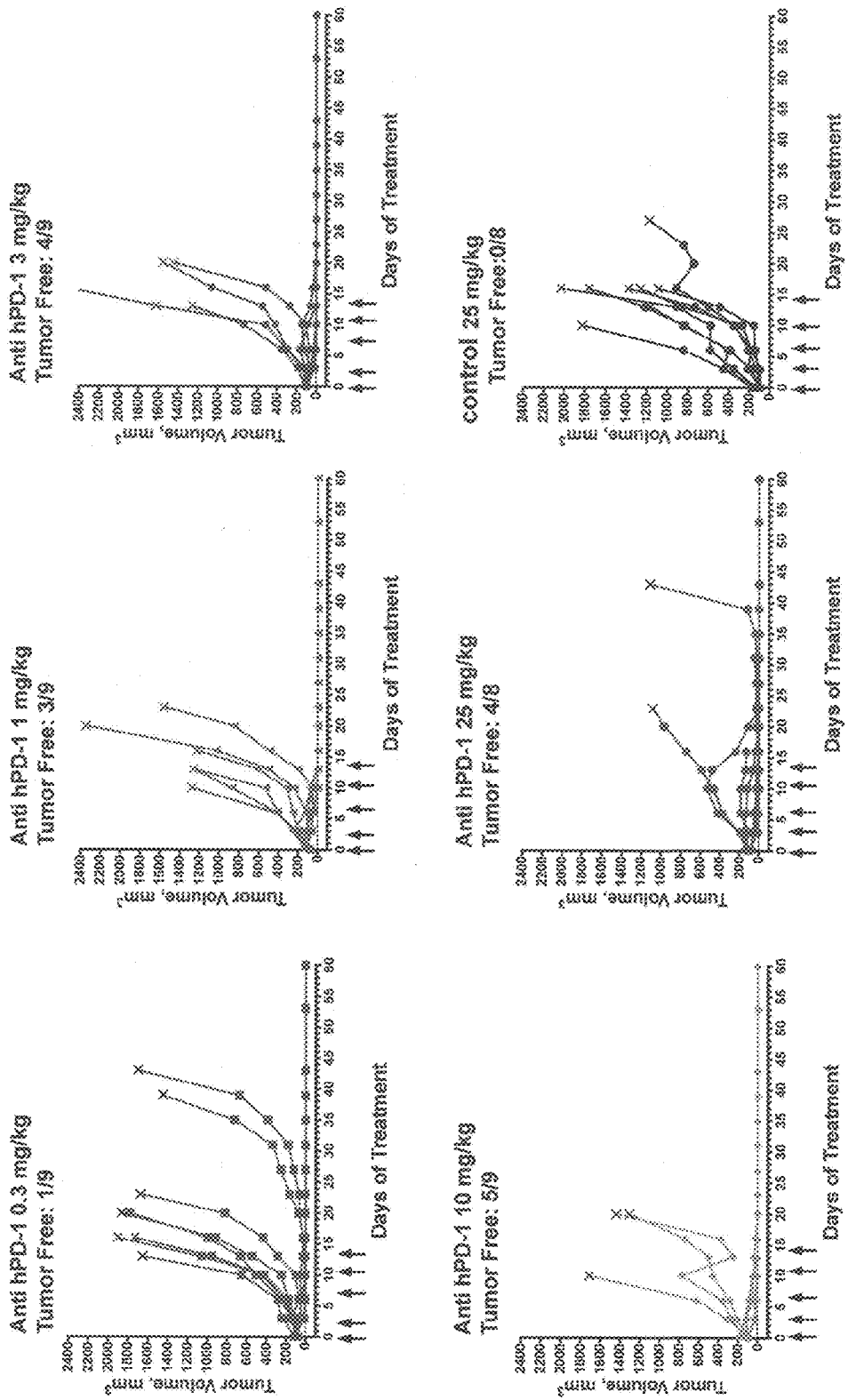
FIG. 7 shows exemplary tumor growth curves over 60 days in mice homozygous for humanization of an endogenous Pdcd1 gene as described in Example 1 that were administered 0.3-25 mg/kg of anti-hPD-1 antibody or 25 mg/kg of control antibody (antibody not specific for PD-1). Arrows indicate the days of antibody treatment. The number of tumor-free mice on day 60 is shown for each treatment group.

As shown in FIG. 7, none of the mice administered the control antibody were tumor free at the end of the experiment. In contrast, a dose range of 3-25 mg/kg anti-hPD-1 antibody resulted in about 44-55% tumor free mice among the different treatment groups. Taken together, this Example demonstrates that non-human animals of the present invention can be used as a rodent tumor model to determine the optimal dose and/or dose range of drugs (e.g., an antibody) targeting PD-1 to effectively treat established tumors.

EQUIVALENTS

Having thus described several aspects of at least one embodiment of this invention, it is to be appreciated by those skilled in the art that various alterations, modifications, and improvements will readily occur to those skilled in the art. Such alterations, modifications, and improvements are intended to be part of this disclosure, and are intended to be within the spirit and scope of the invention. Accordingly, the foregoing description and drawing are by way of example only and the invention is described in detail by the claims that follow.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification.

Those skilled in the art will appreciate typical standards of deviation or error attributable to values obtained in assays or other processes described herein. The publications, websites and other reference materials referenced herein to describe the background of the invention and to provide additional detail regarding its practice are hereby incorporated by reference.

We claim:

1. A mouse whose genome comprises a humanized Programmed cell death 1 (Pdcd1) gene at an endogenous Pdcd1 locus,
    wherein the humanized Pdcd1 gene comprises exon 2, and comprises exon 3 in whole or in part, of a human Pdcd1 gene,
    wherein the humanized Pdcd1 gene is operably linked to a Pdcd1 promoter and expresses a humanized Programmed cell death 1 (PD-1) polypeptide on the surface of activated T cells in the mouse, and
    wherein the humanized PD-1 polypeptide comprises the N-terminal immunoglobulin V domain of a human PD-1 polypeptide and the intracellular domain of an endogenous mouse PD-1 polypeptide.

2. The mouse of claim 1, wherein the humanized PD-1 polypeptide is translated in a cell of the mouse with a mouse signal peptide.

3. The mouse of claim 1, wherein the humanized PD-1 polypeptide comprises the transmembrane sequence of the endogenous PD-1 polypeptide.

4. The mouse of claim 1, wherein the humanized PD-1 polypeptide comprises amino acids 26-169 of a human PD-1 polypeptide.

5. The mouse of claim 1, wherein the humanized Pdcd1 gene comprises endogenous Pdcd1 exons 1, 4 and 5.

6. The mouse of claim 5, wherein the humanized Pdcd1 gene further comprises an endogenous Pdcd1 exon 3 in part.

7. The mouse of claim 1 wherein the Pdcd1 promoter is a rodent Pdcd1 promoter.

8. The mouse of claim 1, wherein the Pdcd1 promoter is an endogenous mouse Pdcd1 promoter.

9. The mouse of claim 1, wherein the humanized Pdcd1 gene comprises the nucleotide sequence as set forth in SEQ ID NO: 23.

10. The mouse of claim 1, wherein the mouse is homozygous for the humanized Pdcd1 gene.

11. The mouse of claim 1, wherein the mouse does not detectably express a full length endogenous mouse PD-1 polypeptide.

12. A humanized PD-1 polypeptide produced by the mouse of claim 11.

13. The mouse of claim 1, wherein the humanized Pdcd1 gene comprises the part of exon 3 of the human Pdcd1 gene that encodes amino acids of the extracellular domain of the human PD-1 polypeptide.

14. The mouse of claim 13, wherein the humanized Pdcd1 gene comprises endogenous mouse Pdcd1 exon 1, exon 3 in part, exon 4 and exon 5.

15. The mouse of claim 13, wherein the humanized PD-1 polypeptide comprises the transmembrane and intracellular domains of the endogenous mouse PD-1 polypeptide.

* * * * *